(12) United States Patent
Kleinschmidt et al.

(10) Patent No.: US 9,657,089 B2
(45) Date of Patent: May 23, 2017

(54) DIAGNOSTIC ANTIBODY ASSAY

(71) Applicant: Probiodrug AG, Halle/Saale (DE)

(72) Inventors: Martin Kleinschmidt, Halle/Saale (DE); Stephan Schilling, Halle/Saale (DE); Jens-Ulrich Rahfeld, Gemeinde Seegebiet Mansfelder Land (DE); Kristin Ebermann, Zittau (DE); Hans-Ulrich Demuth, Halle/Saale (DE)

(73) Assignee: PROBIODRUG AG, Halle/Saale (DE)

( * ) Notice: Subject to any disclaimer, the term of this patent is extended or adjusted under 35 U.S.C. 154(b) by 0 days.

(21) Appl. No.: 14/280,919

(22) Filed: May 19, 2014

(65) Prior Publication Data

US 2014/0255414 A1 Sep. 11, 2014

Related U.S. Application Data

(62) Division of application No. 13/422,583, filed on Mar. 16, 2012, now Pat. No. 8,809,508.

(60) Provisional application No. 61/453,449, filed on Mar. 16, 2011.

(51) Int. Cl.
*A61K 39/395* (2006.01)
*C07K 16/18* (2006.01)
*G01N 33/68* (2006.01)
*A61K 39/00* (2006.01)

(52) U.S. Cl.
CPC .......... *C07K 16/18* (2013.01); *A61K 39/3955* (2013.01); *G01N 33/6896* (2013.01); *A61K 2039/505* (2013.01); *C07K 2317/24* (2013.01); *C07K 2317/56* (2013.01); *C07K 2317/92* (2013.01); *G01N 2333/4709* (2013.01); *G01N 2800/2821* (2013.01)

(58) Field of Classification Search
CPC ................ C07K 16/18; C07K 2317/92; C07K 2317/24; C07K 2317/56; A61K 39/3955; A61K 2039/505
See application file for complete search history.

(56) References Cited

U.S. PATENT DOCUMENTS

| 7,117,096 B2 | 10/2006 | Luo et al. |
| 2006/0088548 A1 | 4/2006 | Chain |
| 2010/0021478 A1 | 1/2010 | Demuth et al. |
| 2012/0100129 A1 | 4/2012 | Gellerfors et al. |

FOREIGN PATENT DOCUMENTS

| EP | 1881008 | 1/2008 | |
| SE | WO 2011001366 A1 * | 1/2011 | ......... C07K 14/4711 |
| WO | WO 2004/013172 | 2/2004 | |
| WO | WO 2004/029630 | 4/2004 | |
| WO | WO 2005/075436 | 8/2005 | |
| WO | WO 2008/002893 | 1/2008 | |
| WO | WO 2008/055945 | 5/2008 | |
| WO | WO 2008/055947 | 5/2008 | |
| WO | WO 2008/055950 | 5/2008 | |
| WO | WO 2008/065141 | 6/2008 | |
| WO | WO 2008/110523 | 9/2008 | |
| WO | WO 2008/128981 | 10/2008 | |
| WO | WO 2008/128982 | 10/2008 | |
| WO | WO 2008/128983 | 10/2008 | |
| WO | WO 2008/128984 | 10/2008 | |
| WO | WO 2008/128985 | 10/2008 | |
| WO | WO 2008/128986 | 10/2008 | |
| WO | WO 2009/149485 | 12/2009 | |
| WO | WO 2010/128139 | 11/2010 | |

OTHER PUBLICATIONS

Bard F et al. Peripherally administered antibodies against amyloid beta-peptide enter the central nervous system and reduce beta-pathology in a mouse model of Alzheimer disease. Nat Med. 2000, 6(8):916-919.*
DeMattos RB et al. Peripheral anti-Abeta antibody alters CNS and plasma Abeta clearance and decreases brain Abeta burden in a mouse model of Alzheimer's disease. Proc Natl Acad Sci USA, 98(15):8850-8855.*
Gunn AP et al. Pyroglutamate-Abeta: Role in the natural history of Alzheimer's disease. Int. J. Biochem. Cell Biol. 2010, 42:1915-1918.*
Hampel H et al. The future of Alzheimer's disease: The next 10 years. Progress Neurobiol. 2011, 95:718-728.*
Lee EB et al. Targeting amyloid-beta peptide (Abeta) oligomers by passive immunization with a conformation-selective monoclonal antibody improves learning and memory in Abeta precursor protein (APP) transgenic mice. J. Biol Chem. Feb. 2006; 281(7):4292-4299.*
Lemere CA et al. Amyloid-beta immunotherapy for the prevention and treatment of Alzheimer disease: Lessons from mice, monkeys and humans. Rejuvenation Res. 2006; 9(1):77-84.*
Vickers JC. A vaccine against Alzheimer's disease, Developments to date. Drugs Aging. 2002; 19(7):487-494.*
Abcam, KD values. Retrieved from internet Nov. 25, 2015.*
Russo et al., Presenilin-1 mutations in Alzheimer's disease, Nature, 2000, pp. 531-532, vol. 405.
Akiyama et al., Occurrence of the Diffuse Amyloid β-Protein (Aβ) Deposits With Numerous Aβ-Containing Glial Cells in the Cerebral Cortex of Patients With Alzheimer's Disease, Glia, 1999, pp. 324-331, vol. 25.
Alberts et al., Molecular Biology of the Cell, Third Edition, 1994, pp. 1216-1220.
Cynis et al., Inhibition of glutaminyl cyclase alters pyroglutamate formation in mammalian cells, Biochim Biophys Acta, 2006, pp. 1618-1625, vol. 1764, No. 10.

(Continued)

*Primary Examiner* — Kimberly A. Ballard
(74) *Attorney, Agent, or Firm* — Dentons US LLP

(57) ABSTRACT

Diagnostic assays for the diagnosis of amyloidosis, in particular Alzheimer's disease, and related aspects. In particular, monoclonal antibodies and an antibody assay are provided.

20 Claims, 16 Drawing Sheets

(56) References Cited

OTHER PUBLICATIONS

Dandulakis et al., Cell Growth and Monoclonal Antibody Production in the Presence of Antigen and Serum, Biotechnol Prog, 1995, pp. 518-524, vol. 11, No. 5, 1995.
Greenfield et al., Endoplasmic reticulum and trans-Golgi network generate distinct populations of Alzheimer β-amyloid peptides, Proc Natl Acad Sci USA, 1999, pp. 742-747, vol. 96, No. 2.
Hardy et al., Alzheimer's Disease: The Amyloid Cascade Hypothesis, Science, 1992, pp. 184-185, vol. 256.
Holliger et al., "Diabodies": Small bivalent and bispecific antibody fragments, Proc Natl Acad Sci USA, 1993, pp. 6444-6448, vol. 90.
Iwatsubo et al., Visualization of Aβ42(43) and Aβ40 in Senile Plaques with End-Specific Aβ Monoclonals: Evidence That an Initially Deposited Species Is Aβ42(43), Neuron, 1994, pp. 45-53, vol. 13.
Iwatsubo et al., Amyloid β Protein (Aβ) Deposition: Aβ42(43) Precedes Aβ40 in Down Syndrome, Annals of Neurology, 1995, pp. 294-299, vol. 37, American Neurological Association.
Iwatsubo et al., Full-Length Amyloid-β(1-42(43)) and Amino-Terminally Modified and Truncated Amyloid-β42(43) Deposit in Diffuse Plaques, American Journal of Pathology, 1996, pp. 1823-1830, vol. 149, No. 6.
Jones et al., Replacing the complementarity-determining regions in a human antibody with those from a mouse, Nature, 1986, pp. 522-525, vol. 321.
Köhler et al., Continuous cultures of fused cells secreting antibody of predefined specificity, Nature, 1975, pp. 495-497, vol. 256.
Kuby et al, Immunology, Third Edition, WH Freeman & Co., New York,1997, pp. 131-134.
Liu, et al., Characterization of Aβ11-40/42 peptide deposition in Alzheimer's disease and young Down's syndrome brains: implication of N-terminally truncated Aβ species in the pathogenesis of Alzheimer's disease, Acta Neuropathologica, 2006, pp. 163-174, vol. 112, No. 2.
Marcello et al., Reduced levels of IgM autoantibodies against N-trucated pyroglutamate Aβ in plasma of patients with Alzheimer's disease, Neurobiology of Aging, 2011 (available online 2009), pp. 1379-1387, vol. 32.
Marks et al., By-passing Immunization Human Antibodies from V-gene Libraries Displayed on Phage, J Mol Biol, 1991, pp. 581-597, vol. 222.
McGeer et al., Pathological Proteins in Senile Plaques, Tohoku J Exp Med, 1994, pp. 269-277, vol. 174, No. 3.
Murakami et al., Growth of hybridoma cells in serum-free medium: Ethanolamine is an essential component, Proc Natl Acad Sci USA, 1982, pp. 1158-1162, vol. 79.
Näslund et al., Relative abundance of Alzheimer Aβ amyloid peptide variants in Alzheimer disease and normal aging, Proc. Natl. Acad. Sci. USA, 1994, pp. 8378-8382, vol. 91.
Ozturk et al., Effect of initial cell density on hybridoma growth, metabolism, and monoclonal antibody production, Journal of Biotechnology, 1990, pp. 259-278, vol. 16.
Paul et al., Fundamental Immunology, Third Edition, Raven Press, New York, 1993, pp. 292-295.
Perez-Garmendia et al., Anti-11[E]-pyroglutamate-modified amyloid β antibodies cross-react with other pathological Aβ species: Relevance for immunotherapy, J of Neuroimmunology, 2010, pp. 248-255, vol. 229.
Piccini et al., β-Amyloid is Different in Normal Aging and in Alzheimer Disease, Journal of Biological Chemistry, 2005, pp. 34186-34192, vol. 280, No. 40.
Plückthun, Antibodies from *Escherichia coli*, The pharmacology of Monoclonal Antibodies, 1994, pp. 269-315, vol. 113, Rosenburg and Moore eds., Springer-Verlag, New-York.
Pohl et al., Primary structure and functional expression of a glutaminyl cyclase, Proc Natl Acad Sci USA, Biochemistry, 1991, pp. 10059-10063, vol. 88, No. 22.
Presta, Antibody engineering, Current Opinion in Biotechnology, 1992, pp. 394-398, vol. 3.
Reichmann et al., Reshaping human antibodies for therapy, Nature, 1988, pp. 323-329, vol. 332.
Renard et al., Evidence that Monoclonal Antibody Production Kinetics is Related to the Integral of the Viable Cells Curve in Batch Systems, Biotechnology Letters, 1988, pp. 91-96, vol. 10, No. 2.
Roβner et al., The Regulation of Amyloid Precursor Protein Metabolism by Cholinergic Mechanisms and Neurotrophin Receptor Signaling, Progress in Neurobiology, 1998, pp. 541-596, vol. 56.
Rudikoff et al., Single amino acid substitution altering antigen-binding specificity, Proc. Natl. Acad. Sci., 1982, pp. 1979-1983, vol. 79, No. 6.
Russo et al., Pyroglutamate-modified amyloid β-peptides—AβN3(pE)—strongly affect cultured neuron and astrocyte survival, Journal of Neurochemistry, 2002, pp. 1480-1489, vol. 82, No. 6.
Saido et al., Dominant and Differential Deposition of Distinct β-Amyloid Peptide Species, Aβn3(pE), in Senile Plaques, Neuron, 1995, pp. 457-466, vol. 14, No. 2.
Saido et al, Amino- and carboxyl-terminal hetrogeneity of β-amyloid peptides deposited in human brain, Neurosciences Letters, 1996, pp. 174-176, vol. 215, No. 3.
Saido et al., Alzheimer's Disease as Proteolytic Disorders: Anabolism and Catabolism of β-Amyloid, Neurobiology of Aging, 1998, pp. S69-S75, vol. 19, No. 1S.
Schilling et al., Glutaminyl cyclases unfold glutamyl cyclase activity under mild acid conditions, FEBS Letters, 2004, pp. 191-196, vol. 563.
Schilling et al., On the Seeding and Oligomerization of pGlu-Amyloid Peptides (in vitro), Biochemistry, 2006, pp. 12393-12399, vol. 45, No. 41.
Schilling et al., Isolation and characterization of the glutaminyl cyclases from *Solanum tuberosum* and *Arabidopsis thaliana*: implications for physiological functions, Biol. Chem., 2007, pp. 145-153, vol. 388.
Selkoe, Alzheimer's Disease: Genes, Proteins, and Therapy, Physiological Reviews, 2001, pp. 741-766, vol. 81, No. 2.
Shin et al., Amyloid β-Protein (Aβ) 1-40 But Not Aβ1-42 Contributes to the Experimental Formation of Alzheimer Disease Amyloid Fibrils in Rat Brain, Journal of Neurosciences, 1997, pp. 8187-8193. vol. 17, No. 21.
Shulman et al., The Challenge of Time: Clock-drawing and Cognitive Function in The Elderly, International Journal of Geriatric Psychiatry, 1986, pp. 135-140, vol. 1.
Thal, et al., Apolipoprotein E co-localizes with newly formed amyloid β-protein (Aβ) deposits lacking immunoreactivity against N-terminal epitopes of Aβ in a genotype-dependent manner, Acta Neuropathol, 2005, pp. 459-471, vol. 110.
Vidal et al., A decamer duplication in the 3' region of the BRI gene originates an amyloid peptide that is associated with dementia in a Danish kindred, Proc. Natl. Acad. Sci., 2000, pp. 4920-4925, vol. 97, No. 9.

* cited by examiner

SEQUENCE LISTING

```
<160> NUMBER OF SEQ ID NOS: 54

<210> SEQ ID NO 1
<211> LENGTH: 42
<212> TYPE: PRT
<213> ORGANISM: Human

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 40
<212> TYPE: PRT
<213> ORGANISM: Human

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30
```

```
Gly Leu Met Val Gly Gly Val Val
        35                  40

<210> SEQ ID NO 3
<211> LENGTH: 38
<212> TYPE: PRT
<213> ORGANISM: Human

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly
        35

<210> SEQ ID NO 4
<211> LENGTH: 40
<212> TYPE: PRT
<213> ORGANISM: Human

<400> SEQUENCE: 4

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
        35                  40

<210> SEQ ID NO 5
<211> LENGTH: 38
<212> TYPE: PRT
<213> ORGANISM: Human

<400> SEQUENCE: 5

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 6
<211> LENGTH: 36
<212> TYPE: PRT
<213> ORGANISM: Human

<400> SEQUENCE: 6

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly
        35

<210> SEQ ID NO 7
<211> LENGTH: 32
<212> TYPE: PRT
<213> ORGANISM: Human

<400> SEQUENCE: 7
```

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val Ile Ala
            20                  25                  30

<210> SEQ ID NO 8
<211> LENGTH: 30
<212> TYPE: PRT
<213> ORGANISM: Human

<400> SEQUENCE: 8

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val
            20                  25                  30

<210> SEQ ID NO 9
<211> LENGTH: 28
<212> TYPE: PRT
<213> ORGANISM: Human

<400> SEQUENCE: 9

Glu Val His His Gln Lys Leu Val Phe Phe Ala Glu Asp Val Gly Ser
1               5                   10                  15

Asn Lys Gly Ala Ile Ile Gly Leu Met Val Gly Gly
            20                  25

<210> SEQ ID NO 10
<211> LENGTH: 13
<212> TYPE: PRT
<213> ORGANISM: Mus musculus

<400> SEQUENCE: 10

Lys Met Asp Ala Glu Phe Arg His Asp Ser Gly Tyr Glu
1               5                   10

<210> SEQ ID NO 11
<211> LENGTH: 13
<212> TYPE: PRT
<213> ORGANISM: Mus musculus

<400> SEQUENCE: 11

Asp Ala Glu Phe Arg His Asp Ser Gly Tyr Glu Val His
1               5                   10

<210> SEQ ID NO 12
<211> LENGTH: 13
<212> TYPE: PRT
<213> ORGANISM: Mus musculus
<220> FEATURE:
<221> NAME/KEY: isoaspartate
<222> LOCATION: (1)..(1)

<400> SEQUENCE: 12

Asp Ala Glu Phe Arg His Asp Ser Gly Tyr Glu Val His
1               5                   10

<210> SEQ ID NO 13
<211> LENGTH: 13
<212> TYPE: PRT
<213> ORGANISM: Mus musculus

<400> SEQUENCE: 13

Ala Glu Phe Arg His Asp Ser Gly Tyr Glu Val His His
1               5                   10

<210> SEQ ID NO 14
<211> LENGTH: 13
<212> TYPE: PRT
<213> ORGANISM: Mus musculus

<400> SEQUENCE: 14

Glu Phe Arg His Asp Ser Gly Tyr Glu Val His His Gln
1               5                   10

<210> SEQ ID NO 15
<211> LENGTH: 13
<212> TYPE: PRT
<213> ORGANISM: Mus musculus
<220> FEATURE:
<221> NAME/KEY: pyroglutamate
<222> LOCATION: (1)..(1)

<400> SEQUENCE: 15

Glu Phe Arg His Asp Ser Gly Tyr Glu Val His His Gln
1               5                   10

<210> SEQ ID NO 16
<211> LENGTH: 13
<212> TYPE: PRT
<213> ORGANISM: Mus musculus

<400> SEQUENCE: 16

Phe Arg His Asp Ser Gly Tyr Glu Val His His Gln Lys
1               5                   10

<210> SEQ ID NO 17
<211> LENGTH: 13
<212> TYPE: PRT
<213> ORGANISM: Mus musculus

<400> SEQUENCE: 17

Gly Tyr Glu Val His His Gln Lys Leu Val Phe Phe Ala
1               5                   10

<210> SEQ ID NO 18
<211> LENGTH: 13
<212> TYPE: PRT
<213> ORGANISM: Mus musculus

<400> SEQUENCE: 18

Glu Val His His Gln Lys Leu Val Phe Phe Ala Glu Asp
1               5                   10

<210> SEQ ID NO 19
<211> LENGTH: 13
<212> TYPE: PRT
<213> ORGANISM: Mus musculus
<220> FEATURE:
<221> NAME/KEY: pyroglutamate
<222> LOCATION: (1)..(1)

<400> SEQUENCE: 19

Glu Val His His Gln Lys Leu Val Phe Phe Ala Glu Asp
1               5                   10

<210> SEQ ID NO 20
<211> LENGTH: 13
<212> TYPE: PRT

<213> ORGANISM: Mus musculus

<400> SEQUENCE: 20

Val His His Gln Lys Leu Val Phe Phe Ala Glu Asp Val
1               5                   10

<210> SEQ ID NO 21
<211> LENGTH: 13
<212> TYPE: PRT
<213> ORGANISM: Mus musculus
<220> FEATURE:
<221> NAME/KEY: isoaspartate
<222> LOCATION: (7)..(7)

<400> SEQUENCE: 21

Asp Ala Glu Phe Arg His Asp Ser Gly Tyr Glu Val His
1               5                   10

<210> SEQ ID NO 22
<211> LENGTH: 13
<212> TYPE: PRT
<213> ORGANISM: Mus musculus
<220> FEATURE:
<221> NAME/KEY: isoaspartate
<222> LOCATION: (1)..(1)

<400> SEQUENCE: 22

Asp Ser Gly Tyr Glu Val His His Gln Lys Leu Val Phe
1               5                   10

<210> SEQ ID NO 23
<211> LENGTH: 13
<212> TYPE: PRT
<213> ORGANISM: Mus musculus

<400> SEQUENCE: 23

Leu Val Phe Phe Ala Glu Asp Val Gly Ser Asn Lys Gly
1               5                   10

<210> SEQ ID NO 24
<211> LENGTH: 13
<212> TYPE: PRT
<213> ORGANISM: Mus musculus

<400> SEQUENCE: 24

Gly Ser Asn Lys Gly Ala Ile Ile Gly Leu Met Val Gly
1               5                   10

<210> SEQ ID NO 25
<211> LENGTH: 13
<212> TYPE: PRT
<213> ORGANISM: Mus musculus

<400> SEQUENCE: 25

Ala Ile Ile Gly Leu Met Val Gly Gly Val Val Ile Ala
1               5                   10

<210> SEQ ID NO 26
<211> LENGTH: 30
<212> TYPE: DNA
<213> ORGANISM: Artificial Sequence
<220> FEATURE:
<223> OTHER INFORMATION: PCR Primer

<400> SEQUENCE: 26
atgaagttgc ctgttaggct gttggtgctg                                    30

<210> SEQ ID NO 27
<211> LENGTH: 30
<212> TYPE: DNA
<213> ORGANISM: Artificial Sequence
<220> FEATURE:
<223> OTHER INFORMATION: PCR Primer

<400> SEQUENCE: 27
atggagwcag acacactcct gytatgggtg                                    30

<210> SEQ ID NO 28
<211> LENGTH: 30
<212> TYPE: DNA
<213> ORGANISM: Artificial Sequence
<220> FEATURE:
<223> OTHER INFORMATION: PCR Primer

<400> SEQUENCE: 28
atgagtgtgc tcactcaggt cctggsgttg                                    30

<210> SEQ ID NO 29
<211> LENGTH: 33
<212> TYPE: DNA
<213> ORGANISM: Artificial Sequence
<220> FEATURE:
<223> OTHER INFORMATION: PCR Primer

<400> SEQUENCE: 29
atgaggrccc ctgctcagwt tyttggmwtc ttg                                33

<210> SEQ ID NO 30
<211> LENGTH: 30
<212> TYPE: DNA
<213> ORGANISM: Artificial Sequence
<220> FEATURE:
<223> OTHER INFORMATION: PCR Primer

<400> SEQUENCE: 30
atggatttwc aggtgcagat twtcagcttc                                    30

<210> SEQ ID NO 31
<211> LENGTH: 27
<212> TYPE: DNA
<213> ORGANISM: Artificial Sequence
<220> FEATURE:
<223> OTHER INFORMATION: PCR Primer

<400> SEQUENCE: 31
atgaggtkcy ytgytsagyt yctgrgg                                       27

<210> SEQ ID NO 32
<211> LENGTH: 31
<212> TYPE: DNA
<213> ORGANISM: Artificial Sequence
<220> FEATURE:
<223> OTHER INFORMATION: PCR Primer

<400> SEQUENCE: 32
atgggcwtca agatggagtc acakwyycwg g                                  31

<210> SEQ ID NO 33
<211> LENGTH: 31
<212> TYPE: DNA
<213> ORGANISM: Artificial Sequence
<220> FEATURE:

<223> OTHER INFORMATION: PCR Primer

<400> SEQUENCE: 33 atgtgggay ctktttycmm tttttcaatt g         31

<210> SEQ ID NO 34
<211> LENGTH: 25
<212> TYPE: DNA
<213> ORGANISM: Artificial Sequence
<220> FEATURE:
<223> OTHER INFORMATION: PCR Primer

<400> SEQUENCE: 34
atggtrtccw casctcagtt ccttg         25

<210> SEQ ID NO 35
<211> LENGTH: 27
<212> TYPE: DNA
<213> ORGANISM: Artificial Sequence
<220> FEATURE:
<223> OTHER INFORMATION: PCR Primer

<400> SEQUENCE: 35
atgtatatat gtttgttgtc tatttct         27

<210> SEQ ID NO 36
<211> LENGTH: 28
<212> TYPE: DNA
<213> ORGANISM: Artificial Sequence
<220> FEATURE:
<223> OTHER INFORMATION: PCR Primer

<400> SEQUENCE: 36
atggaagccc cagctcagct tctcttcc         28

<210> SEQ ID NO 37
<211> LENGTH: 20
<212> TYPE: DNA
<213> ORGANISM: Artificial Sequence
<220> FEATURE:
<223> OTHER INFORMATION: PCR Primer

<400> SEQUENCE: 37
actggatggt gggaagatgg         20

<210> SEQ ID NO 38
<211> LENGTH: 27
<212> TYPE: DNA
<213> ORGANISM: Artificial Sequence
<220> FEATURE:
<223> OTHER INFORMATION: PCR Primer

<400> SEQUENCE: 38
atgaaatgca gctggggcat sttcttc         27

<210> SEQ ID NO 39
<211> LENGTH: 26
<212> TYPE: DNA
<213> ORGANISM: Artificial Sequence
<220> FEATURE:
<223> OTHER INFORMATION: PCR Primer

<400> SEQUENCE: 39
atgggatgga gctrtatcat sytctt         26

```
<210> SEQ ID NO 40
<211> LENGTH: 27
<212> TYPE: DNA
<213> ORGANISM: Artificial Sequence
<220> FEATURE:
<223> OTHER INFORMATION: PCR Primer

<400> SEQUENCE: 40
atgaagwtgt ggttaaactg ggttttt                                    27

<210> SEQ ID NO 41
<211> LENGTH: 25
<212> TYPE: DNA
<213> ORGANISM: Artificial Sequence
<220> FEATURE:
<223> OTHER INFORMATION: PCR Primer

<400> SEQUENCE: 41
atgractttg ggytcagctt grttt                                      25

<210> SEQ ID NO 42
<211> LENGTH: 30
<212> TYPE: DNA
<213> ORGANISM: Artificial Sequence
<220> FEATURE:
<223> OTHER INFORMATION: PCR Primer

<400> SEQUENCE: 42
atggactcca ggctcaattt agttttcctt                                 30

<210> SEQ ID NO 43
<211> LENGTH: 28
<212> TYPE: DNA
<213> ORGANISM: Artificial Sequence
<220> FEATURE:
<223> OTHER INFORMATION: PCR Primer

<400> SEQUENCE: 43
atggcttgtc ytrgsgctrc tcttctgc                                   28

<210> SEQ ID NO 44
<211> LENGTH: 26
<212> TYPE: DNA
<213> ORGANISM: Artificial Sequence
<220> FEATURE:
<223> OTHER INFORMATION: PCR Primer

<400> SEQUENCE: 44
atggratgga gckggrtctt tmtctt                                     26

<210> SEQ ID NO 45
<211> LENGTH: 23
<212> TYPE: DNA
<213> ORGANISM: Artificial Sequence
<220> FEATURE:
<223> OTHER INFORMATION: PCR Primer

<400> SEQUENCE: 45
atgagagtgc tgattctttt gtg                                        23

<210> SEQ ID NO 46
<211> LENGTH: 30
<212> TYPE: DNA
<213> ORGANISM: Artificial Sequence
<220> FEATURE:
<223> OTHER INFORMATION: PCR Primer
```

<400> SEQUENCE: 46
atggmttggg tgtggamctt gctattcctg                                    30

<210> SEQ ID NO 47
<211> LENGTH: 27
<212> TYPE: DNA
<213> ORGANISM: Artificial Sequence
<220> FEATURE:
<223> OTHER INFORMATION: PCR Primer

<400> SEQUENCE: 47
atgggcagac ttacattctc attcctg                                       27

<210> SEQ ID NO 48
<211> LENGTH: 28
<212> TYPE: DNA
<213> ORGANISM: Artificial Sequence
<220> FEATURE:
<223> OTHER INFORMATION: PCR Primer

<400> SEQUENCE: 48
atggattttg ggctgatttt ttttattg                                      28

<210> SEQ ID NO 49
<211> LENGTH: 27
<212> TYPE: DNA
<213> ORGANISM: Artificial Sequence
<220> FEATURE:
<223> OTHER INFORMATION: PCR Primer

<400> SEQUENCE: 49
atgatggtgt taagtcttct gtacctg                                       27

<210> SEQ ID NO 50
<211> LENGTH: 21
<212> TYPE: DNA
<213> ORGANISM: Artificial Sequence
<220> FEATURE:
<223> OTHER INFORMATION: PCR Primer

<400> SEQUENCE: 50
cagtggatag acagatgggg g                                             21

<210> SEQ ID NO 51
<211> LENGTH: 441
<212> TYPE: DNA
<213> ORGANISM: Mus musculus

<400> SEQUENCE: 51
atggagtcac atacccaggt tcttatattg ctgctgctat gggtatctgg tacctgtggg    60
gacattgtga tgtcacagtc tccatcctcc ctggctgtgt cagcaggaga gaaggtcact   120
atgagctgca aatccagtca gagtctgttc tacagtagaa cccgaaagaa ctacttggct   180
tggtaccaac agaaaccagg gcagtctcct aaattgctga tctactgggc atccactagg   240
gaatctgggg tccctgatcg cttcacaggc agtggatctg gacagatttt cactctcacc   300
atcagcagtg tgcaggctga agacctggca gtttattact gcaagcaatc ttacaatctg   360
tggtcgttcg gtggaggcac caagctggaa atcaaacggg ctgatgctgc accaactgta   420
tccatcttcc caccatccag t                                            441

<210> SEQ ID NO 52
<211> LENGTH: 147

```
<212> TYPE: PRT
<213> ORGANISM: Mus musculus

<400> SEQUENCE: 52

Met Glu Ser His Thr Gln Val Leu Ile Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Phe Tyr Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Trp Ser Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser
145

<210> SEQ ID NO 53
<211> LENGTH: 447
<212> TYPE: DNA
<213> ORGANISM: Mus musculus

<400> SEQUENCE: 53
atgggatgga gctgtatcat gttcttttg gtagcaacag ctacagatgt ccactcccag      60
gtccaactgc agcagcctgg gactgaactg gtgaagcctg ggcttcagt gaagctgtcc     120 tgcaaggctt ctggcttcac cttcaccagc tactggatgc actgggtgag acagaggcct    180
ggacaaggcc ttgagtggat tggagagatt aatcctagta cggtcgtac taactataat    240 gagaagttca agagcaaggc cacactgact gtagacaaat cctccagcac agcctacatg    300
caactcagca gcctgacatc tgaggactct gaggtctatt actgtgcgag aggggatctt    360
gcctgggact ggtctgctta ctggggccaa gggactctgg tcactgtctc tgcagccaaa    420
acgacacccc catctgtcta tccactg                                        447

<210> SEQ ID NO 54
<211> LENGTH: 149
<212> TYPE: PRT
<213> ORGANISM: Mus musculus
<220> FEATURE:
<221> NAME/KEY: misc_feature
<222> LOCATION: (8)..(8)
<223> OTHER INFORMATION: Xaa can be any naturally occurring amino acid

<400> SEQUENCE: 54

Met Gly Trp Ser Cys Ile Met Xaa Phe Leu Val Ala Thr Ala Thr Asp
1               5                   10                  15

Val His Ser Gln Val Gln Leu Gln Gln Pro Gly Thr Glu Leu Val Lys
            20                  25                  30

Pro Gly Ala Ser Val Lys Leu Ser Cys Lys Ala Ser Gly Phe Thr Phe
        35                  40                  45
```

```
Thr Ser Tyr Trp Met His Trp Val Arg Gln Arg Pro Gly Gln Gly Leu
    50              55                  60

Glu Trp Ile Gly Glu Ile Asn Pro Ser Asn Gly Arg Thr Asn Tyr Asn
65              70                  75                      80

Glu Lys Phe Lys Ser Lys Ala Thr Leu Thr Val Asp Lys Ser Ser Ser
            85                  90              95

Thr Ala Tyr Met Gln Leu Ser Ser Leu Thr Ser Glu Asp Ser Glu Val
            100             105                 110

Tyr Tyr Cys Ala Arg Gly Asp Leu Ala Trp Asp Trp Ser Ala Tyr Trp
        115             120             125

Gly Gln Gly Thr Leu Val Thr Val Ser Ala Ala Lys Thr Thr Pro Pro
    130             135             140

Ser Val Tyr Pro Leu
145
```

DIAGNOSTIC ANTIBODY ASSAY

CROSS-REFERENCE TO RELATED APPLICATIONS

This application claims priority from U.S. Non Provisional application Ser. No. 13/422,583, filed 16 Mar. 2012, which claims priority to U.S. Provisional Application Ser. No. 61/453,449, filed on Mar. 16, 2011, both of which are incorporated herein by reference in their entireties.

MATERIAL INCORPORATED-BY-REFERENCE

The Sequence Listing, which is a part of the present disclosure, includes a computer readable form comprising nucleotide and/or amino acid sequences of the present disclosure. The subject matter of the Sequence Listing is incorporated herein by reference in its entirety.

DEPOSITED BIOLOGICAL MATERIAL

The following biological material, which is a part of the present disclosure, has been deposited in accordance with the Budapest Treaty and are available at the Deutsche Sammlung für Mikroorganismen and Zellkulturen (DSMZ) (German Collection of Microorganisms and Cell Cultures) GmbH, Inhoffenstrasse 7B, 38124 Braunschweig, Germany, with a deposit date of 14 Dec. 2010, and with the respective deposit number DSM ACC 3100.

BACKGROUND OF THE INVENTION

The present disclosure pertains to novel diagnostic assays for the diagnosis of amyloidosis, a group of disorders and abnormalities associated with amyloid protein such as Alzheimer's disease and related aspects. In particular, an antibody assay is provided.

Amyloidosis is not a single disease entity but rather a diverse group of progressive disease processes characterized by extracellular tissue deposits of a waxy, starch-like protein called amyloid, which accumulates in one or more organs or body systems. As the amyloid deposits accumulate, they begin to interfere with the normal function of the organ or body system. There are at least 15 different types of amyloidosis. The major forms are primary amyloidosis without known antecedent, secondary amyloidosis following some other condition, and hereditary amyloidosis.

Secondary amyloidosis occurs during chronic infection or inflammatory disease, such as tuberculosis, a bacterial infection called familial Mediterranean fever, bone infections (osteomyelitis), rheumatoid arthritis, inflammation of the small intestine (granulomatous ileitis), Hodgkin's disease and leprosy.

Amyloid deposits include amyloid P (pentagonal) component (AP), a glycoprotein related to normal serum amyloid P (SAP), and sulphated glycosaminoglycans (GAG), complex carbohydrates of connective tissue. Amyloid protein fibrils, which account for about 90% of the amyloid material, comprise one of several different types of proteins. These proteins are capable of folding into so-called "beta-pleated" sheet fibrils, a unique protein configuration which exhibits binding sites for Congo red resulting in the unique staining properties of the amyloid protein.

Many diseases of aging are based on or associated with amyloid-like proteins and are characterized, in part, by the buildup of extracellular deposits of amyloid or amyloid-like material that contribute to the pathogenesis, as well as the progression of the disease. These diseases include, but are not limited to, neurological disorders such as mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome, Lewy body dementia, hereditary cerebral hemorrhage with amyloidosis (Dutch type); the Guam Parkinson-Dementia complex. Other diseases which are based on or associated with amyloid-like proteins are progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration.

Although pathogenesis of these diseases may be diverse, their characteristic deposits often contain many shared molecular constituents. To a significant degree, this may be attributable to the local activation of pro-inflammatory pathways thereby leading to the concurrent deposition of activated complement components, acute phase reactants, immune modulators, and other inflammatory mediators (McGeer et al., Tohoku J Exp Med. 174(3): 269-277 (1994)).

Recently, accumulating evidence demonstrates involvement of N-terminal modified Aβ peptide variants in Alzheimer's disease. Aiming biopsies display a presence of Aβ 1-40 and Aβ 1-42 not only in the brain of Alzheimer's patients but also in senile plaques of unaffected individuals. However, N-terminal truncated and pyroGlu modified Aβ N3pE-40/Aβ N3pE-42 is almost exclusively engrained within plaques of Alzheimer's disease patients, making this Aβ variant an eligible diagnostic marker and a potential target for drug development.

At present, several commercial manufacturers offer ELISA kits which allow a detection of Aβ 1-40/1-42 and Aβ N3pE-40/Aβ N3pE-42 in the low picogram (pg) range.

The brains of Alzheimer's disease (AD) patients are morphologically characterized by the presence of neurofibrillary tangles and by deposits of Aβ peptides in neocortical brain structures (Selkoe, D. J. & Schenk, D. Alzheimer's disease: molecular understanding predicts amyloid-based therapeutics. Annu. Rev. Pharmacol. Toxicol. 43, 545-584 (2003)). Aβ peptides are liberated from the amyloid precursor protein (APP) after sequential cleavage by β- and γ-secretase. The γ-secretase cleavage results in the generation of Aβ 1-40 and Aβ 1-42 peptides, which differ in their C-termini and exhibit different potencies of aggregation, fibril formation and neurotoxicity (Shin, R. W. et al. Amyloid beta-protein (Abeta) 1-40 but not Abeta 1-42 contributes to the experimental formation of Alzheimer disease amyloid fibrils in rat brain. J. Neurosci. 17, 8187-8193 (1997); Iwatsubo, T. et al. Visualization of Abeta 42(43) and Abeta 40 in senile plaques with end-specific Abeta monoclonals: evidence that an initially deposited species is Abeta 42(43). Neuron 13, 45-53 (1994); Iwatsubo, T., Mann, D. M., Odaka, A., Suzuki, N. & Ihara, Y. Amyloid beta protein (Abeta) deposition: Abeta 42(43) precedes Abeta 40 in Down syndrome. Ann. Neurol. 37, 294-299 (1995); Hardy, J. A. & Higgins, G. A. Alzheimer's disease: the amyloid cascade hypothesis. Science 256, 184-185 (1992); Roβner, S., Ueberham, U., Schliebs, R., Perez-Polo, J. R. & Bigl, V. The regulation of amyloid precursor protein metabolism by cholinergic mechanisms and neurotrophin receptor signaling. Prog. Neurobiol. 56, 541-569 (1998)).

The majority of Aβ peptides deposited in diffuse plaques are N-terminal truncated or modified. Studies of Piccini and Saido have shown that the core structure of senile plaques and vascular deposits consist of 50% pyroglutamate (pyro-Glu) modified peptides (Piccini et al., J Biol Chem. 2005 Oct. 7; 280(40):34186-92; Saido et al., Neuron. 1995 February; 14(2): 457-66). PyroGlu modified peptides are more strongly cytotoxic than other Aβ species and stable against aminopeptidases (Russo et al., J Neurochem. 2002 September; 82(6):1480-9). Thus, pyroGluAβ species have a longer half life whereby the accumulation of these species and the formation of neurotoxic oligomers as well as aggregates are beneficial (Saido, Neurobiol Aging. 1998 January-February; 19(1 Suppl):S69-75). Due to the cyclization of glutamate to pyroGlu, charged amino acids will be lost which strongly reduces the solubility of the peptide and causes an increased aggregation tendency. In vitro studies have shown that the initial oligomerisation of e.g. Aβ3(pE) is much faster compared to non-modified peptides (Schilling et al., Biochemistry. 2006 Oct. 17; 45(41):12393-9).

Studies conducted by the Applicants have showed that Aβ11(pE) has a higher aggregation potency and a much lower solubility than Aβ3(pE). The group of Näslund J. et al. (Proc. Natl. Acad. Sci. Neurobiology, Vol. 91 pp. 8378-8382) detected by mass spectrometry the most prominent truncated variant AβpE(11-42) in brains of sporadic AD. Up to now the study of Näslund J. et al. is one of the few studies that examined the deposition of Aβ11(pE) in plaques.

All facts suggest that pyroGlu Aβ is a kind of germ for the initialization of fibril formation. In a new study (Piccini et al., 2005, supra) volunteers with plaque depositions but without AD specific pathology could be distinguished from AD patients due to the characteristic amount of Aβ-species. Thereby the amount of N-terminal truncated, pyroGlu modified peptides was significant higher in the brain of AD patients.

The posttranslational formation of pyroGlu at position 3 or 11 of Aβ-peptide implies cyclization of an N-terminal glutamate residue. Glutaminyl cyclase (QC) plays an important role in the generation of pyroGlu peptides. QC is wide-spread in the plant- and animal kingdom and inter alia, is involved in the maturation of peptide hormones. Both the cyclisation of glutamine by release of ammonia and of glutamate by release of water to pyroGlu is performed by QC. In contrast to the glutamine cyclization the glutamate cyclisation occurs not spontaneously. QC catalyses the efficient (unwanted) side reaction from glutamate to pyroGlu. The generated pyroGlu residue protects the protein against proteolytic degradation. There are several references which shows that QC plays an important role in the generation of pyroGlu Aβ:

1. In several studies it was shown that QC catalyses the formation of pyroGlu residues from glutamate at N-terminus of Aβ (Cynis et al., Biochim Biophys Acta. 2006 October; 1764(10):1618-25, Schilling et al., FEBS Lett. 2004 Apr. 9; 563(1-3):191-6);

2. Both Aβ peptides and QC are expressed in large quantities in hippocampus and cortex. These brain areas are at particular risk in AD (Pohl et al., Proc Natl Acad Sci USA. 1991 Nov. 15; 88(22):10059-63, Selkoe, Physiol Rev. 2001 April; 81(2):741-66);

3. The APP is cleaved by β-secretase during the transport to the plasma membrane whereby the N-terminus of Aβ with the free glutamate residue can be produced (Greenfield et al., Proc Natl Acad Sci USA. 1999 Jan. 19; 96(2):742-7). In the secretory vesicles a co-localisation of processed APP and the QC was determined. So in the mild acid milieu of the vesicles an accelerated modification of glutamate residue to pyroglutamate can occur.

4. Also other neurodegeneratuve disease's (familiar Danish (FDD) or British dementia (FBD)) are related with N-terminal pyroGlu modified peptides e.g. Bri2, but in contrast they are not related to Aβ in terms of their primary structure (Vidal R. et al., 1999 Proc. Natl. Acad. Sci. U.S.A. 97, 4920-4925).

Possibly the QC-catalysed formation of pyroGlu Aβ is involved in the development and progression of neurodegenerative diseases. The formation of N-terminal modified amyloid peptides certainly represents a fundamental factor in the process of Aβ aggregation and could be the onset of disease. The suppression of the pyroGlu Aβ formation by inhibition of QC, might represent a therapeutic approach. QC inhibitors would be able to prevent the formation of pyroGlu Aβ, reduce the concentration of pyroglutamate Aβ in the brain and so delay the oligomerisation of Aβ-peptides. Schilling et al. show, that QC expression was up regulated in the cortex of Aβ patients and correlated with the appearance of pyroGlu-modified Aβ-peptide. Oral application of a QC inhibitor resulted in reduced pyroglutamate modified AβpE(3-42) level in two different transgenic mouse models of AD and in a new *Drosophila* model (Schilling et al., 2008 *Biol. Chem.* (389), 983-991).

Lewy body dementia (LBD) is a neurodegenerative disorder that can occur in persons older than 65 years of age, and typically causes symptoms of cognitive (thinking) impairment and abnormal behavioral changes. Symptoms can include cognitive impairment, neurological signs, sleep disorder, and autonomic failure. Cognitive impairment is the presenting feature of LBD in most cases. Patients have recurrent episodes of confusion that progressively worsen. The fluctuation in cognitive ability is often associated with shifting degrees of attention and alertness. Cognitive impairment and fluctuations of thinking may vary over minutes, hours, or days. Lewy bodies are formed from phosphorylated and nonphosphorylated neurofilament proteins; they contain the synaptic protein alpha-synuclein as well as ubiquitin, which is involved in the elimination of damaged or abnormal proteins. In addition to Lewy Bodies, Lewy neurites, which are inclusion bodies in the cell processes of the nerve cells, may also be present. Amyloid plaques may form in the brains of patients afflicted with DLB, however they tend to be fewer in number than seen in patients with Alzheimer's disease. Neurofibrillary tangles, the other micropathological hallmark of AD, are not a main characteristic of LBD but are frequently present in addition to amyloid plaques.

Amyotrophic lateral sclerosis (ALS) is characterized by degeneration of upper and lower motor neurons. In some ALS patients, dementia or aphasia may be present (ALS-D). The dementia is most commonly a frontotemporal dementia (FTD), and many of these cases have ubiquitin-positive, tau-negative inclusions in neurons of the dentate gyrus and superficial layers of the frontal and temporal lobes.

Inclusion-body myositis (IBM) is a crippling disease usually found in people over age 50, in which muscle fibers develop inflammation and begin to atrophy—but in which the brain is spared and patients retain their full intellect. Two enzymes involved in the production of amyloid-β protein were found to be increased inside the muscle cells of patients with this most common, progressive muscle disease of older people, in which amyloid-β is also increased.

Another disease that is based on or associated with the accumulation and deposit of amyloid-like protein is macular degeneration. Macular degeneration is a common eye disease that causes deterioration of the macula, which is the central area of the retina (the paper-thin tissue at the back of the eye where light-sensitive cells send visual signals to the brain). Sharp, clear, "straight ahead" vision is processed by the macula. Damage to the macula results in the development of blind spots and blurred or distorted vision. Age-related macular degeneration (AMD) is a major cause of visual impairment in the United States and for people over age 65 it is the leading cause of legal blindness among Caucasians. Approximately 1.8 million Americans of age 40 and older have advanced AMD, and another 7.3 million people with intermediate AMD are at substantial risk for vision loss. The government estimates that by 2020 there will be 2.9 million people with advanced AMD. Victims of AMD are often surprised and frustrated to find out how little is known about the causes and treatment of this blinding condition.

There are two forms of macular degeneration: dry macular degeneration and wet macular degeneration. The dry form, in which the cells of the macula slowly begin to break down, is diagnosed in 85 percent of macular degeneration cases. Both eyes are usually affected by dry AMD, although one eye can lose vision while the other eye remains unaffected. Drusen, which are yellow deposits under the retina, are common early signs of dry AMD. The risk of developing advanced dry AMD or wet AMD increases as the number or size of the drusen increases. It is possible for dry AMD to advance and cause loss of vision without turning into the wet form of the disease; however, it is also possible for early-stage dry AMD to suddenly change into the wet form.

The wet form, although it only accounts for 15 percent of the cases, results in 90 percent of the blindness, and is considered advanced AMD (there is no early or intermediate stage of wet AMD). Wet AMD is always preceded by the dry form of the disease. As the dry form worsens, some people begin to have abnormal blood vessels growing behind the macula. These vessels are very fragile and will leak fluid and blood (hence 'wet' macular degeneration), causing rapid damage to the macula.

The dry form of AMD will initially often cause slightly blurred vision. The center of vision in particular may then become blurred and this region grows larger as the disease progresses. No symptoms may be noticed if only one eye is affected. In wet AMD, straight lines may appear wavy and central vision loss can occur rapidly.

Diagnosis of macular degeneration typically involves a dilated eye exam, visual acuity test, and a viewing of the back of the eye using a procedure called fundoscopy to help diagnose AMD, and—if wet AMD is suspected—fluorescein angiography may also be performed. If dry AMD reaches the advanced stages, there is no current treatment to prevent vision loss. However, a specific high dose formula of antioxidants and zinc may delay or prevent intermediate AMD from progressing to the advanced stage. Macugen® (pegaptanib sodium injection), laser photocoagulation and photodynamic therapy can control the abnormal blood vessel growth and bleeding in the macula, which is helpful for some people who have wet AMD; however, vision that is already lost will not be restored by these techniques. If vision is already lost, low vision aids exist that can help improve the quality of life.

One of the earliest signs of age-related macular degeneration (AMD) is the accumulation of extracellular deposits known as drusen between the basal lamina of the retinal pigmented epithelium (RPE) and Bruch's membrane (BM). Recent studies conducted by Anderson et al. have confirmed that drusen contain amyloid beta. (Experimental Eye Research 78 (2004) 243-256).

SUMMARY OF THE INVENTION

At least one aim of the present disclosure is to establish a highly sensitive and concomitantly robust detection technique that allows quantitative determination of Aβ variants, in particular AβpGlu(11-x) peptides, in biological samples, e.g. liquor or serum samples, preferably serum samples. This was a tremendous challenge, given the low abundance of Aβ peptides in blood into account. Having such a detection technique available is, however, a prerequisite for studying efficacy of small molecule inhibitors in drug screening programs.

The present disclosure provides novel methods and compositions comprising highly specific and highly effective antibodies, including chimeric antibodies and fragments thereof, including partially or fully humanized antibodies and fragments thereof, having the ability to specifically recognize and bind to specific epitopes from a range of β-amyloid antigens, in particular AβpGlu(11-x) peptides, which may be presented to the antibody in a monomeric, dimeric, trimeric, etc, or a polymeric form, in form of an aggregate, fibers, filaments or in the condensed form of a plaque. The antibodies described herein are particularly useful for diagnosis of amyloidosis, a group of diseases and disorders associated with amyloid plaque formation including secondary amyloidosis and age-related amyloidosis including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, hereditary cerebral hemorrhage with amyloidosis Dutch type, Parkinson's disease, HIV-related dementia, ALS (amyotropic lateral sclerosis), Adult Onset Diabetes; senile cardiac amyloidosis; endocrine tumors, and others, including macular degeneration, to name just a few.

The present disclosure pertains at least in part to antibodies or variants thereof, which are characterized in that they bind to AβpGlu(11-x) peptides with a high affinity. Said high affinity means in the context of the present disclosure an affinity of a $K_D$ value of $10^{-7}$ M or better, preferably a $K_D$ value of $10^{-8}$ M or better, and even more preferably a $K_D$ value of $10^{-9}$ M-$10^{-12}$ M.

In particular the antibody is preferably a monoclonal antibody and is selected from Aβ13-11-6, hereinafter referred to as clone 13.

The antibody according to the present disclosure is especially useful in a diagnostic method to detect amyloidosis, in particular Alzheimer's disease.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

The sensor chip surface was activated with EDC/NHS at 10 µl/min for 8 min. The ligand immobilization by amine coupling was performed with: A) 10 µg/ml Aβ(pE11-30) in 10 mM $KH_2PO_4$, pH 6 and B) 50 µg/ml Aβ(pE11-30) in 10 mM sodium acetate, pH 5. Peptide was injected with 10 µl/min for 5 min (A) and 20 min (B). Then reactive groups (free esters) were deactivated with 1 M ethanolamine pH 8.5, 10 µl/min for 10 min. Non-immobilized peptides were removed by injection of 0.1 M HCl (3×10 µl) and then the chip was rinsed over night with running buffer. Finally the signal was 1000 RU. The ligand immobilization was performed at Biacore 3000.

Figure 3:
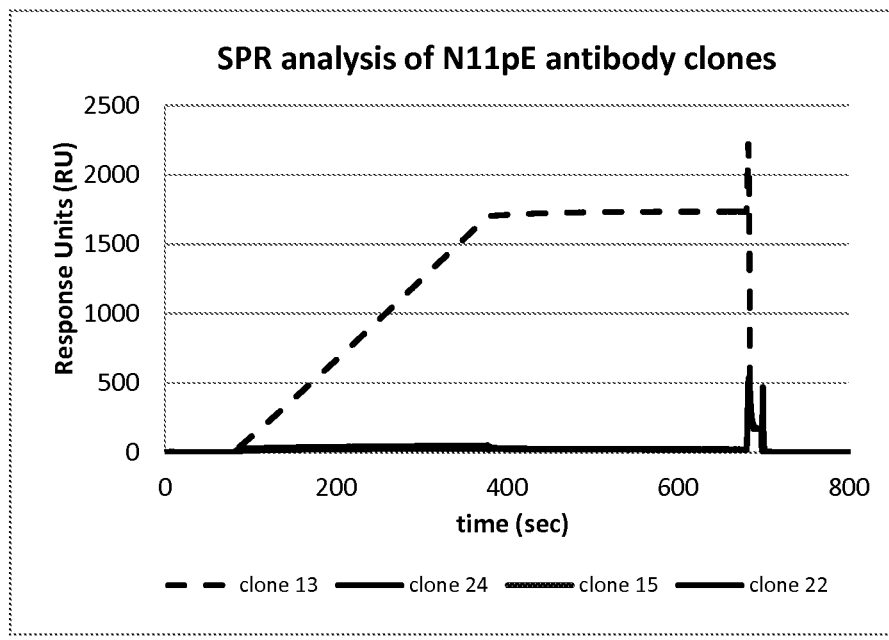

FIG. 3: SPR Measurement of Anti Aβ11(pE) Antibodies

Analyzation of hybridoma cell culture supernatant from clone 13 by Biacore 3000. Usage of CM5 chip with immobilized Aβ(pE11-30), with 1000 RU (flow cell 4). Illustrated is a real-time plot of binding at Aβ(pE11-30) over time. Sample dilution 1:100 in running buffer and injection with 30 µl/min over 300 s and recording of 300 dissociation time. The signal from non-coated flow cell were subtracted from measured signals at flow cell 4 with immobilized Aβ.

Figure 4:
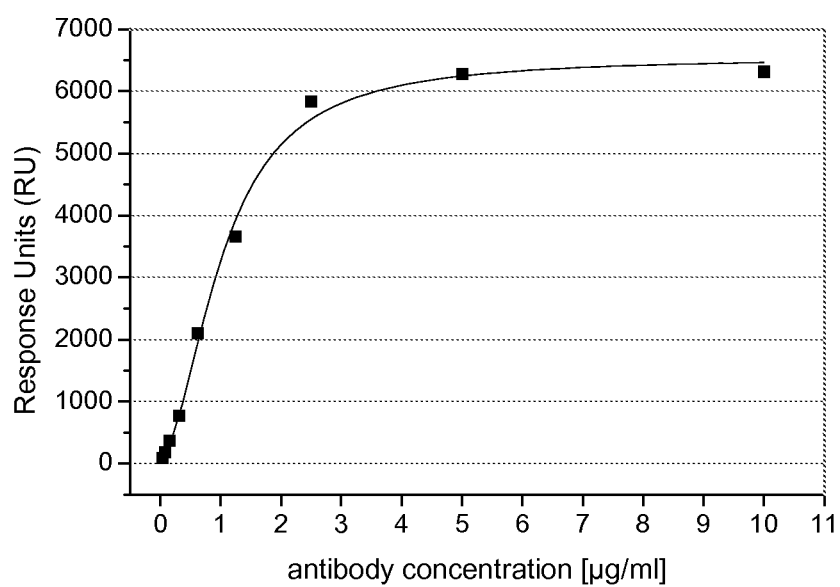

FIG. 4: Curve of Anti Aβ11(pE) Antibody

Purified antibody with concentrations of 0.04-10 µg/ml was measured by SPR at Biacore 3000. The linear range of the curve is from 0.040 µg/ml up to 1.25 µg/ml antibody. Antibody dilution in running buffer and injection with 30 µl/min over 300 s. Each SPR signal was selected from the end of the dissociation phase. The signal from non-coated flow cells were subtracted from measured signals at flow cells with immobilized Aβ.

Figure 5:
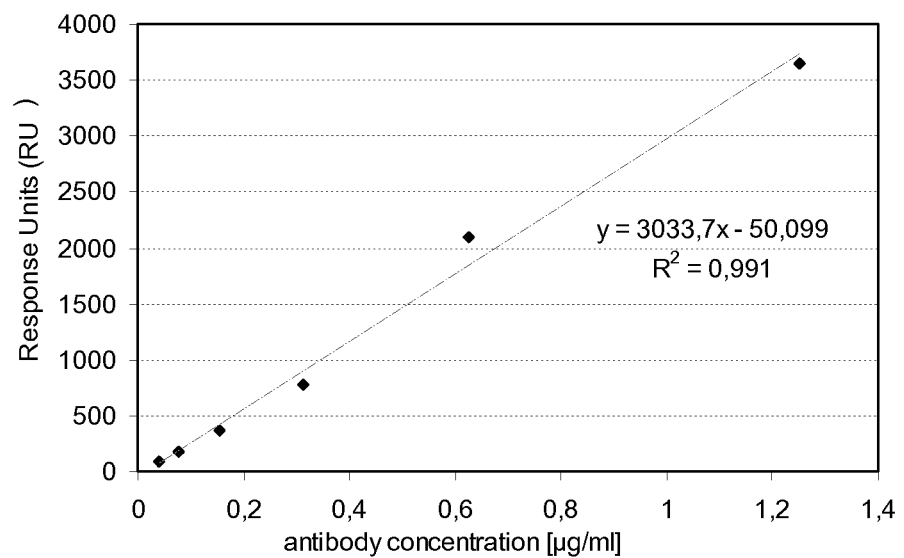

FIG. 5: Standard Curve of Anti Aβ11(pE) Antibody

Purified antibody with known concentrations was measured by SPR at Biacore 3000. Concentration range from 0.040 up to 1.25 µg/ml antibody. Equation of liner regression: y=3033.7x+50.099 ($R^2$=0.991). Each SPR signal was selected from the end of dissociation phase. The signal from non-coated flow cells were subtracted from measured signals at flow cells with immobilized Aβ.

Figure 6:
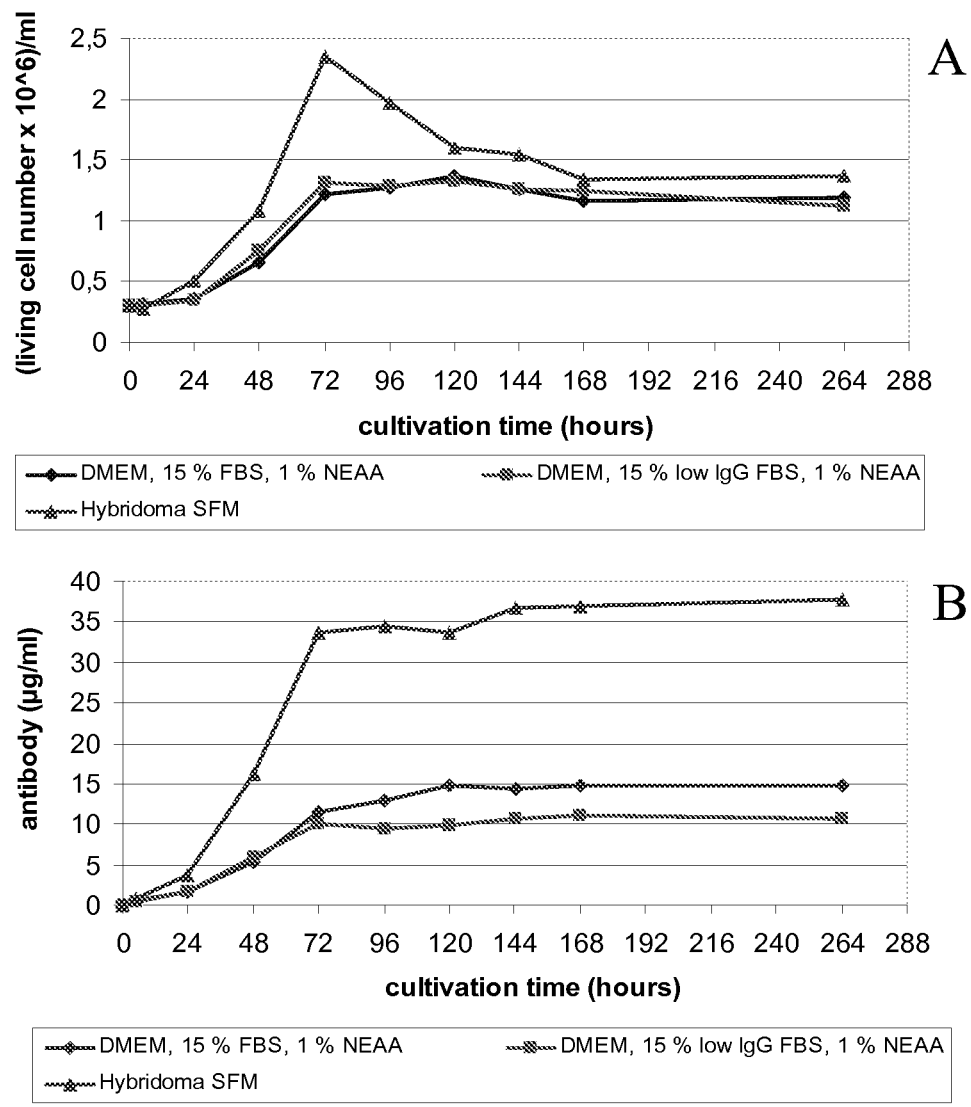

FIG. 6: Comparison of Cell Number and Producing Anti Aβ11(pE) Antibody Concentration Hybridoma cells of clone 13 (cell passage 19) cultivated in serum-containing medium and serum-free medium (Hybridoma SFM) at 37° C. and 5% $CO_2$, supplemented with 2 mM L-glutamine and 50 µM β-mercaptoethanol directly before use. The cells were cultivated for about 10 days in shake flasks and regularly a sample was taken to determine cell growth (A) and antibody concentration (B) by SPR.

Figure 7:
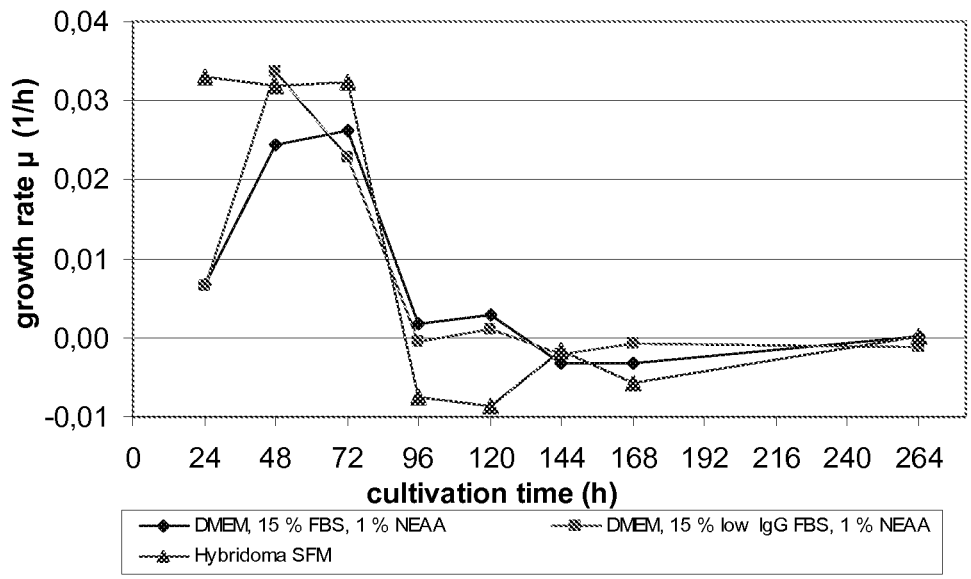

FIG. 7: The Specific Growth Rate µ Dependent on Cultivation Time

Hybridoma cells clone 13 (cell passage 19) cultivated in serum-containing medium and serum-free medium (Hybridoma SFM) at 37° C. and 5% $CO_2$, supplemented with 2 mM L-glutamine and 50 µM β-mercaptoethanol directly before use. The data are based on the growth curve in shake flask over 10 days.

Figure 8:
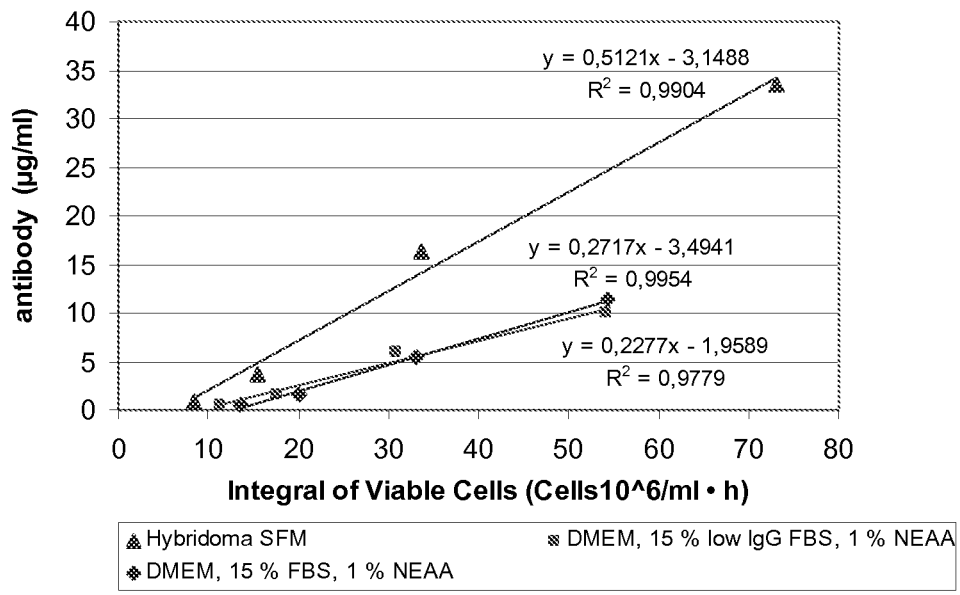

FIG. 8: The Concentration of Anti Aβ11(pE) was Plotted Against the Integral of Viable Cells Hybridoma cells clone 13 (cell passage 19) cultivated in serum-containing medium and serum-free medium (Hybridoma SFM) at 37° C. and 5% $CO_2$, supplemented with 2 mM L-glutamine and 50 µM β-mercaptoethanol. The data are based on the growth curve in shake flasks over 10 days. The integral of viable cells were obtained from the plot of cell number dependent on time, whereby the data points at 5, 24, 48, 72 h were integrated. The antibody productivity rates are obtained from the slope of the curves (see linear functions). $R^2$=coefficient of determination.

Figure 9:
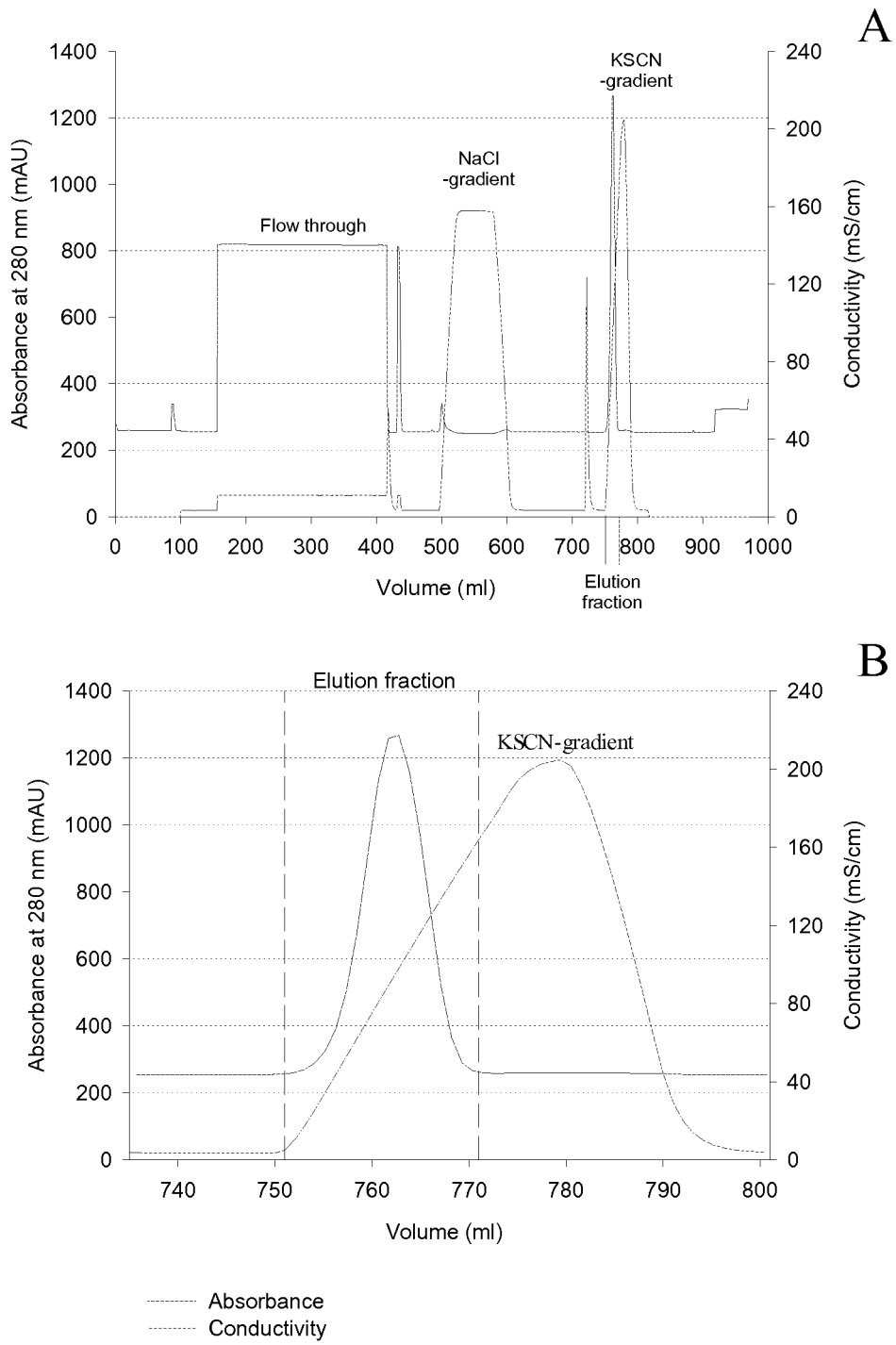

FIG. 9: Chromatogram of Anti Aβ11(pE) Purification 1800 ml hybridoma (clone 13) cell culture supernatant with protein G HP column (V=5 ml) at Äkta™Purifier were purified. The column was cooled at 4° C., equilibrated with 1× binding buffer (20 mM $Na_2HPO_4$, pH 7.0). Centrifugation of cell culture supernatant at 38400×g at 4° C., 30 min, mixed 1:1 with 2× binding buffer. Usage of Äkta™Purifiers P-950 pump. Application of culture supernatant (ice cooled) with 1.5 ml/min. A) Chromatogram with absorbance at 280 nm and conductivity during the purification process. Washing with 0-2 M NaCl-gradient over column volumes then washing with 1× binding buffer again. Elution with 0-2 M KSCN-gradient (pH 7.0) over 5 column volumes with reverse flow of 2.5 ml/min. B) Higher magnification of 0-2 M KSCN-gradient and the elution fraction V=20 ml. The indicated volume is the technical system flow, not the real volume.

Figure 10:
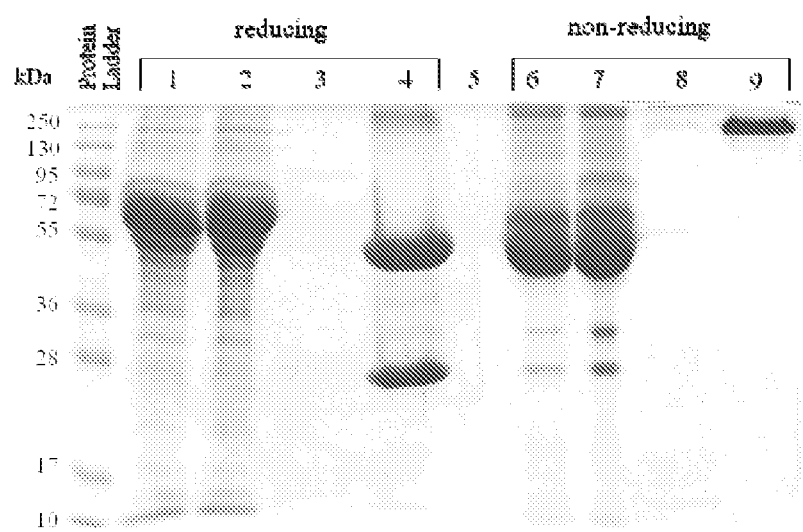

FIG. 10: SDS-Gel-Electropherogram of Anti Aβ11(pE) Antibody (Clone 13) Purification Pre-stained protein ladder: 10-250 kDa, Fermentas. Analyzed purification fractions: slot 1; 6: before Protein G purification, slot 2; 7: Flow through, slot 3; 8: Wash fraction, slot 4; 9: Elution with KSCN, 30 µg/ml antibody was applied, slot 5: non-reducing sample buffer. Antibody purification was performed with protein G HP column, and elution with 0-2 M KSCN pH 7.0. Reduced samples diluted 1:3 in SDS buffer (Roti®-Load 1, BioRad) with β-mercaptoethanol, incubated 10 min, 95° C. Non reduced samples diluted 1:4 in sample buffer without β-mercaptoethanol, shaked 30 min, 30° C. Separation time of SDS-PAGE (12%, 1 mm SDS-gel):10 min at 100 V, 35 min at 200V. Gel stained with Coomassie Brilliant Blue-G250, destained with 10% acetic acid.

Figure 11:
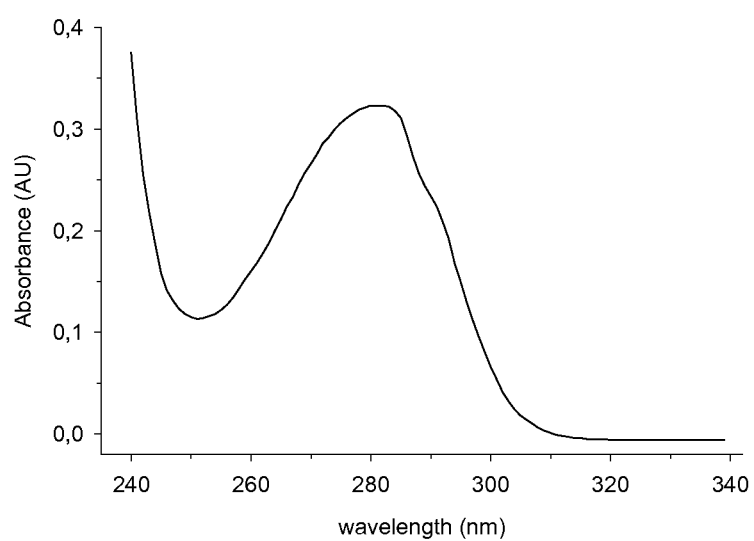

FIG. 11: UV-Spectrum of Anti Aβ11(pE) Antibody

Usage of protein G column purified antibody from hybridoma cell culture supernatant (clone 13). Spectrum measured between 240 nm and 339 nm. Dilution 1:20 in dialysis buffer (D-PBS, 2 mM EDTA, pH 7.13). The thickness of probe was 1 cm and the UV-spectrum between 240 and 339 nm was measured with UV-spectrometer UV1.

Figure 12:
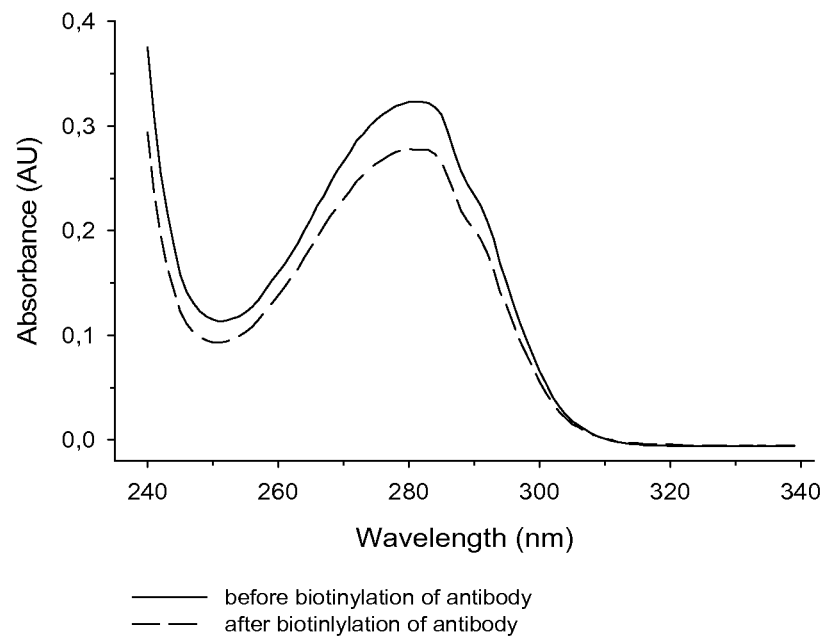

FIG. 12: UV-Spectrum of Anti Aβ11(pE) Antibody

Antibody dilution: 1:10 in D-PBS, 2 mM EDTA. UV-spectrum between 240 nm and 339 nm was measured with the UV-Spectrometer UV1 before and after biotinylation. The thickness of the probe was 1 cm.

Figure 13:
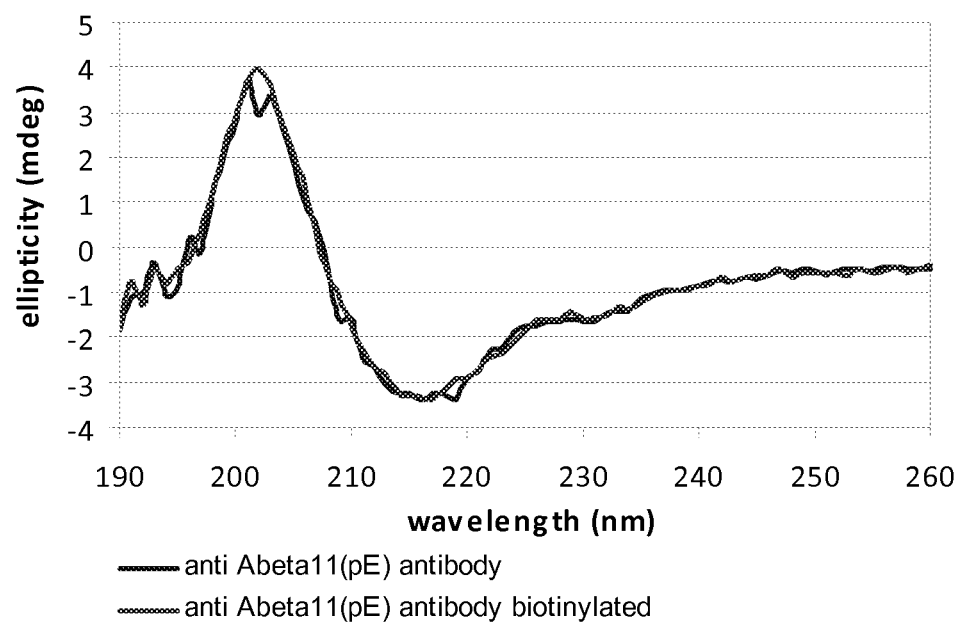

FIG. 13: CD-Spectrum of Anti Aβ11(pE) Antibody

Spectrum of biotinylated and non biotinylated antibody was measured at 20° C. with Jasco J-710 spectro-polarimeter between 190 and 260 nm. The antibody concentration was 0.13 mg/ml in 10 mM $NaH_2PO_4$ (pH 7.1). Measurement with 20 accumulations, 1 s integration and 1 mm thickness of the probe.

Figure 14:
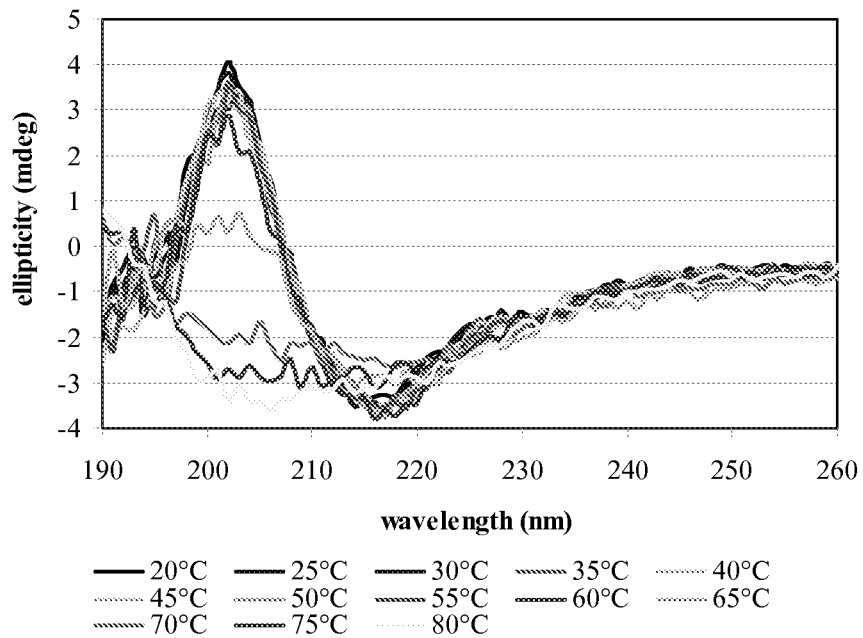

FIG. 14: Thermal Stability of Anti Aβ11(pE) Antibody

The CD-spectrum was measured at temperature from 20° C. up to 80° C. with Jasco J-710 spectro-polarimeter between 190 and 260 nm. The antibody concentrations were 0.13 mg/ml in 10 mM $NaH_2PO_4$ (pH 7.14). Measurement at 5° C. intervals, 10 accumulations with heat rate of 30 K/h, 1 s integration, and 1 mm thickness of the probe Temperature equilibrated 180 s before each measurement.

Figure 15:
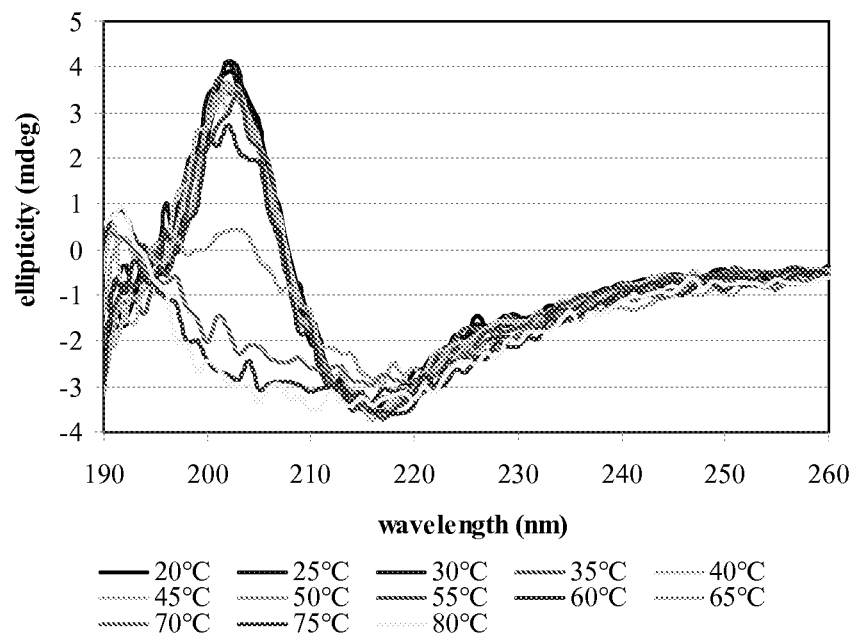

FIG. 15: Thermal Stability of Biotinylated Anti Aβ11(pE) Antibody

The CD-spectrum was measured at temperature from 20° C. up to 80° C. with Jasco J-710 spectro-polarimeter between 190 and 260 nm. The antibody concentrations were 0.13 mg/ml in 10 mM $NaH_2PO_4$ (pH 7.14). Measurement at 5° C. intervals with heat rate of 30 K/h, 10 accumulations, 1 s integration, and 1 mm thickness of the probe temperature, equilibrated 180 s before each measurement.

Figure 16:
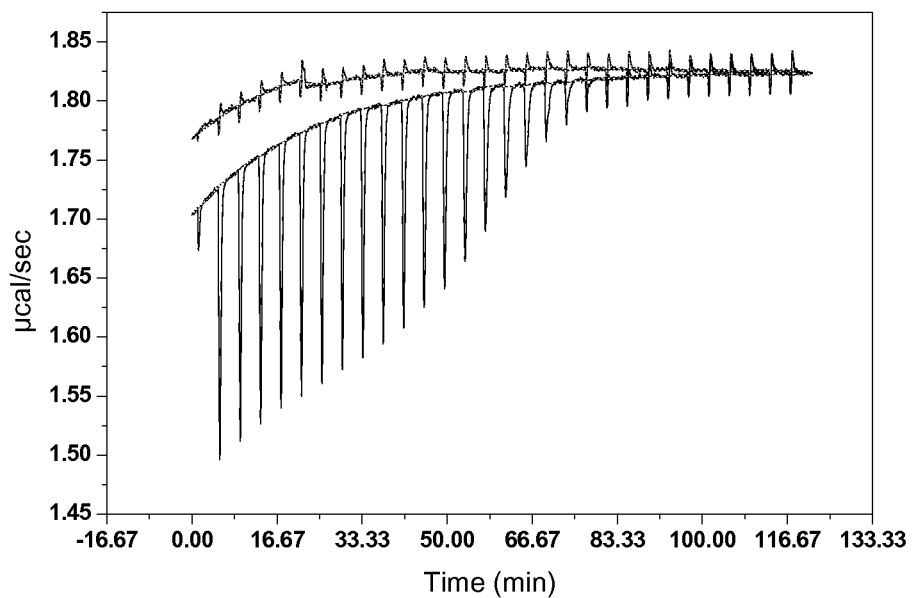

FIG. 16: ITC Titration Curve of Aβ(pE11-18)-PEG at Anti Aβ11(pE) Antibody (clone 13)

Usage of ITC MicroCalorimeter (MicroCal). The experiment consisted of 30 injections (1×2 µl and 29×10 µl) at 20° C. each of 81.78 µM Aβ(pE11-18)-PEG in ITC buffer pH 7.1 with 4-min interval between subsequent injection (black line). The upper trace illustrates the heat of dilution of Aβ(pE11-18)-PEG into ITC buffer. The lower trace illustrates the injection of Aβ(pE11-18)-PEG into sample cell (volume=1.405 ml) containing 5.13 µM antibody in ITC buffer pH 7.1. The red line is the base line.

Figure 17:
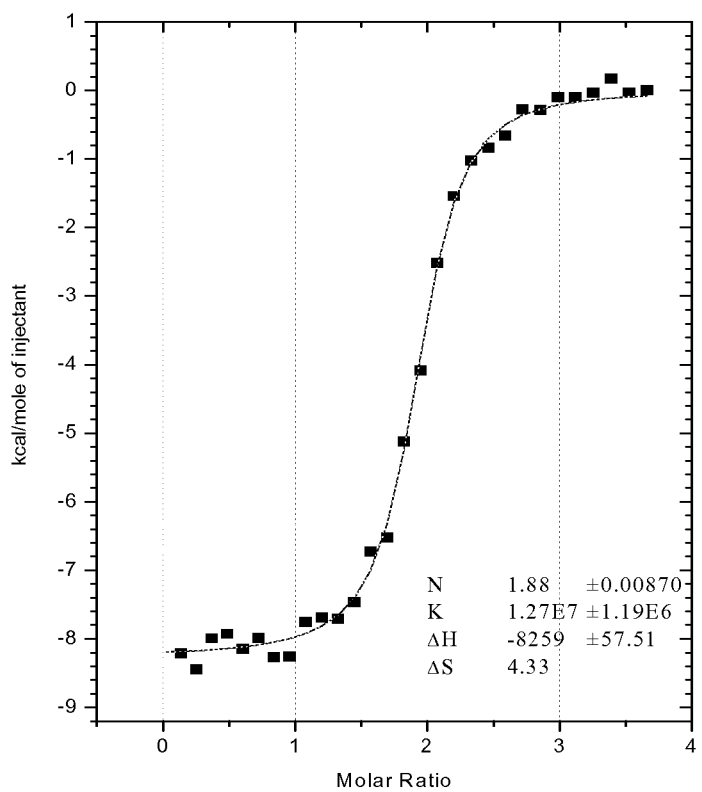

FIG. 17: ITC Binding Curve of Aβ(pE11-18)-PEG at Anti Aβ11(pE) Antibody (Clone 13)

The antibody was purified with protein G sepharose and eluted with KSCN-gradient (pH 7.0). The experiment consisted of 30 injections (1×2 µl and 29×10 µl) at 20° C. each of 81.78 µM Aβ(pE11-18)-PEG in ITC buffer pH 7.1 with 4-min interval between subsequent injection. The sample cell (volume=1.405 ml) containing 5.13 µM antibody in ITC buffer pH 7.1. The heat of dilution of Aβ(pE11-18)-PEG into ITC buffer has been subtracted from all ligand injections. Usage of ITC MicroCalorimeter (MicroCal). Thermodynamic parameters reaction stoichiometry (N), association constant (K), binding enthalpy (ΔH) as well as the entropy (ΔS) was determined with Origin 7.0.

Figure 18:
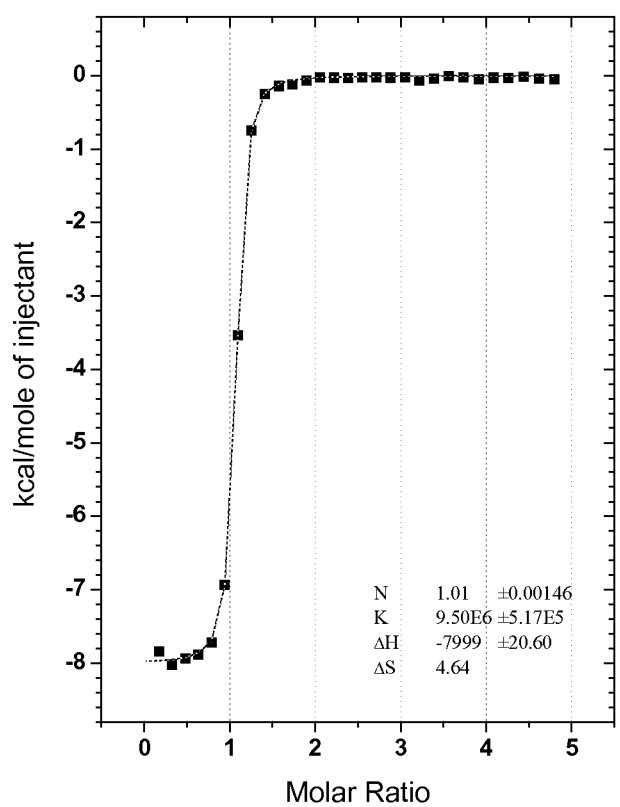

FIG. 18: ITC Binding Curve of Aβ(pE11-18)-PEG at Anti Aβ11(pE) Antibody (Clone 13)

The antibody was purified with protein G sepharose and eluted with 0.1 M glycine-HCl solution (pH 2.7). The experiment consisted of 30 injections (1×2 µl and 29×10 µl) at 20° C. each of 686.31 µM Aβ(pE11-18)-PEG in ITC buffer pH 7.1 with 4-min interval between subsequent injections. The sample cell (volume=1.405 ml) containing 32.85 µM antibody in ITC buffer pH 7.1. The heat of dilution of Aβ(pE11-18)-PEG into ITC buffer has been subtracted from all ligand injections. Usage of ITC MicroCalorimeter (MicroCal). Thermodynamic parameters reaction stoichiometry (N), association constant (K), binding enthalpy (ΔH) as well as the entropy (ΔS) was determined with Origin 7.0.

Figure 19:
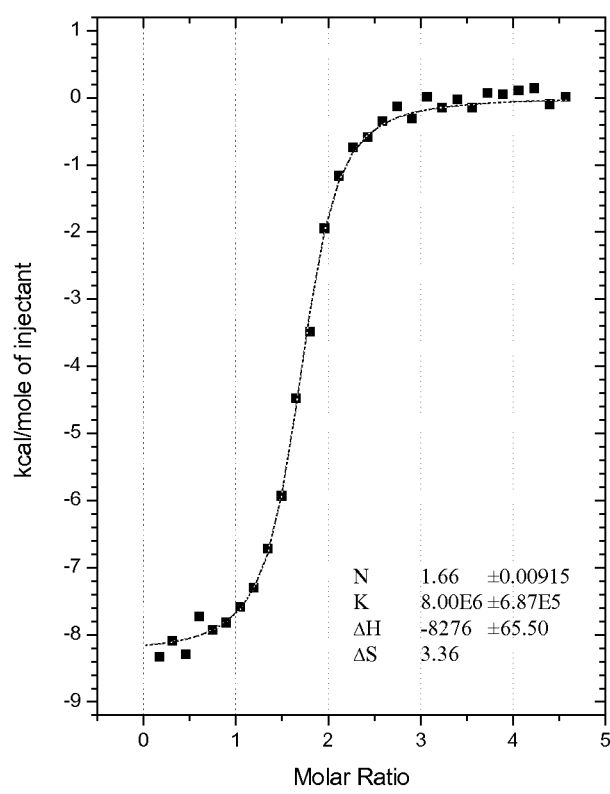

FIG. 19: ITC Binding Curve of Aβ(pE11-18)-PEG at Biotinylated Anti Aβ11(pE) Antibody (Clone 13)

The experiment consisted of 30 injections (1×2 µl and 29×10 µl) at 20° C. each of 101.8 µM Aβ(pE11-18)-PEG in ITC buffer pH 7.1 with 4-min interval between subsequent injections. The sample cell (volume=1.405 ml) containing 5.12 µM biotinylated antibody in ITC buffer pH 7.1. The heat of dilution of Aβ(pE11-18)-PEG into ITC buffer has been subtracted from all ligand injections. Usage of ITC MicroCalorimeter (MicroCal). Thermodynamic parameters reaction stoichiometry (N), association constant (K), binding enthalpy (ΔH) as well as the entropy (ΔS) was determined with Origin 7.0.

Figure 20:
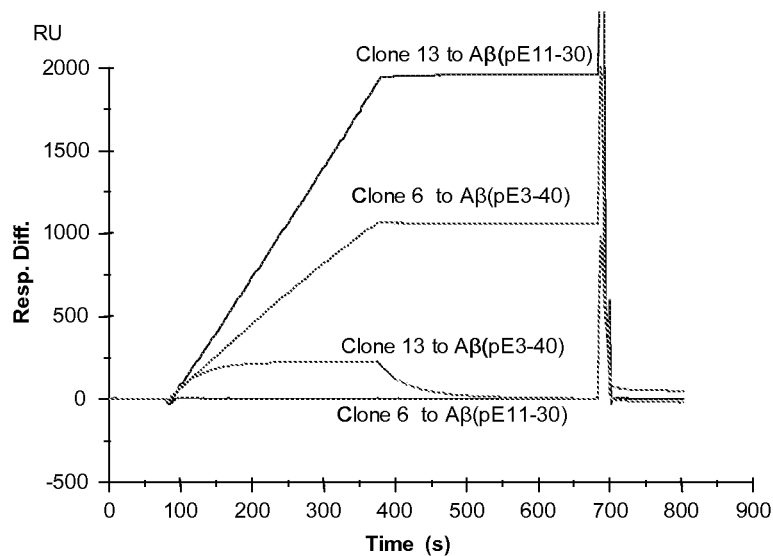

FIG. 20: Cross Reactivity of Anti Aβ11(pE) and Anti Aβ3(pE) Antibody

Determination of cross reactivity of anti Aβ11(pE) antibody (clone 13) to AβpE(11-30) and AβpE(3-40) peptide via SPR at Biacore 3000. Usage of CM5 chip with immobilized AβpE(11-30) with approx. 1000 RU and AβpE(3-40) with 1830 RU. Injection of 1 µg/ml antibodies with 30 µl/min over 300 s and recording of 300 s dissociation time, dilution in running buffer. The measured signals at flow cell with immobilized Aβ were subtracted with signal from non-coated flow cell.

Figure 21:
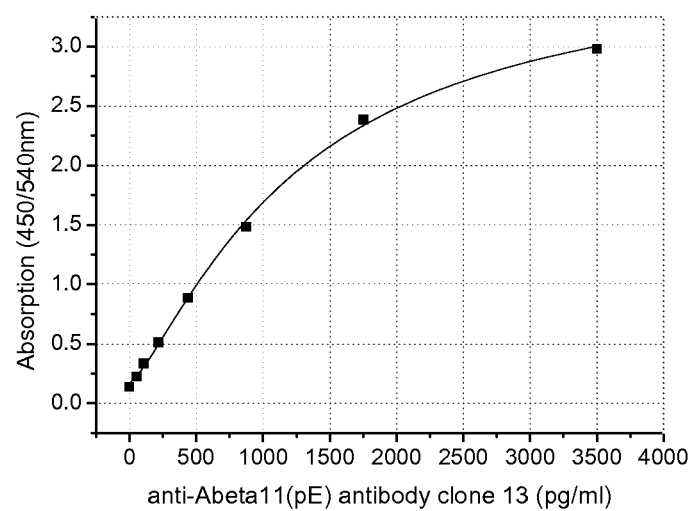

FIG. 21: Standard Curve of Anti Aβ11(pE) Antibody (Clone 13) in Auto-Ig-ELISA Immobilization of 200 ng/ml Aβ(pE11-20)-biotin at streptavidin coated microplate (2 h, at RT). Blocking with 200 µl ELISA-Blocker (−T) 1 h at RT and followed by wash cycle (3×300 µl/well wash buffer). Standard anti Aβ11(pE) antibody (clone 13) was diluted in ELISA-Blocker (+T) in radix division from 3500 pg/ml down to 55 pg/ml and incubated 2 h at 4° C. A wash cycle followed and detection with polyclonal rabbit anti-mouse Ig's HRP 1 h at 4° C. After wash cycle TMB/$H_2O_2$ were added, incubated 30 min at RT (dark) and enzyme reaction was stopped with 1 M $H_2SO_4$. Absorption was measured at 450/540 nm at TECAN Sunrise.

Figure 22:
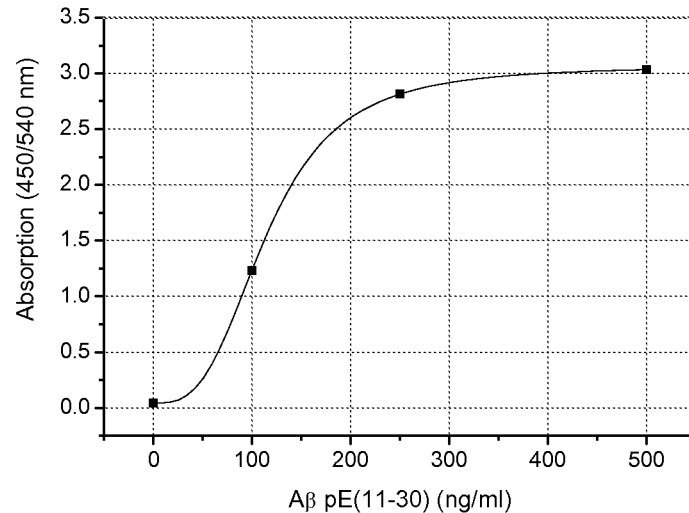

FIG. 22: Direct Aβ11(pE) ELISA (Clone 13)

AβpE(11-30) peptide with different concentrations was coated over night at 4° C. and then blocked with ELISA-Blocker (−T) 2 h at RT. Anti Aβ11(pE) antibody (clone 13) biotinylated was pre-incubated with streptavidin-HRP conjugate 10 min at RT and diluted in ELISA-Blocker (+T) were performed. Addition of 1 µg/ml antibody (clone 13). Wash cycles in-between incubations with 6×300 µl/well TBS-T buffer (except after peptide coating). TMB/$H_2O_2$ were added, incubated 30 min at RT (dark) and enzyme reaction was stopped with 1 M $H_2SO_4$. Absorption was measured at 450/540 nm at TECAN Sunrise.

Figure 23:
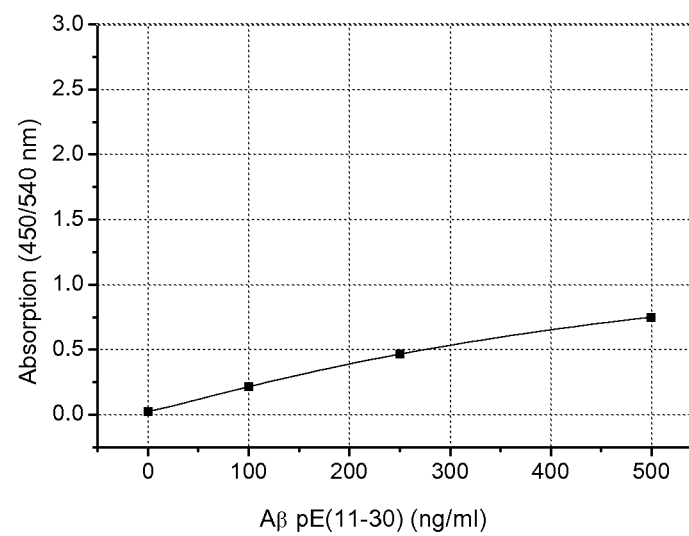

FIG. 23: Direct Aβ11(pE) ELISA (4G8)

AβpE(11-30) peptide with different concentrations was coated over night at 4° C. and then blocked with ELISA-Blocker (−T) 2 h at RT. Biotinylated 4G8 was pre-incubated with streptavidin-HRP conjugate for 10 min at RT and a radix two dilution in ELISA-Blocker (+T) were performed. Addition of 1 µg/ml 4G8 antibody. Wash cycles in-between incubations with 6×300 µl/well TBS-T buffer (except after peptide coating). TMB/$H_2O_2$ were added, incubated 30 min at RT (dark) and enzyme reaction was stopped with 1 M $H_2SO_4$. Absorption was measured at 450/540 nm at TECAN Sunrise.

Figure 24:
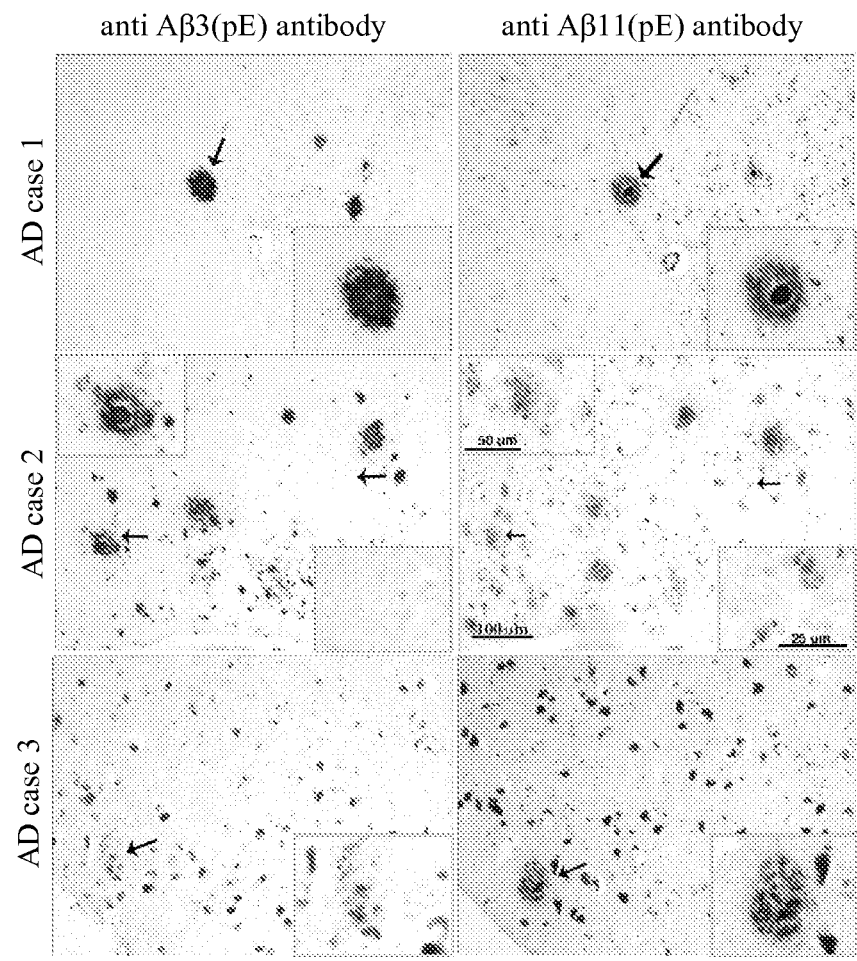

FIG. 24: Beta Amyloid Staining of Human AD Brain

Immunostaining was performed with anti Aβ11(pE) (clone 13) antibody. The AD brain sections were paraffin-embedded. The cell nuclei were stained with haematoxylin. Serial cuts from hippocampus of AD case 1; 3 and from frontal cortex of AD case 2 are imaged. AD case 1 and 2 showed extracellular, large plaques with deposition of Aβ11 (pE) (see narrow and magnification square). Intracellular Aβ11(pE) deposits in AD case 2 (see bottom right magnification square) and Aβ11(pE) deposits in AD case 3 (see narrow) were shown. The magnifications on the left and right images are similar. The images were kindly provided by the lab of C. Lemere (Havard Medical School, Boston).

Figure 25:
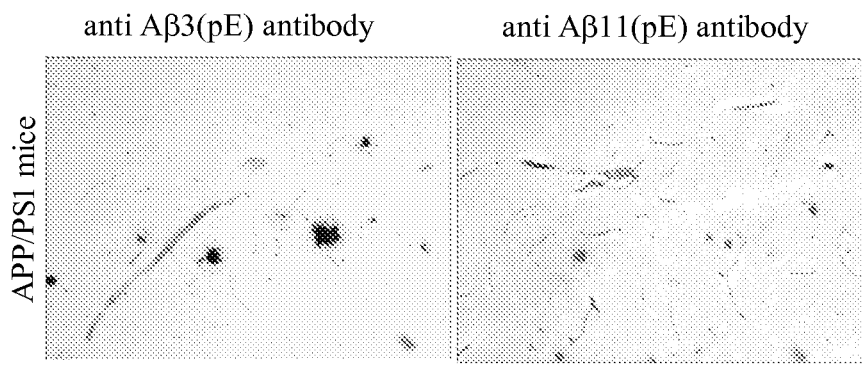

FIG. 25: Beta Amyloid Staining of APP/PS1 Mice Brain

Immunostaining of formalin fixed, paraffin embedded AD brain sections with anti Aβ11(pE) antibody. Cell nuclei were stained with haematoxylin. Serial cuts from hippocampus of the transgenic mice. Serial cuts showed vascular deposits of Aβ11(pE). The brown stain is shown at the blood vessels in the brain. The images were kindly provided by the lab of C. Lemere (Havard Medical School, Boston).

Figure 26:
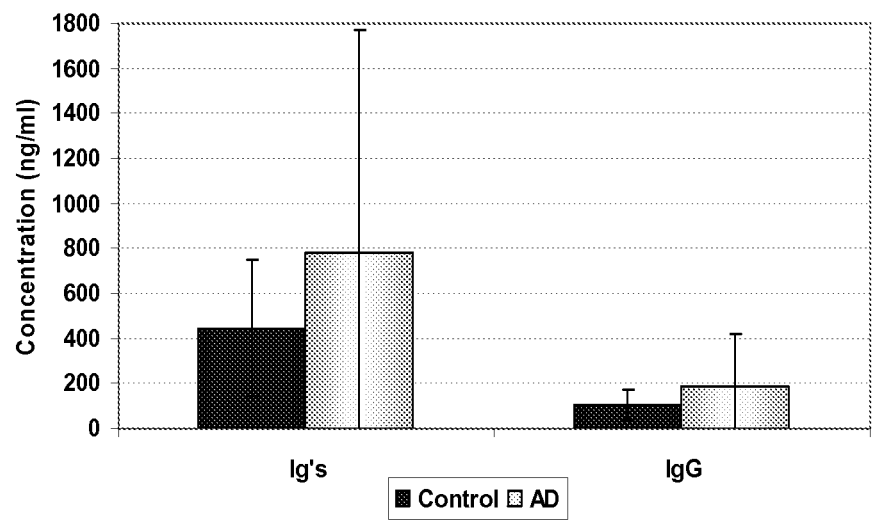

FIG. 26: Anti Aβ11(pE) IgG and Ig's Level in Auto-Ig-ELISA

EDTA-plasma of Alzheimer disease (AD) and control group (13 AD; controls) was analyzed concerning total immunglobulins and IgG in anti Aβ11(pE) autoantibody ELISA. Illustrated is the average and standard deviation of control and AD group. Results of duplicate determination, samples were measured within the standard curve.

Figure 27:
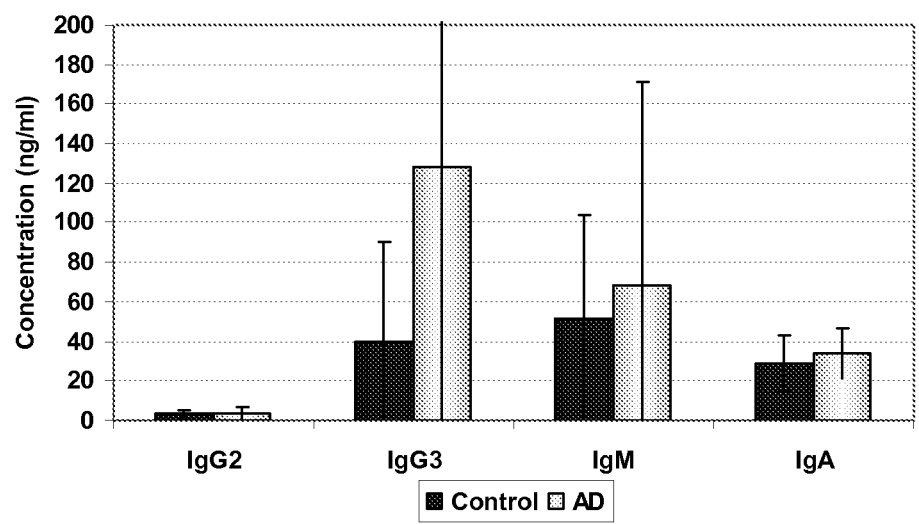

FIG. 27: Anti Aβ11(pE) IgG2, IgG3, IgM and IgA Level in Auto-Ig-ELISA

EDTA-plasma of Alzheimer disease (AD) and control group (13 AD; 30 controls) was analyzed concerning IgG2, IgG3, IgM and IgA in anti Aβ11(pE) autoantibody ELISA. Illustrated is the average and standard deviation of control and AD group. Results of duplicate determination, samples were measured within the standard curve.

DETAILED DESCRIPTION OF THE
PRESENTLY PREFERRED EMBODIMENTS

Definitions

The term "antibody" is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity. The antibody may be an IgM, IgG (e.g. IgG1, IgG2, IgG3 or IgG4), IgD, IgA or IgE, for example. Preferably however, the antibody is not an IgM antibody.

"Antibody fragments" comprise a portion of an intact antibody, generally the antigen binding or variable region of the intact antibody. Examples of antibody fragments include Fab, Fab', F(ab')2, and Fv fragments: diabodies; single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to "polyclonal antibody" preparations which typically include different antibodies directed against different determinants (epitopes), each monoclonal antibody is directed against a single determinant on the antigen. In addition to their specificity, the monoclonal antibodies can frequently be advantageous in that they are synthesized by the hybridoma culture, uncontaminated by other immunoglobulins. The "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Köhler et al., Nature, 256:495 (1975), or may be made by generally well known recombinant DNA methods. The "monoclonal antibodies" may also be isolated from phage antibody libraries using the techniques described in Clackson et al., Nature, 352:624-628 (1991) and Marks et al., J. Mol. Biol., 222: 581-597 (1991), for example.

The monoclonal antibodies herein specifically include chimeric antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain a minimal sequence derived from a non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences.

These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321:522-525 (1986), Reichmann et al, Nature. 332:323-329 (1988): and Presta, Curr. Op. Struct. Biel., 2:593-596 (1992). The humanized antibody includes a Primatized™ antibody wherein the antigen-binding region of the antibody is derived from an antibody produced by immunizing macaque monkeys with the antigen of interest.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_D$) in the same polypeptide chain ($V_H$-$V_D$). By using a linker that is too short to allow pairing between the two domains on the same chain, the domains are forced to pair with the complementary domains of another chain and create two antigen-binding sites. Diabodies are described more fully in Hollinger et al., Proc. Natl. Acad. Sol. USA, 90:6444-6448 (1993). An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, the expressions "cell", "cell line," and "cell culture" are used interchangeably and all such designations include progeny. Thus, the words "transformants" and "transformed cells" include the primary subject cell and culture derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, this will be clear from the context.

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

The language "diseases and disorders which are caused by or associated with amyloid or amyloid-like proteins" includes, but is not limited to, diseases and disorders caused by the presence or activity of amyloid-like proteins in monomeric, fibril, or polymeric state, or any combination of the three. Such diseases and disorders include, but are not limited to, amyloidosis, endocrine tumors, and macular degeneration.

The term "amyloidosis" refers to a group of diseases and disorders associated with amyloid plaque formation including, but not limited to, secondary amyloidosis and age-related amyloidosis such as diseases including, but not limited to, neurological disorders such as Alzheimer's Disease (AD), including diseases or conditions characterized by a loss of cognitive memory capacity such as, for example, mild cognitive impairment (MCI), sporadic Alzheimer's disease, Lewy body dementia, Down's syndrome, hereditary cerebral hemorrhage with amyloidosis (Dutch type); the Guam Parkinson-Dementia complex, familial forms of Alzheimer's disease like Familial British Dementia (FBD) and Familial Danish Dementia (FDD); as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes, and senile cardiac amyloidosis; and various eye diseases including macular degeneration, drusen-related optic neuropathy, and cataract due to beta-amyloid deposition.

"Amyloid β, Aβ or /β-amyloid" is an art recognized term and refers to amyloid β proteins and peptides, amyloid β precursor protein (APP), as well as modifications, fragments and any functional equivalents thereof. In particular, by amyloid β as used herein is meant any fragment produced by proteolytic cleavage of APP but especially those fragments which are involved in or associated with the amyloid pathologies including, but not limited to, $Aβ_{1-38}$, $Aβ_{1-40}$, $Aβ_{1-42}$. The amino acid sequences of these Aβ peptides are as follows:

```
Aβ 1-42 (SEQ ID NO. 1):
Asp-Ala-Glu-Phe-Arg-His-Asp-Ser-Gly-Tyr-Glu-Val-His-His-Gln-Lys-

Leu-Val-Phe-Phe-Ala-Glu-Asp-Val-Gly-Ser-Asn-Lys-Gly-Ala-Ile-Ile-

Gly-Leu-Met-Val-Gly-Gly-Val-Val-Ile-Ala

Aβ 1-40 (SEQ ID NO. 2):
Asp-Ala-Glu-Phe-Arg-His-Asp-Ser-Gly-Tyr-Glu-Val-His-His-Gln-Lys-

Leu-Val-Phe-Phe-Ala-Glu-Asp-Val-Gly-Ser-Asn-Lys-Gly-Ala-Ile-Ile-

Gly-Leu-Met-Val-Gly-Gly-Val-Val

Aβ 1-38 (SEQ ID NO. 3):
Asp-Ala-Glu-Phe-Arg-His-Asp-Ser-Gly-Tyr-Glu-Val-His-His-Gln-Lys-

Leu-Val-Phe-Phe-Ala-Glu-Asp-Val-Gly-Ser-Asn-Lys-Gly-Ala-Ile-Ile-

Gly-Leu-Met-Val-Gly-Gly
```

"pGlu-Aβ" or "Aβ N3pE" refers to N-terminally truncated forms of Aβ, that start at the glutamic acid residue at position 3 in the amino acid sequence of Aβ, and wherein said glutamic acid residue is cyclized to form a pyroglutamic acid residue. In particular, by pGlu-Aβ as used herein are meant those fragments which are involved in or associated with the amyloid pathologies including, but not limited to, pGlu-$Aβ_{3-38}$, pGlu-$Aβ_{3-40}$, p-Glu-$Aβ_{3-42}$.

The sequences of the N-terminally truncated forms of Aβ, $Aβ_{3-38}$, $Aβ_{3-40}$, $Aβ_{3-42}$ are as follows:

Aβ 3-42 (SEQ ID NO. 4):
Glu-Phe-Arg-His-Asp-Ser-Gly-Tyr-Glu-Val-His-His-Gln-Lys-Leu-Val-

Phe-Phe-Ala-Glu-Asp-Val-Gly-Ser-Asn-Lys-Gly-Ala-Ile-Ile-Gly-Leu-

Met-Val-Gly-Gly-Val-Val-Ile-Ala

Aβ 3-40 (SEQ ID NO. 5):
Glu-Phe-Arg-His-Asp-Ser-Gly-Tyr-Glu-Val-His-His-Gln-Lys-Leu-Val-

Phe-Phe-Ala-Glu-Asp-Val-Gly-Ser-Asn-Lys-Gly-Ala-Ile-Ile-Gly-Leu-

Met-Val-Gly-Gly-Val-Val

Aβ 3-38 (SEQ ID NO. 6):
Glu-Phe-Arg-His-Asp-Ser-Gly-Tyr-Glu-Val-His-His-Gln-Lys-Leu-Val-

Phe-Phe-Ala-Glu-Asp-Val-Gly-Ser-Asn-Lys-Gly-Ala-Ile-Ile-Gly-Leu-

Met-Val-Gly-Gly

"AβpGlu(11)", "Aβ(pE11)" or "Aβ11(pE)" refers to N-terminally truncated forms of Aβ, that start at the glutamic acid residue at position 11 in the amino acid sequence of Aβ, and wherein said glutamic acid residue is cyclized to form a pyroglutamic acid residue. In particular, by AβpGlu(11-x) as used herein are meant those fragments which are involved in or associated with the amyloid pathologies including, but not limited to, pGlu-Aβ$_{11-38}$, pGlu-Aβ$_{11-40}$, p-Glu-Aβ$_{11-42}$.

The sequences of the N-terminally truncated forms of Aβ, Aβ$_{11-38}$, Aβ$_{11-40}$, Aβ$_{11-42}$ are as follows:

Aβ 11-42 (SEQ ID NO. 7):
Glu-Val-His-His-Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly-Val-Val-Ile-Ala

Aβ 11-40 (SEQ ID NO. 8):
Glu-Val-His-His-Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly-Val-Val

Aβ 11-38 (SEQ ID NO. 9):
Glu-Val-His-His-Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly

In particular the present disclosure pertains to the following items:
1. Antibody, characterized in that it binds to AβpGlu(11) peptides or variants thereof, preferably with high affinity.
2. Antibody according to item 1, wherein said high affinity means a dissociation constant ($K_D$) value of $10^{-7}$ M, or better.
3. Antibody according to item 1 or 2, wherein said antibody is a monoclonal antibody.
4. Antibody according to any of the preceding items, wherein the variable part of the light chain of said antibody has a nucleotide sequence of SEQ ID NO: 51, or an amino acid sequence of SEQ ID NO: 52.
5. Antibody according to any of the preceding items, wherein the variable part of the heavy chain of said antibody has a nucleotide sequence of SEQ ID NO: 53, or an amino acid sequence of SEQ ID NO: 54.
6. Antibody according to any of the preceding items, wherein the variable part of the light chain of said antibody has the nucleotide sequence of SEQ ID NO: 51 or the amino acid sequence of SEQ ID NO: 52, and wherein the variable part of the heavy chain of said antibody has the nucleotide sequence of SEQ ID NO: 53, or the amino acid sequence of SEQ ID NO: 54.
7. Antibody according to any of the preceding items, wherein said antibody is Aβ 13-11-6 (Deposit No. DSM ACC 3100) or a functional variant thereof.
8. Antibody according to item 7, wherein said antibody is Aβ 13-11-6 (Deposit No. DSM ACC 3100).
9. Antibody according to any of the preceding items, wherein said antibody is a humanized or chimeric antibody, or an antibody fragment which retains the high affinity.
10. Antibody according to any of the preceding items for use in the detection of AβpGlu(11) peptides or variants thereof.
11. Antibody according to item 10, wherein said variants are selected from the following group:
    pGlu-Aβ$_{11-38}$
    pGlu-Aβ$_{11-40}$
    pGlu-Aβ$_{11-42}$, and
    pGlu-Aβ$_{11-x}$ variants,
    wherein x is an integer between 18 and 42, more preferably 30 and 42.
12. Antibody according to any of the preceding items, which is human.
13. Antibody according to any of the preceding items, which is a diabody or a single chain antibody which retains the high affinity.
14. Antibody according to any of the preceding items, which binds to the epitope bound by the antibodies defined in item 11.
15. Antibody according to any of the preceding items, which has the complementarity determining regions of the antibodies as defined in item 11.
16. Antibody according to any of the preceding items, wherein the variable part of the light chain of said antibody has one or more, such as one, two or three, complementarity determining regions which are the same as one or more, such as one, two or three, complementarity determining regions of the antibody having a variable part of a light chain which has a nucleotide sequence of SEQ ID NO: 51, or an amino acid sequence of SEQ ID NO: 52.

17. Antibody according to any of the preceding items, wherein the variable part of the light chain of said antibody has one or more, such as one, two or three, complementarity determining regions which are the same as one or more, such as one, two or three, complementarity determining regions of the antibody having a variable part of a heavy chain which has a nucleotide sequence of SEQ ID NO: 53, or an amino acid sequence of SEQ ID NO: 54.

18. Antibody according to any of the preceding items, which is labeled.

19. Antibody according to any of the preceding items, which is immobilised on a solid phase.

20. Antibody obtainable from the hybridoma cell line DSM ACC 3100.

21. Composition comprising the antibody as defined in any of the preceding items.

22. Composition according to item 21 for the treatment, prevention or delay of amyloidosis.

23. Composition according to item 21 or 22, wherein said amyloidosis is a neurodegenerative disease selected from the group consisting of mild cognitive impairment, Alzheimer's disease and neurodegeneration in Down Syndrome.

24. Composition according to item 21 or 22, wherein said amyloidosis is sporadic Alzheimer's disease or a Familial Alzheimer's dementia.

25. Composition according to item 24, wherein said Familial Alzheimer's dementia is Familial British Dementia or Familial Danish Dementia.

26. Hybridoma cell line DSM ACC 3100.

27. Use of the antibody as defined in any one of items 1 to 20 or the composition as defined in any one of items 21 to 25 in a diagnostic or therapeutic method.

28. The use according to item 27 for the diagnosis of an amyloid-associated disease or condition.

29. The use according to item 28, wherein said amyloidosis is a neurodegenerative disease selected from the group consisting of mild cognitive impairment, Alzheimer's disease and neurodegeneration in Down Syndrome.

30. The use according to item 28, wherein said amyloidosis is sporadic Alzheimer's disease or a Familial Alzheimer's dementia.

31. The use according to item 28, wherein said Familial Alzheimer's dementia is Familial British Dementia or Familial Danish Dementia.

32. In vitro diagnostic method for the diagnosis of an amyloid-associated disease or condition, in particular Alzheimer's disease, comprising the following steps:
contacting an antibody according to any one of items 1 to 20 with a sample from a subject suspected to be afflicted with said disease or condition, and
detecting binding of the antibody to a AβpGlu(11) protein, from the sample.

33. Diagnostic kit, comprising the antibody as defined in any one of items 1 to 20, and instructions for use, and—optionally—(a) further biologically active substance(s).

34. The diagnostic kit of item 33, wherein said further biological substance is an inhibitor of glutaminyl cyclase.

35. An oligonucleotide selected from the group consisting of SEQ ID NOs: 26 to 50.

The antibodies of the disclosure may be useful for the diagnosis of amyloidosis.

The antibodies of the disclosure may be used as affinity purification agents. In this process, the antibodies are immobilised on a solid phase such a Sephadex resin or filter paper, using methods well known in the art. The immobilized antibody is contacted with a sample containing the AβpGlu (11) peptide to be purified, and thereafter the support is washed with a suitable solvent that will remove substantially all the material in the sample except the AβpGlu(11)-peptide, which is bound to the immobilized antibody. Finally, the support is washed with another suitable solvent, such as glycine buffer, pH 5.0 that will release the AβpGlu (11)-peptide from the antibody.

Anti-AβpGlu(11)-peptide antibodies may also be useful in diagnostic assays for AβpGlu(11)-peptide, e.g. detecting its occurrence in specific cells, tissues, or serum. Thus, the antibodies may be used in the diagnosis of amyloidosis, in particular a neurodegenerative disease selected from the group consisting of mild cognitive impairment (MCI), Alzheimer's disease (AD), like for instance sporadic Alzheimer's disease (SAD) or Familial Alzheimer's dementias (FAD) such as Familial British Dementia (FBD) and Familial Danish Dementia (FDD) and neurodegeneration in Down Syndrome; preferably Alzheimer's disease.

For diagnostic applications, the antibody typically will be labeled with a detectable moiety. Numerous labels are available which can be generally grouped into the following categories:

(a) Radioisotopes, such as $^{35}$S, $^{14}$C, $^{125}$I, $^{3}$H, and $^{131}$I. The antibody can be labeled with the radioisotope using the techniques described in *Current Protocols in Immunology*, Volumes 1 and 2, Gütigen et al., Ed., Wiley-Interscience. New York, N.Y. Pubs., (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra for example. Fluorescence can be quantified using a fluorimeter.

(c) Various enzyme-substrate labels are available. The enzyme generally catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g, firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase. 0-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym (ed Langone & H. Van Vunakis), Academic Press, New York, 73: 147-166 (1981).

Examples of enzyme-substrate combinations include, for example:
(i) Horseradish peroxidase (HRPO) with hydrogen peroxidase as a substrate, wherein the hydrogen peroxidase oxidizes a dye precursor (e.g. orthophenylene diamine (OPD) or 3,3',5,5'-tetramethyl benzidine hydrochloride (TMB));
(ii) alkaline phosphatase (AP) with para-Nitrophenyl phosphate as chromogenic substrate; and
(iii) β-D-galactosidase (β-D-Gal) with a chromogenic substrate (e.g. p-nitrophenyl-β-D-galactosidase) or the fluorogenic substrate 4-methylumbelliferyl-β-D-galactosidase.

Numerous other enzyme-substrate combinations are available to those skilled in the art.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). Thus, indirect conjugation of the label with the antibody can be achieved.

The AβpGlu(11)-antibody need not be labeled, and the presence thereof can be detected using a labeled antibody, which binds to the AβpGlu(11)-antibody.

The antibodies of the present disclosure may be employed in any known assay method, such as competitive binding assays, direct and indirect sandwich assays, and immunoprecipitation assays. Zola, *Monoclonal Antibodies A Manual of Techniques*, pp. 147-158 (CRC Press. Inc., 1987)

Competitive binding assays rely on the ability of a labeled standard to compete with the test sample analyte for binding with a limited amount of antibody. The amount of AβpGlu (11) peptide in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. The second antibody may itself be labeled with a detectable moiety (direct sandwich assays) or may be measured using an anti-immunoglobulin antibody that is labeled with a detectable moiety (indirect sandwich assay). For example, one preferable type of sandwich assay is an ELISA assay, in which case the detectable moiety is an enzyme.

For immunohistochemistry, the tissue sample may be fresh or frozen or may be embedded in paraffin and fixed with a preservative such as formalin, for example.

Diagnostic Kits

As a matter of convenience, the antibody of the present disclosure can be provided in a kit, i.e., a packaged combination of reagents in predetermined amounts with instructions for performing the diagnostic assay. Where the antibody is labeled with an enzyme, the kit will include substrates and cofactors required by the enzyme (e.g. a substrate precursor which provides the detectable chromophore or fluorophore). In addition, other additives may be included such as stabilizers, buffers (e.g. a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

The diagnostic kit according to the disclosure may contain a further biologically active substance as described below. Especially preferred for the use in the diagnostic kit are inhibitors of glutaminyl cyclase.

The diagnostic kit of the disclosure is especially useful for the detection and diagnosis of amyloid-associated diseases and conditions, in particular neurodegenerative diseases selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease.

The present disclosure pertains in particular to antibodies which are characterized in that they bind to AβpGlu(11)-peptides with a high affinity. The present disclosure also pertains to antibodies which are characterized in that they bind to AβpGlu(11)-peptides or variants thereof with a high affinity. Said high affinity means in the context of the present disclosure an affinity of a $K_D$ value of $10^{-7}$ M or better, preferably a $K_D$ value of $10^{-8}$ M or better, and even more preferably a $K_D$ value of $10^{-9}$ M-$10^{-12}$ M. Thereby, the inventive antibodies bind to AβpGlu(11)-peptides with a higher affinity than previously known antibodies.

In particular the antibody is preferably a monoclonal antibody and is Aβ13-11-6(DSM ACC 3100).

The antibody according to the present disclosure is especially useful in a diagnostic method to detect amyloidosis, in particular a neurodegenerative disease selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease.

According to a preferred embodiment, the antibody can be humanized or is a chimeric antibody or is a human antibody.

Further, the antibody as selected from the above-mentioned group can also be a functional variant of said group.

In the context of the present disclosure, a variant of a AβpGlu(11) peptide is in particular
pGlu-Aβ$_{11-38}$,
pGlu-Aβ$_{11-40}$,
pGlu-Aβ$_{11-42}$ Further variants of AβpGlu(11) peptides are all pGlu-Aβ$_{11-x}$ variants, which have been shown to accumulate in the brain as a consequence of Alzheimer's disease or preceding Alzheimer's disease. X is defined as an integer between 18 and 42, e.g. in the above pGlu-Aβ$_{11-42}$, "42" would be the integer for "x".

In the context of the present disclosure a "functional variant" of the inventive antibody is an antibody which retains the binding capacities, in particular binding capacities with high affinity to a pGlu-Aβ$_{11-x}$ peptide or functional variant thereof. The provision of such functional variants is known in the art and encompasses the above-mentioned possibilities, which were indicated under the definition of antibodies and fragments thereof.

In a preferred embodiment, the antibody is an antibody fragment, as defined above.

In a further preferred embodiment, the inventive antibody is an antibody which binds to the epitope which is bound by the antibodies as defined above, in particular antibody 13-11-6.

In a further preferred embodiment, the antibody of the disclosure is an antibody which has the complementarity-determining regions (CDRs) of the above-defined antibodies. Preferably, the antibody can be labeled; possible labels are those as mentioned above and all those known to a person skilled in the art of diagnostic uses of antibodies in particular.

Preferably, the antibody is immobilized on a solid phase.

The present disclosure also concerns an antibody which is obtainable from hybridoma cell line 13-11-6 (DSM ACC 3100).

The present disclosure also relates to a composition which comprises the antibody as defined above. In particular, said composition is a composition for a diagnostic use, especially for the diagnosis of a neurodegenerative disease selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease; in particular by detection of AβpGlu(11) peptide or variants thereof in a biological sample.

In another embodiment, the antibody according to the disclosure and as described herein before or a fragment thereof, exhibits a binding affinity to an AβpGlu(11) oligomer, fiber, fibril or filament which is at least 2 times, particularly at least 4 times, particularly at least 10 times, particularly at least 15 times, more particularly at least 20 times, but especially at least 25 times higher than the binding affinity to an AβpGlu(11) monomer.

In still another embodiment, an antibody or a fragment thereof or a chimeric antibody or a fragment thereof, or a humanized antibody or a fragment thereof is provided as described herein before, which antibody substantially binds to aggregated Aβ, including Aβ plaques, in the mammalian, particularly the human brain but, preferably, does not show any significant cross-reactivity with amyloid precursor protein (APP).

In another aspect of the disclosure, the antibody or a fragment thereof or the chimeric antibody or a fragment thereof, or a humanized antibody or a fragment thereof is provided as described herein before, which antibody substantially binds to soluble polymeric amyloid, particularly amyloid β (Aβ), including Aβ monomers, in the mammalian, particularly the human brain but, preferably, does not show any significant cross-reactivity with amyloid precursor protein (APP).

The present disclosure relates also to humanized forms of the antibodies as defined above, compositions comprising said humanized antibodies and the use of said compositions for the treatment of amyloidosis, especially for the treatment of neurodegenerative disease in a mammal, in particular in a human. Said neurodegenerative disease is in particular selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome. Preferably, said neurodegenerative disease is Alzheimer's disease.

The present disclosure is also directed to hybridoma cell line 13-11-6.

The present disclosure also pertains to the use of the antibody or the composition comprising the antibody, both as defined above, for use in an in vitro diagnostic method. In particular, this diagnostic method is directed to diagnosis of a neurodegenerative disease selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease; especially by detecting an AβpGlu(11) peptide or variants thereof in a biological sample.

Preferably, said sample is a serum sample.

According to another preferred embodiment, said sample is a liquor or cerebrospinal fluid (CSF) sample.

In a particularly preferred embodiment, the present disclosure pertains to the following method:

In vitro or in situ diagnostic method for the diagnosis of an amyloid-associated disease or condition, preferably Alzheimer's disease, comprising the following steps:

contacting an antibody according to the disclosure with a sample, preferably selected from a serum, liquor or CSF sample, most preferably a serum sample; or a specific body part or body area of a subject suspected to be afflicted with said condition or disease, and detecting binding of the antibody to a AβpGlu(11) peptide, from the sample.

More particularly, the disclosure relates to a method of diagnosis of an amyloid-associated disease or condition, preferably Alzheimer's disease, comprising detecting the immunospecific binding of an antibody or an active fragment thereof to a AβpGlu(11) peptide, in a sample or in situ which includes the steps of (a) bringing the sample or a specific body part or body area suspected to contain the amyloid protein into contact with an antibody, particularly a monoclonal antibody according to the disclosure, or a chimeric antibody or a fragment thereof, or a humanized antibody or a fragment thereof according to the disclosure and as described herein before, and/or a functional part thereof, which antibody binds a AβpGlu(11) peptide;

(b) allowing the antibody and/or a functional part thereof, to bind to the AβpGlu(11) peptide to form an immunological complex;

(c) detecting the formation of the immunological complex; and (d) correlating the presence or absence of the immunological complex with the presence or absence of AβpGlu(11) peptide in the sample or specific body part or area.

Also comprised is a method of determining the extent of amyloidogenic plaque burden in a tissue and/or body fluids comprising (a) obtaining a sample representative of the tissue and/or body fluids under investigation;

(b) testing said sample for the presence of amyloid protein with an antibody, particularly a monoclonal antibody according to the disclosure, or a chimeric antibody or a fragment thereof, or a humanized antibody or a fragment thereof according to the disclosure and as described herein before, and/or a functional part thereof;
(c) determining the amount of antibody bound to the protein; and
(d) calculating the plaque burden in the tissue and/or body fluids.

In particular, the disclosure relates to a method of determining the extent of amyloidogenic plaque burden in a tissue and/or body fluids, wherein the formation of the immunological complex in step c) is determined such that presence or absence of the immunological complex correlates with presence or absence of amyloid protein, in particular AβpGlu(11) peptides.

In still another embodiment, the disclosure relates to a composition comprising the antibody according to the disclosure, or a chimeric antibody or a fragment thereof, or a humanized antibody or a fragment thereof according to the disclosure and as described herein before including any functionally equivalent antibody or any derivative or functional parts thereof, in a therapeutically effective amount, in particular a composition which is a pharmaceutical composition optionally further comprising a pharmaceutically acceptable carrier.

In another embodiment of the disclosure, said composition comprises the antibody in a therapeutically effective amount. Further comprised by the disclosure is a mixture comprising an antibody, particularly a monoclonal antibody according to the disclosure, or a chimeric antibody or a fragment thereof, or a humanized antibody or a fragment thereof according to the disclosure and as described herein before including any functionally equivalent antibody or any derivative or functional parts thereof, in a therapeutically effective amount and, optionally, a further biologically active substance and/or a pharmaceutically acceptable carrier and/or a diluent and/or an excipient.

In particular, the disclosure relates to a mixture, wherein the further biologically active substance is a compound used in the medication of amyloidosis, a group of diseases and disorders associated with amyloid or amyloid-like protein such as the AβpGlu(11) protein involved in neurodegenerative diseases selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease.

In another embodiment of the disclosure, the other biologically active substance or compound may also be a therapeutic agent that may be used in the treatment of amyloidosis caused by AβpGlu(11) or may be used in the medication of other neurological disorders.

The other biologically active substance or compound may exert its biological effect by the same or a similar mechanism as the antibody according to the disclosure or by an unrelated mechanism of action or by a multiplicity of related and/or unrelated mechanisms of action.

Generally, the other biologically active compound may include neutron-transmission enhancers, psychotherapeutic drugs, acetylcholine esterase inhibitors, calcium-channel blockers, biogenic amines, benzodiazepine tranquilizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists. More particularly, the disclosure relates to a mixture comprising at least one compound selected from the group consisting of compounds effective against oxidative stress, anti-apoptotic compounds, metal chelators, inhibitors of DNA repair such as pirenzepin and metabolites, 3-amino-1-propanesulfonic acid (3 APS), 1,3-propanedisulfonate (1,3PDS), α-secretase activators, β- and γ-secretase inhibitors, tau proteins, neurotransmitter, 3-sheet breakers, attractants for amyloid beta clearing/depleting cellular components, inhibitors of N-terminal truncated amyloid beta including pyroglutamated amyloid beta 3-42, such as inhibitors of glutaminyl cyclase, anti-inflammatory molecules, or cholinesterase inhibitors (ChEIs) such as tacrine, rivastigmine, donepezil, and/or galantamine, M1 agonists and other drugs including any amyloid or tau modifying drug and nutritive supplements, and nutritive supplements, together with an antibody according to the present disclosure and, optionally, a pharmaceutically acceptable carrier and/or a diluent and/or an excipient.

The disclosure further relates to a mixture, wherein the compound is a cholinesterase inhibitor (ChEIs), particularly a mixture, wherein the compound is one selected from the group consisting of tacrine, rivastigmine, donepezil, galantamine, niacin and memantine.

In a further embodiment, the mixtures according to the disclosure may comprise niacin or memantine together with an antibody according to the present disclosure and, optionally, a pharmaceutically acceptable carrier and/or a diluent and/or an excipient.

In a further embodiment, the mixtures according to the disclosure may comprise a glutaminyl cyclase inhibitor together with an antibody according to the present disclosure and, optionally, a pharmaceutically acceptable carrier and/or a diluent and/or an excipient.

Preferred inhibitors of glutaminyl cyclase are described in WO 2005/075436, in particular examples 1-141 as shown on pp. 31-40. The synthesis of examples 1-141 is shown on pp. 40-48 of WO 2005/075436. The disclosure of WO 2005/075436 regarding examples 1-141, their synthesis and their use as glutaminyl cyclase inhibitors is incorporated herein by reference.

Further preferred inhibitors of glutaminyl cyclase are described in WO 2008/055945, in particular examples 1-473 as shown on pp. 46-155. The synthesis of examples 1-473 is shown on pp. 156-192 of WO 2008/055945. The disclosure of WO 2008/055945 regarding examples 1-473, their synthesis and their use as glutaminyl cyclase inhibitors is incorporated herein by reference.

Further preferred inhibitors of glutaminyl cyclase are described in WO 2008/055947, in particular examples 1-345 as shown on pp. 53-118. The synthesis of examples 1-345 is shown on pp. 119-133 of WO 2008/055947. The disclosure of WO 2008/055947 regarding examples 1-345, their synthesis and their use as glutaminyl cyclase inhibitors is incorporated herein by reference.

Further preferred inhibitors of glutaminyl cyclase are described in WO 2008/055950, in particular examples 1-212 as shown on pp. 57-120. The synthesis of examples 1-212 is shown on pp. 121-128 of WO 2008/055950. The disclosure of WO 2008/055950 regarding examples 1-212, their synthesis and their use as glutaminyl cyclase inhibitors is incorporated herein by reference.

Further preferred inhibitors of glutaminyl cyclase are described in WO2008/065141, in particular examples 1-25 as shown on pp. 56-59. The synthesis of examples 1-25 is shown on pp. 60-67 of WO2008/065141. The disclosure of WO2008/065141 regarding examples 1-25, their synthesis and their use as glutaminyl cyclase inhibitors is incorporated herein by reference.

Further preferred inhibitors of glutaminyl cyclase are described in WO 2008/110523, in particular examples 1-27 as shown on pp. 55-59. The synthesis of examples 1-27 is shown on pp. 59-71 of WO 2008/110523. The disclosure of WO 2008/110523 regarding examples 1-27, their synthesis and their use as glutaminyl cyclase inhibitors is incorporated herein by reference.

Further preferred inhibitors of glutaminyl cyclase are described in WO 2008/128981, in particular examples 1-18 as shown on pp. 62-65. The synthesis of examples 1-18 is shown on pp. 65-74 of WO 2008/128981. The disclosure of WO 2008/128981 regarding examples 1-18, their synthesis and their use as glutaminyl cyclase inhibitors is incorporated herein by reference.

Further preferred inhibitors of glutaminyl cyclase are described in WO 2008/128982, in particular examples 1-44 as shown on pp. 61-67. The synthesis of examples 1-44 is shown on pp. 68-83 of WO 2008/128982. The disclosure of WO 2008/128982 regarding examples 1-44, their synthesis and their use as glutaminyl cyclase inhibitors is incorporated herein by reference.

Further preferred inhibitors of glutaminyl cyclase are described in WO 2008/128983, in particular examples 1-30 as shown on pp. 64-68. The synthesis of examples 1-30 is shown on pp. 68-80 of WO 2008/128983. The disclosure of WO 2008/128983 regarding examples 1-30, their synthesis and their use as glutaminyl cyclase inhibitors is incorporated herein by reference.

Further preferred inhibitors of glutaminyl cyclase are described in WO 2008/128984, in particular examples 1-36 as shown on pp. 63-69. The synthesis of examples 1-36 is shown on pp. 69-81 of WO 2008/128984. The disclosure of WO 2008/128984 regarding examples 1-36, their synthesis and their use as glutaminyl cyclase inhibitors is incorporated herein by reference.

Further preferred inhibitors of glutaminyl cyclase are described in WO 2008/128985, in particular examples 1-71 as shown on pp. 66-76. The synthesis of examples 1-71 is shown on pp. 76-98 of WO 2008/128985. The disclosure of WO 2008/128985 regarding examples 1-71, their synthesis and their use as glutaminyl cyclase inhibitors is incorporated herein by reference.

Further preferred inhibitors of glutaminyl cyclase are described in WO 2008/128986, in particular examples 1-7 as shown on pp. 65-66. The synthesis of examples 1-7 is shown on pp. 66-73 of WO 2008/128986. The disclosure of WO 2008/128986 regarding examples 1-7, their synthesis and their use as glutaminyl cyclase inhibitors is incorporated herein by reference.

In still another embodiment of the disclosure mixtures are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with an antibody, particularly a monoclonal antibody according to the disclosure, but particularly a chimeric antibody or a fragment thereof, or a humanized antibody or a fragment thereof according to the disclosure and as described herein and, optionally, a pharmaceutically acceptable carrier and/or a diluent and/or an excipient.

In a specific embodiment of the disclosure, the compositions and mixtures according to the disclosure and as described herein before comprise the antibody and the biologically active substance, respectively, in a therapeutically effective amount.

Other compounds that can be suitably used in mixtures in combination with the antibody according to the present disclosure are described in WO2008/065141 (see especially pages 37/38), including PEP-inhibitors (pp. 43/44), LiCl, inhibitors of dipeptidyl aminopeptidases, preferably inhibitors of DP IV or DP IV-like enzymes (see pp. 48/49); acetylcholinesterase (ACE) inhibitors (see p. 47), PIMT enhancers, inhibitors of beta secretases (see p. 41), inhibitors of gamma secretases (see pp. 41/42), inhibitors of neutral endopeptidase, inhibitors of phosphodiesterase-4 (PDE-4) (see pp. 42/43), TNFalpha inhibitors, muscarinic M1 receptor antagonists (see p. 46), NMDA receptor antagonists (see pp. 47/48), sigma-1 receptor inhibitors, histamine H3 antagonists (see p. 43), immunomodulatory agents, immunosuppressive agents or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS; beta-amyloid antibodies (see p. 44), cysteine protease inhibitors (see p. 44); MCP-1 antagonists (see pp. 44/45), amyloid protein deposition inhibitors (see 42) and beta amyloid synthesis inhibitors (see p. 42), which document is incorporated herein by reference.

In another embodiment, the disclosure relates to a mixture comprising the antibody, particularly a monoclonal antibody according to the disclosure, or a chimeric antibody or a fragment thereof, or a humanized antibody or a fragment thereof according to the disclosure and as described herein before and/or the biologically active substance in a therapeutically effective amount.

The disclosure further relates to the use of an antibody, particularly a monoclonal antibody according to the disclosure, but particularly a chimeric antibody or a fragment thereof, or a humanized antibody or a fragment thereof according to the disclosure and as described herein before and/or a functional part thereof and/or a pharmaceutical composition, or a mixture comprising said antibody, for the preparation of a medicament for treating or alleviating the effects of amyloidosis, a group of diseases and disorders associated with amyloid plaque formation including secondary amyloidosis and age-related amyloidosis such as diseases including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration.

Also comprised by the present disclosure is a method for the preparation of an antibody, particularly a monoclonal antibody according to the disclosure, but particularly a chimeric antibody or a fragment thereof, or a humanized antibody or a fragment thereof according to the disclosure and as described herein before and/or a functional part thereof and/or a pharmaceutical composition, or a mixture comprising said antibody and/or a functional part thereof, particularly in a therapeutically effective amount, for use in a method of preventing, treating or alleviating the effects of amyloidosis, a group of diseases and disorders associated with amyloid plaque formation including secondary amyloidosis and age-related amyloidosis such as diseases including, but not limited to neurodegenerative diseases such as mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; Lewy body dementia, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration comprising formulating an antibody, particularly a monoclonal antibody according to the disclosure, but particularly a chimeric antibody or a fragment thereof, or a humanized antibody or a fragment thereof according to the disclosure in a pharmaceutically acceptable form.

Further comprised by the present disclosure is a method for preventing, treating or alleviating the effects of amyloidosis, a group of diseases and disorders associated with amyloid plaque formation including secondary amyloidosis and age-related amyloidosis such as diseases including, but not limited to, neurological disorders such as mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; Lewy body dementia, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration by administering an antibody and/or a functional part thereof, but particularly a humanized antibody and/or a functional part thereof, or a composition or mixture comprising such an antibody and/or a functional part thereof, to an animal or a human affected by such a disorder comprising administering the antibody in a therapeutically effective amount.

It is also an object of the disclosure to provide a method for the treatment of amyloidosis, a group of diseases and disorders associated with amyloid plaque formation including secondary amyloidosis and age-related amyloidosis including, but not limited to, neurodegenerative diseases such as mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; particularly a disease or condition characterized by a loss of cognitive memory capacity by administering to an animal, particularly a mammal or a human, an antibody, particularly a pharmaceutical composition according to the disclosure and as described herein.

In a specific embodiment the disclosure provides a method for retaining or increasing cognitive memory capacity but, particularly, for restoring the cognitive memory capacity of an animal, particularly a mammal or a human, suffering from memory impairment by administering to an animal, particularly a mammal or a human, an antibody, particularly a pharmaceutical composition according to the disclosure and as described herein before.

It is a further object of the disclosure to provide a therapeutic composition and a method of producing such a composition as well as a method for the treatment of amyloidosis, a group of diseases and disorders associated with amyloid plaque formation including secondary amyloidosis and age-related amyloidosis including, but not limited to, neurodegenerative diseases such as mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; particularly a disease or condition characterized by a loss of cognitive memory capacity, using an antibody according to the disclosure and as described herein before.

In particular, the disclosure relates to the treatment of an animal, particularly a mammal or a human, suffering from an amyloid-associated condition characterized by a loss of cognitive memory capacity that leads to the retention of cognitive memory capacity.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise.

In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

1. Material and Methods
1.1 Cell Culture Techniques
1.1.1 Hybridoma Cells and Antibody Screening Murine hybridoma cells producing monoclonal antibodies (mAb) against Aβ species were provided from Biogenes GmbH (Berlin). Female BALB/c mice were immunized with chemical synthesized antigen Aβ(pE11-14) which was linked at the C-terminal cysteine residue with keyhole limpet hemocyanin (KLH) protein. The KLH protein is potently immunogenic and was applied as vaccine carrier protein.

The cell fusion was performed with spleen cells of the immunized mice and the murine myeloma cell line SP2/0-Ag14. After cell fusion, the hybridoma cells were selected with hypoxanthine aminopterin thymidine medium (HAT). Therefore, HAT medium allows selection of hybridoma cells, which inherit the hypoxanthine guanine phosphoribosyl transferase (HGPRT) gene from B cells and tumorigenic property from myeloma cells. Afterwards the hybridoma supernatants were screened for the presence of specific mAb against Aβ(pE11-14). The mAb were examined concerning their ability to bind at different modified Aβ-peptides. Therefore Aβ-peptides were spotted at a hydroxy-cellulose-membrane, incubated with mAb from cell culture supernatants and were detected by labeled antibodies. Hybridoma cells, which produce specific mAb against the N-terminal modified Aβ11(pE) peptide and showed no significant cross-reactions with other modified Aβ-peptides (see Table 1) were selected for recloning. Through limited dilution techniques the hybridoma cells were cloned to achieve one isolated clone.

The followed hybridoma clone was stable after recloning and provided from BioGenes:

pEVHH-59025 13-11-6 (clone 13)

The present study intended to successfully cultivate the hybridoma cell for the production of mAb in cell culture supernatant. The mAb concentration in cell culture supernatant of the clone should be determined by Surface Plasmon Resonance (SPR). An additional aim was the optimization of cultivation, whereby the adaption of hybridoma cells from serum containing serum free medium should be performed to simplify the purification of mAb. Furthermore the mAb should be purified, biophysically characterized and applied in assay or used for immunostaining.

TABLE 1

| Seq ID No. | Peptide | Sequence |
| --- | --- | --- |
| 10 | Aβ(2-10) | KMDAEFRHDSGYE |
| 11 | Aβ(1-13) | DAEFRHDSGYEVH |
| 12 | Aβ(iso 1-13) | iDAEFRHDSGYEVH |
| 13 | Aβ(2-14) | AEFRHDSGYEVHH |
| 14 | Aβ(3-15) | EFRHDSGYEVHHQ |
| 15 | Aβ(p3-15) | pEFRHDSGYEVHHQ |
| 16 | Aβ(4-16) | FRHDSGYEVHHQK |
| 17 | Aβ(9-21) | GYEVHHQKLVFFA |
| 18 | Aβ(11-23) | EVHHQKLVFFAED |
| 19 | Aβ(p11-23) | pEVHHQKLVFFAED |
| 20 | Aβ(12-24) | VHHQKLVFFAEDV |
| 21 | Aβ(iso D7 1-13) | DAEFRHisoDSGYEVH |
| 22 | Aβ(iso 7-19) | iDSGYEVHHQKLVF |
| 23 | Aβ(17-29) | LVFFAEDVGSNKG |
| 24 | Aβ(25-37) | GSNKGAIIGLMVG |
| 25 | Aβ(30-42) | AIIGLMVGGVVIA |

1.1.2 Cultivation of Hybridoma Cells

The hybridoma cells were cultivated in cell culture flasks at 37° C. and in a humidified atmosphere of 5% $CO_2$. The cultivation D-MEM medium (with L-glutamine, sodium pyruvate, 4.5 g/l glucose, Invitrogen) was supplemented with 15% FBS and 1% MEM-NEA (non essential amino acids, Invitrogen). Immediately before use of culture medium a stock solution of 50 mM β-mercaptoethanol and a fresh defrosted stock solution of 200 mM L-glutamine were used with a final concentration of at least 50 µM β-mercaptoethanol and 2 mM L-glutamine. The subculture of cells was routinely performed dependent upon cell density twice per week. The cell density should be between $1\times10^6$ and $2\times10^6$ living cells/ml. For passaging of hybridoma cells the partial adherent cells were detached from bottle bottom through carefully up and down pipetting of cell suspension, transferred into falcon tubes and centrifuged at 300×g for 5 min. Afterwards the cell culture supernatant containing mAb was aspirated then collected in a reservoir and stored at 4° C. For SPR measurement, a sample (100 µl) was taken from cell culture supernatant. After resuspension of cell pellet with fresh culture medium the cell density was determined by using the Casy® Cell Counter (Schärfe System GmbH, Reutlingen). Therefore the cell suspension was 10-times diluted in Casy®ton (physiological saline solution) and then 100 µl of cell dilution was transferred into 9900 µl Casy®ton. The device determined the amount of living and dead cells as well as the total cell amount per ml in the sample by electric current exclusion. Vital cells with intact cell membranes exclude the electrical current whereas dead cells with defect cell membranes are electrically conductive. Then the cells were seeded with a density, dependent on the cell growth, between $1\times10^5$ and $5\times10^5$ living cells/ml in T-flask (25 cm$^2$-175 cm$^2$ according to requirement).

1.1.3 Cryopreservation of Hybridoma Cells

Hybridoma cells in logarithmic growth phase and with viability over 85% were cryopreserved. Freezing of cells should be performed as early as possible with low passage number. The hybridoma cells were centrifuged at 300×g for 5 min and resuspended at a concentration of $7\times10^6$ living cells/ml in 45% culture medium (D-MEM, 1 MEM-NEA, 15% FBS), 45% heat-inactivated fetal bovine serum (FBS) and 10% dimethylsulfoxide (DMSO). The cell suspension was quickly transferred in 1 ml aliquots into cryo vials. The cryo vials were placed inside the freezing container filled with isopropyl alcohol of QUALIFREEZE to guarantee a slow cooling rate of 1° C. per minute. The freezing container was stored for a maximum of 48 hours at −80° C. Afterwards the cryo vials were transferred to liquid nitrogen at −196° C.

1.1.4 Thawing of Hybridoma Cells

The hybridoma cells stored in liquid nitrogen were fast thawed in a water bath at 37° C. until small pieces of ice were left inside. The freezing media used contained DMSO which has a cell toxic effect at temperatures higher than 4° C. Therefore the cell culture medium should be cooled to 4° C. The cell suspension was transferred in falcon tubes and diluted drop-wise with 5 ml 4° C. culture medium. The cells were immediately centrifuged at 300×g for 5 min and the supernatant with the cell toxic anti-freeze agent DMSO was aspirated. The cell pellet was resuspended in 37° C. heated cell culture medium and seeded in a 25 cm$^2$ T-flask with a cell density of $5-7\times10^5$ living cells per ml.

1.1.5 Screening for Contamination

Hybridoma cells were examined every two month for mycoplasma contamination. Therefore the MycoAlert®Mycoplasma Detection Kit from Lonza was used to test the cell culture supernatant. The assay is a selective biochemical test that exploits the activity of certain mycoplasmal enzymes. The viable mycoplasma are lysed and the enzymes react with the MycoAlert™ Substrate catalyzing the conversion of ADP to ATP. The increase of ATP level can be detected using a bioluminescence reaction because the emitted light intensity correlates with ATP concentration.

Therefore a sample of cell culture supernatant was centrifuged at 200×g for 5 min then 100 µl hybridoma supernatant were mixed with 100 µl MycoAlert™ Reagent in a 96-well plate and incubated 5 min at room temperature. The luminescence was measured with the luminometer GeniosPro (Tecan) and then 100 µl MycoAlert™ Substrate were added, incubated for 10 min at room temperature and the luminescence was measured again. When the ratio of second luminescence measurement to first one is less than 1, the cells are not contaminated.

1.1.6 Hybridoma Cell Cultivation in Shake Flask

Hybridoma cells grow in stationary suspension culture (e.g. T-flask) and in agitated suspension culture (e.g. shake flask). For the antibody production the hybridoma cells were cultivated for about seven days in shake flasks parallel to stationary cultivation in T-flasks. The cells were seeded with a density between $3\times10^5$ and $5\times10^5$ cells/ml in shake flask. The cell culture media (D-MEM, 1 MEM-NEA, 15% FBS or ultra low IgG FBS) was supplemented with 0.5% gentamicin, 50 µM mercaptoethanol and 2 mM L-glutamine. To facilitate an optimal gas exchange only about 30% of total shake flask volume were filled with media. The suspension culture in shake flask was incubated at 37° C., 5% $CO_2$ and rotated at 80 rpm. After seven days incubation the cell suspension was transferred with pipette in falcon tubes and centrifuged at 500×g for 10 min. Afterwards the cell culture supernatant containing the antibodies was collected in a reservoir and stored at 4° C. For SPR measurement a sample of cell culture supernatant was taken. The cell pellet was discarded.

1.1.7 Adaption of Hybridoma Cells to Serum-Free Media

The application of serum-free media simplifies the purification of the produced mAb in contrast to serum-supplemented medium. Serum-free media is free of BSA and bovine immunoglobulins (e.g. IgG), facilitating purification of mAb. The cells must be adapted from serum-containing medium (D-MEM, 15% FBS, 1% MEM-NEA) to serum-free conditions by stepwise reduction of the serum concentration to ensure a high cell vitality and antibody production rate. Therefore the cells should be in mild-logarithmic growth phase with viability over 90% prior to adaption. Following different serum-free media and protein-free media were tested (see Table 2).

TABLE 2

Tested serum-free media and protein-free media for hybridoma cell cultivation

| Media | Description | Protein content | Company |
|---|---|---|---|
| Hybridoma Express | serum-free | Low, 11 µg/ml | PAA |
| Hybridoma Express Plus | serum-free | Low (not specified) | |
| CD Hybridoma Medium | protein-free | No proteins or peptides | GIBCO |
| Hybridoma-SFM | serum-free | Low, 20 µg/ml | |

All tested media were supplemented with 0.5% gentamicin. Immediately before use of culture medium, 50 µM β-mercaptoethanol and 2 mM L-glutamine were added. Parallel to the serum-free media adaption also culture media (D-MEM, 1% MEM-NEA) with 15% Ultra low IgG-FBS (Invitrogen) containing less than 5 µg/ml IgG were tested. Due to the presence of FBS the cells were directly adapted to the culture media. Therefore the cells were subcultured with a seeding density of $4\times10^5$ living cells/ml into culture medium with 15% Ultra low IgG-FBS. The further subculture of cells was routinely performed dependent on cell density twice per week.

The hybridoma cells were cultivated in 175 cm² T-flask at 37° C. and in a humidified atmosphere of 5% $CO_2$.

1.1.8 Preparation of Growth Curves

Growth curves over seven days were created for long term analysis of hybridoma cell growth in serum-free and serum-containing media. The hybridoma cells were cultivated in shake flasks. Therefore a 125 ml-shake flask was inoculated with a working volume of 30 ml cell suspension at 37° C., 5% $CO_2$ and was shaken at 80 rpm. Regularly a 300 µl sample was obtained from the shake flask for the determination of cell number and antibody concentration in cell culture supernatant. For the media optimization serum-containing media with 15% FBS or 15% Ultra low IgG-FBS (Invitrogen) and serum-free as well as protein-free media from the companies PAA and GIBCO were tested.

1.2 Antibody Purification
1.2.1 Affinity Chromatography

The mAb enriched in the hybridoma cell culture supernatant was purified using affinity-chromatography. Therefore a HiTrap Protein G HP (5 ml) column with recombinant protein G coupled to 6% cross-linked dextran support material (GE Healthcare, Uppsala) was used. Protein G, a cell surface protein of Group G streptococci bacteria, is a Type III Fc receptor that binds to the Fc region of mammalian IgG by a non-immune mechanism. The Fc receptor has also a binding region for albumin. But the albumin binding site is genetically deleted from recombinant form of protein G, thereby avoiding unwanted cross-reactions with albumin and so the purification of antibodies from FBS containing cell culture supernatant is possible. However, protein G binds beside mouse-IgG also bovine-IgG. On this account for the cultivation of hybridoma cells Ultra low IgG-FBS (Invitrogen) containing less than 5 µg/ml IgG was used and also serum-free and protein-free media was tested for hybridoma cultivation.

The affinity chromatography was performed at Äkta™Purifier (GE Healthcare). At first the column was rinsed with degassed bi-distilled water to remove the preservative ethanol. The whole column was cooled at 4° C. Then the protein G column was equilibrated with 1× binding buffer (20 mM $Na_2HPO_4$, pH 7.0) to ensure the optimal pH 7 and suitable ionic strength for the antibody binding. The cell culture supernatant was centrifuged at 38400×g (Avanti J-30I, BECKMAN COULTER) at 4° C. and 30 min to remove remaining cell fragments. For the chromatography the cell culture supernatant was mixed 1:1 with 2× binding buffer (40 mM $Na_2HPO_4$, pH 7.0). The application of the probe at the column was performed with the sample application pump of Äkta™Purifiers P-950 with a flow of 1.5 ml/min overnight, whereby the supernatant was ice cooled. Thereby the maximal allowed total pressure should not exceed 0.3 MPa because excessive pressure could destroy the gel bed of the support material. Following this, excess and unspecific components were washed from the column with binding buffer, followed by a gradient of 0 to 2 M NaCl over 5 column volumes. Afterwards the column was washed again with 1× binding buffer. Two different methods were tested to elute the antibodies from the column. The protein was eluted in reverse flow of 2.5 ml/min and the fraction was collected with increasing absorption at 280 nm. The first elution method was performed with acidic 0.1 M glycine-HCl solution (pH 2.7) by buffer switch. Due to the pH alteration the bound immunglobulins were released from the protein G and were then collected. After elution the pH in the elution fraction was immediately neutralized by titration with 1 M Tris-HCl, pH 9.0. The column was rinsed with 1× binding buffer to equilibrate the column to pH 7.0. The second method was performed with a gradient of 0 to 2 M potassium thiocyanate (KSCN) over 5 column volumes, whereby the pH remains constant at 7.0. The interactions between the antibody and protein G were loosened through KSCN. After elution the column was rinsed with 1× binding buffer.

Afterwards the antibody solution was immediately dialysed to exchange the buffer.

1.2.2 SDS-Polyacrylamidgelelectrophoresis (SDS-PAGE)

The SDS-Polyacrylamidgelelectrophoresis is used to separate proteins according to their molecular weight in electrical field. With the detergent SDS (sodium dodecyl sulfate) the intrinsic charges of polypeptides were overlaid through the accumulation of SDS at the polypeptide (approx. 1 molecule per 1.6 amino acids). Thereby the electrophoretic mobility depends widely on the molecular weight of the protein. For the reduction of the proteins the probes were diluted with SDS sample buffer (Roti®-Load 1, Bio-Rad) in proportion 1:3 (v/v) and incubated for min at 95° C. The SDS sample buffer contains β-mercaptoethanol reducing disulfide bonds of proteins and cause the separation of heavy and light chains of antibodies. Samples which should not be reduced were diluted with sample buffer (250 mM Tris-HCl pH 8.0, 5% (w/v) SDS, 50% (v/v) glycerin, 0.005 (w/v) bromophenol blue) containing no β-mercaptoethanol. The buffer was diluted in proportion of 1:4 (v/v) with the sample. Before application of the sample to a polyacrylamide gel, the probes were slightly shaken at 30° C. for 30 min. In the present work, fractions of affinity chromatography (see chapter 1.2.1) were examined in SDS-PAGE for testing of the presence and purity of the antibodies to be analyzed. The separation of proteins was performed in 12% polyacrylamide gel (composition see Table 3). The electrophoresis was performed in a vertical cutting chamber, filled with 1× running buffer (30.3 g/l Tris, 10 g/l SDS, 144 g/l glycine) and started with 100 V for 10 min and then increased to a constant voltage of 200. Beside the probes, a pre-stained protein ladder (10-250 kDa, Fermentas) was applied as molecular weight reference.

The proteins were stained with Coomassie Brilliant Blue-G250 for 30 min. Following this, the gel was destained with 10% acetic acid over several hours.

TABLE 3

Composition of stacking- and separation gel for SDS-PAGE

| components | Stacking gel (3%) | Seperation gel (12%) |
|---|---|---|
| $H_2O$ | 4.85 ml | 3.95 ml |
| Stacking gel buffer (500 mM Tris/HCL, pH 6.8) | 1.85 ml | — |
| Separation gel buffer (1.5M Tris/HCL, pH 8.8) | — | 2.8 ml |
| Acrylamide | 0.75 ml | 4.5 ml |
| 10% APS | 40 µl | 60 µl |
| 10% SDS | 150 µl | 225 µl |
| TEMED | 12 µl | 18 µl |

1.2.3 Dialysis and Upconcentration of Proteins

The dialysis was used for the transformation of antibody solution in storage buffer (D-PBS with 2 mM EDTA (pH 7.13)) by using the semi permeable properties of dialysis membrane. After antibody purification with affinity chromatography the elution fraction containing antibodies were dialysed. At first the dialysis tube was soaked in distilled water to achieve semi permeability, flexibility of the tube and to remove preservation agents. The dialysis tube with a cut-off threshold of 6-8 kDa was filled with the antibody solution and suspended in storage buffer. Following this, the antibody solution was dialyzed over night at 4° C. under constant stirring against 100-fold volume of sample. Afterwards the concentration was determined with UV/VIS spectroscopy. The antibody solution was up-concentrated to at least 2 mg/ml using VIVASPIN 20 ml CONCENTRATOR"-tubes of the company VIVASCIENCE with cut-off threshold of 5 kDa. The antibody solution was centrifuged at 4° C. and 3500×g in a Swing-Out-Rotor from Sigma. Finally, the antibody was dialyzed against D-PBS with 2 mM EDTA (pH 7.13).

1.2.3.1 Biotinylation of Antibody

The biotinylation of the mAb mouse anti Aβ11(pE) (clone 13) was required for the application in Aβ11(pE) ELISA as antibody to detect specifically Aβ(pE11-x) peptides in biological samples. For the detection a streptavidin-peroxidase polymer was added to the biotinylated antibody whereby a strong non-covalent interaction between streptavidin and biotin was formed.

The biotinylation was performed with concentrated antibody (see section 1.2.3). At first the purified and concentrated mAb was dialyzed against biotinylation buffer (100 mM $NaH_2PO_4$, 150 mM NaCl, pH 7.2) at 4° C. over night. Afterwards the protein concentration was determined via UV-spectrum (see section 1.3.1). The biotinylation agent ($NHS-PEO_4$-Biotin) was dissolved in distilled water to prepare a 20 mM solution. The reaction was performed in a molar ratio antibody:biotin of 1:6 and incubated at 4° C. for 4 h. The reaction between antibody and activated biotin was stopped with the addition of 1 M Tris buffer pH 9.0 with 50-fold excess referred to the amount of the reaction mixture and then incubated at 4° C. for 1 h. The antibody-biotin solution was twice dialysed against dialysis buffer (D-PBS, 2 mM EDTA) at 4° C. over two days and the protein concentration was determined via UV-spectrum (see section 1.3.1). For the estimation of incorporated biotin level 100 μl HABA-Avidin solution was added to 800 μl dialysis buffer, incubated in the measuring cuvette for 10 min and then $A_{500}$ with UV-Spectrometer UV1 was measured. After that 100 μl antibody-biotin solution was added to the solution in cuvette, mixed and the absorption $A_{500}$ was measured again when the value remains constant for at least 15 seconds. The biotin forms a complex with avidin resulting in reduction of absorption at 500 nm. The level of biotin incorporation (moles of biotin per mole of protein) was then calculated.

1.3 Methods for Biophysical Characterization of Antibodies 1.3.1 UV/VIS-Spectroscopy After the purification of anti Aβ11(pE) antibody, the UV/VIS spectrum was determined. For the determination of the protein concentration, the absorption at 280 nm and also the UV-spectrum between 240 nm and 339 nm was measured with the UV-Spectrometer UV1 of Thermo Scientific. The protein concentration was determined by the absorption $A_{280}$ and the extinction coefficient. An extinction coefficient of $\epsilon=1.5$ was assumed for the anti Aβ11(pE) antibody.

1.3.2 Determination of Thermodynamic Protein Stability Via CD-Spectroscopy

The purified anti Aβ11(pE) antibody was dialysed against 10 mM $NaH_2PO_4$ (pH 7.14). The concentration was determined by UV/VIS spectroscopy (see section 1.3.1). For CD-spectroscopy the antibody was diluted to a concentration of 0.13 mg/ml and filled in a quartzglass cuvette (d=0.1 cm). The CD-spectrum was measured with the Jasco J-710 spectro-polarimeter (Jasco GmbH, Groβ-Umstadt) between 190 and 260 nm. The spectra at temperature of 20° C. were measured with 20 accumulations. Then the temperature was increased from 20° C. up to 80° C. whereby the ellipticity was measured at 5° C. interval with 10 accumulations. The heat rate was 30 K/h and the temperature was equilibrated 180 s before each measurement.

1.3.3 Surface Plasmon Resonance (SPR)

1.3.3.1 Immobilization of Ligand on CM5 Chip

The synthesized Aβ(pE11-30) peptide, stored in hexafluoroisopropanol (HFIP) at −80° C., was thawed at room temperature. The tube containing the peptide was left open under a fume hood over night to evaporate the solvent HFIP. With 10 mM sodium acetate pH 5 the peptide was diluted to a concentration at 1 mg/ml.

The used CM5 chip has a carboxylated dextran matrix. For coupling of the peptide Aβ(pE11-30) the amine coupling method was used. It was required to activate the sensor chip surface before peptide coupling. Therefore activation reagents 0.4 M 1-ethyl-3-(3-dimethylamino-propyl)-carbodiimide (EDC) and 0.1 M N-hydroxysuccinimide (NHS) were mixed at a ratio 1:1 and injected with 10 μl/min for 8 min at CM5 chip. Then the coupling of peptide followed. At first 10 μg/ml peptide Aβ(pE11-30) in 10 mM potassiumdihydrogenorthophosphate pH 6 was injected with a flow rate of 10 μl/min for 5 min. Because of the low signal rise the peptide was applied again with a higher concentration diluted in a solution with pH 5. 50 μg/ml peptide Aβ(pE11-30) in 10 mM sodium acetate pH 5 was injected with a flow rate of 10 μl/min for 20 min. A mild acid pH was chosen for coupling to provide a pre-concentration of the peptide (positive net charge) at the sensor surface (carboxyl group negative net charge) by electrostatic attraction. The covalent bond of the peptide was formed by the reaction of the two amino acids lysine (at peptide position 16 and 28) with the activated carboxyl group at chip surface. Excess reactive ester groups were deactivated with 1 M ethanolamine pH 8.5 with a flow rate of 10 μl/min for 10 min. Non-immobilized peptides were removed by injection of 0.1 M HCl (3×10 μl) and subsequently the chip was rinsed over night with running buffer. At the end the signal was about 1000 Response Units (RU) whereby the chip surface was saturated with the peptide. Hence, the coated chip was used for determination of antibody content anti Aβ11(pE) out of cell culture supernatant.

1.3.3.2 Quantification of Anti Aβ11(pE) Antibodies

For the measurement of anti Aβ11(pE) antibody concentration a CM5 chip, which was coated with Aβ(pE11-30) was used. The chip surface was saturated with the peptide and the signal was about 1000 Response Units (RU) (see section 1.3.3.1). The mAb containing in cell culture supernatant were appropriately diluted in running buffer (HEPES EDTA buffer (HBS-EP), Biacore) for antibody analysis. At first the flow cells of sensor chip were rinsed with running buffer. Afterwards the antibody solution with anti Aβ11(pE) was injected with a flow rate of 30 μl/min over 300 s to characterize the association of the antibody at the antigen. An unmodified flow cell was used as reference, which should only show unspecific interactions of the antibody with the matrix. Afterwards the running buffer was automatically injected again by switch-over valve to induce the dissociation of the antibody. Finally the chip was regenerated by injection of 0.1 M HCl (10 μl), whereby the remaining antibody was removed from the sensor surface.

The evaluation of the binding was performed with the program BIAevaluation (Biacore, Freiburg).

For the quantification of antibody concentration in samples of cell culture supernatant, a standard curve with known concentrations determined by UV/VIS spectroscopy of the purified and dialysed mAb from hybridoma clone 13 was measured. The mAb was purified as described in section 1.2.1. For the highest standard concentration, 10 µg/ml mAb was applied and diluted in running buffer down to the lowest concentration of 0.04 µg/ml by performing a radix two division.

1.3.3.3 Determination of Cross Reactivity by SPR

The cross reactivity of anti Aβ11(pE) antibody (clone 13) to pyroglutamate-peptides Aβ3(pE), Aβ11(pE), CCL2 (known as MCP-1), CCL8 (known as MCP-2), big gastrin, gonadoliberin, neurotensin, orexin A, fibronectin, collagen 1 and TRH (thyrotropin-releasing hormone) was tested via SPR. Therefore CM5 chips with a high concentration of immobilized pyroglutamate peptides were used. Antibody clone 13 was diluted in running buffer and injected with 1 µg/ml, a flow rate of 30 µl/min over 300 s.

1.3.4 Isothermal Titration Calorimetry (ITC)

1.3.4.1 Determination of Thermodynamic Parameters

With ITC, the thermodynamic parameters of the binding of anti Aβ11(pE) antibody from clone 13 at antigen Aβ11(pE) was determined. For the ITC experiment, the peptide Aβ(pE11-18)-PEG was used because the hydrophilic PEG group imparts hydrophilic properties and so it was possible to dissolve the peptide directly in ITC buffer. Former experiments with Aβ(pE11-20) could only be performed with 1-2% DMSO, due to the strong hydrophobicity of the peptide it was necessary to dissolve it with DMSO which could have an effect on the ITC binding properties. At first the antibody was dialyzed against ITC buffer (150 mM NaCl, 25 mM $Na_2HPO_4$, 25 mM $KH_2PO_4$, 1 mM EDTA, pH=7.1) over night at 4° C. The lyophilised peptide, stored at −20° C., was dissolved in identical ITC buffer pH=7.1 which was used for antibody dialysis. Both antibody and antigen must be in identical solutions, otherwise large heats of dilution will mask the desired observation. Before the ITC experiment, the concentration of antibody was determined by UV/VIS spectroscopy (see section 1.3.1). At first the antibody with e.g. 5.13 µM (see Table 4) was added into the sample cell and the reference cell was filled with distilled water. Then the antigen was injected into the sample cell with e.g. 81.78 µM (see Table 4). The antigen should be generally in twofold excess to the antibody, bearing in mind that an antibody has two binding sites the antigen was in the cell at least in fourfold excess to the antibody. The 30 injections (1×2 µl and 29×10 µl) were made with a 4-min interval between subsequent injections. The measurement of heat of reaction was performed at 20° C. Furthermore the heat of reaction was determined which was only generated by dilution of the antigen through the titration into ITC buffer (pH=7.1). Therefore the antigen was injected into the sample cell filled with ITC buffer. The heat of reaction which was generated during the titration of the antigen to the antibody was corrected about this value. The analysis of raw data and the determination of the association constant ($K_A$), reaction stoichiometry (n), binding enthalpy (ΔH) and entropy (ΔS) was performed with Origin Software of Micro-Cal.

With ITC the binding parameters of anti Aβ11(pE) antibody eluted from protein G column with KSCN-gradient (pH 7.0), with 0.1 M glycine-HCl (pH 2.7) and also the biotinylated antibody were analyzed. In Table 4 the used antigen and antibody concentrations are listed.

TABLE 4

Concentrations of Aβ(pE11-18)-PEG peptide and anti Aβ11(pE) antibody in ITC
Used concentrations of the eluted antibody with KSCN-gradient (pH 7.0) and 0.1M glycine-HCl (pH 2.7) from protein G column, respectively and of the biotinylated anti Aβ11(pE) antibody.
The interaction of Aβ(pE11-18)-PEG peptide and the three antibodies were analyzed in ITC.

| | Concentrations (µM) in ITC | | |
|---|---|---|---|
| | $1^{st}$ ITC experiment | $2^{nd}$ ITC experiment | $3^{th}$ ITC experiment |
| Anti Aβ11(pE) antibody | 5.13 (KSCN eluted) | 686.31 (Glycine-HCl eluted) | 101.8 (Biotinylated) |
| Aβ(pE11-18)-PEG peptide | 81.78 | 32.85 | 5.12 |

The glycine-eluted anti Aβ11(pE) antibody was applied in a higher concentration than the KSCN eluted antibody due to the presumption that the antibody was partly inactivated by acidic elution.

1.4 Application of Monoclonal Anti Aβ11(pE) Antibodies 1.4.1 Study PBD-0316

Plasma and serum samples from AD patients (n=13) and 30 healthy controls were analyzed in the present study. The 43 analyzed samples come from the initial study and were recruited through a CRO (GALMED GmbH). The samples originated from patients with a clinical diagnosis of AD and from control groups. In a prestudy examination the neuropsychological functions of all participants of the study were tested by several psychometric tests (DemTect, Mini-Mental-State Test, Clock-drawing test). The DemTect scale is a brief screening test for dementia comprising five short subtests (10-word list repetition, number transcoding, semantic word fluency task, backward digit span, delayed word list recall) (Kessler et al., 2000, Psycho 26 343-347). The Mini-Mental State Examination (MMSE) or Folstein test is a brief 30-point questionnaire test that is used to assess cognition. It is commonly used in medicine to screen for dementia. In the time span of about 10 min it samples various functions including arithmetic, memory and orientation. The test includes simple questions and problems in a number of areas: the time and place of the test, repeating lists of words, arithmetic, language use and comprehension, and basic motor skills.

Scoring of the clocks (Clock-drawing test) was based on a modification of the scale used by Shulmann et al., 1986. All circles were predrawn and the instruction to the subjects was to "set the time 10 after 11".

After prestudy examination the study started 2 weeks later with blood withdrawal from all participants, defined as time point zero. All blood samples for the determination of AD biomarkers were collected into polypropylene tubes (Sarstedt Monovette) containing potassium-EDTA for EDTA plasma and blank for serum. All samples were collected by venous puncture or by repeated withdrawal out of an inserted forearm vein indwelling cannula and centrifuged with 1550 g (3000 rpm) for 10 min at 4° C. to provide plasma. Samples were centrifuged within one hour after blood withdrawal. Plasma or serum of each separate sample was pipetted off, filled in one 5 ml polypropylene cryo-tube and stored frozen at −80° C. After 3; 6 and 12 months blood was again withdrawn from all participants and handled as described above.

1.4.2 Auto-Ig ELISA
1.4.2.1 Performance and Establishment of Auto-Ig-ELISA Auto-Ig-ELISA's were performed and established for the analysis of auto-immunglobulins in plasma samples from Alzheimer's disease (AD) patients and healthy controls. Especially auto-immunglobulins against pE-N-terminus of Aβ peptides and Bri2 peptides should be tested. The auto-Ig-ELISA is constructed according to the principle of the direct sandwich-ELISA. Therefore streptavidin coated microplates (Thermo Scientific) were used for immobilization of peptides Aβ(pE3-12); Aβ(pE11-20) and Bri2 (1-23) which are biotinylated at the C-terminus. At first the streptavidin plate was three times washed with 300 µl wash buffer (25 mM Tris, 150 mM NaCl, 0.05% Tween, 0.1% BSA) to clear the plate and remove preservative agents. Afterwards 100 µl peptide solution with 200 ng/ml was added and incubated at room temperature (RT) for 2 h. The microplates (MTP) were masked with a cover sheet to prevent evaporation during the incubation time. The MTPs were blocked with 200 µl/well ELISA-Blocker without Tween 20 (ELISA-Blocker (−T)) and incubated for 1 h at RT. Following this, unbound peptides were removed by three times washing with 300 µl wash buffer. The EDTA-plasma samples were appropriately diluted in ELISA-Blocker+Tween 20 (ELISA-Blocker (+T)). For the calibration curve, mAb were diluted in ELISA-Blocker (+T) or wash buffer by performing a radix two division. The diluted standard and EDTA-Plasma samples were transferred into MTP with 100 µl per well. Dependent on the amount of determination the samples and calibrators were pipetted into several wells. After an incubation time of 2 h at 4° C., a new wash cycle followed (three times wash buffer with 300 µl/well). Polyclonal rabbit anti-mouse Ig's conjugated with Horse Radish Peroxidase (HRP) were used for the detection of the calibrator. Polyclonal anti-human Ig's, IgG, IgG2, IgG3. IgM or IgA conjugated with HRP were used as enzyme-conjugate solution for the detection of auto-immunglobulins out of EDTA-Plasma. The enzyme conjugate solutions were diluted with ELISA-Blocker (+T) to a concentration of 1 µg/ml. In each well 100 µl of enzyme-conjugate solution was pipetted and incubated for 1 h at 4° C. A wash cycle (three times wash buffer with 300 µl/well) followed. The peroxidase substrate solution Sure Blue (company KLP) containing Tetramethylbenzidin (TMB, chromogen) and hydrogen peroxide (substrate) was added with 100 µl/well. The HRP catalyses the decomposition of two hydrogen peroxide molecules to water and oxygen, whereby two electrons from the amino groups of the chromogen TMB are transferred at the substrate. The release of electrons from TMB (oxidization) leads to a radical cation which is stabilized through dimerisation and exhibits the typical blue color. So the color of the chromogen is changed from colorless to blue through the electron transfer. The color intensity of the solution is proportional to the analyte concentration. After the incubation of 30 min at RT the enzymatic reaction was stopped with 1 M $H_2SO_4$ solution by inactivation of the peroxidase and the dimerisation of TMB is abolished. After the disproportion the intensive yellow colored divalent cation was formed. The absorption was measured at a wavelength of 450 nm corrected by absorbance at 540 nm. The absorption at 450 nm and 540 nm was measured with the TECAN Sunrise plate reader.

The anti Aβ3(pE), anti Aβ11(pE) and anti Bri2 (1-23) ELISA were completely established according the described protocols (see Table 5). For the establishment of the ELISA's the standard protocol of the manufacturer (Thermo Fisher Scientific) was used as a model. After the optimization of different parameters such as the concentration of immobilized antigen, detection antibody and incubation times- and temperatures as well as wash cycles the followed protocols were prepared.

TABLE 5

Performance of auto-Ig-ELISA's

| Auto-Ig-ELISA | Anti Aβ3(pE) | Anti Aβ11(pE) | Anti Bri2 (1-23) |
|---|---|---|---|
| Microplate | Maxisorp Streptavidin | | |
| Wash cycle | 3 × 300 µl/well wash buffer | | |
| Immobilized antigen | Aβ(pE3-12) biotin 200 ng/ml, 100 µl | Aβ(pE11-20) biotin 200 ng/ml, 100 µl | Bri 2 (1-23)biotin 200 ng/ml, 100 µl |
| | Diluted in wash buffer | | |
| Incubation | 2 h, RT | | |
| Blocking | 200 µl ELISA-Blocker (−T) | | |
| Incubation | 1 h, RT | | |
| Wash cycle | 3 × 300 µl/well wash buffer | | |
| Analyte | Human anti Aβ3(pE), 100 µl | Human anti Aβ11(pE), 100 µl | Human anti Bri2, 100 µl |
| Standard | mAb mouse anti Aβ3(pE) (clone 6), 100 µl | mAb mouse anti Aβ11(pE) (clone 13), 100 µl | No mAb is available |
| Dilution Analyte, Standard | ELISA-Blocker (+T) | | |
| Incubation | 2 h, 4° C. | | |
| Wash cycle | 3 × 300 µl/well wash buffer | | |
| Detection | Polyclonal rabbit anti-mouse Ig's (HRP) for standard, 100 µl | | |
| | Polyclonal anti-human Ig's, IgG, IgG2, IgG3. IgM or IgA (HRP) for plasma sample, 100 µl | | |
| Incubation | 1 h, 4° C. | | |
| Wash cycle | 3 × 300 µl/well wash buffer | | |
| Substrate/ Chromogen | $H_2O_2$/TMB (Sure Blue), 100 µl, 30 min at RT in the dark | | |
| Stop solution | 1M $H_2SO_4$, 100 µl | | |

Measurement of OD at 450/540 nm at TECAN Sunrise

After establishment of auto-Ig-ELISA's, plasma samples from AD patients and healthy controls were tested. Therefore 13 plasma samples from AD patients and 30 healthy controls were analysed. The plasma samples originated from patients with a clinical diagnosis of AD/MCI and from healthy control groups. The 43 plasma samples come from the study PBD-0316 performed in cooperation with GalMed Medical Research Company. Plasma samples collected after 6 months (T0+6) were used. To the plasma samples protease inhibitor and EDTA were added to prevent protein degradation and to conserve the samples. Therefore to 1 ml plasma 25 µl protease inhibitor solution was added. For the protease inhibitor solution a tablet of protease inhibitor Complete Mini were solved in 1 ml PBS. Afterwards the samples were aliquoted and stored at −80° C. to guarantee a constant quality of analyzed plasma.

1.4.3 Establishment of Aβ(pE11-x) ELISA

Aβ(pE11-x) ELISA should be established for the analysis of Aβ(pE11-x) peptides in cerebrum of e.g. mice models. The detection of pyroGlu Aβ peptides in plasma or CSF isn't possible due to the high aggregation tendency the passage of oligomers through the blood-cerebral-barrier is impaired.

The Aβ11(pE) ELISA was constructed according to the principle of sandwich ELISA and as model the classical protocol of Aβ3(pE) ELISA was applied. Commercially available monoclonal mouse anti Aβ(17-24) antibody (clone 4G8, Covance) was used as capture antibody adsorbed to the surface of the microplate. The monoclonal biotinylated anti Aβ11(pE) antibody bound to captured Aβ(pE11-x) were detected by addition of streptavidin-HRP (SA-HRP) conjugate. The establishment was performed with synthesized Aβ(pE11-30) and Aβ(pE11-40) peptide. The Aβ peptide stored in hexafluoroisopropanol (HFIP) at −80° C. was thawed at room temperature. The tube with the peptide was left open under a fume hood to evaporate the solvent HFIP. The peptides were dissolved in 100 mM NaOH, incubated for 10 min at RT and were diluted in EIA-buffer which contains 0.05% Tween and 1% BSA. The Aβ(pE11-x) ELISA was performed according the described protocol in Table 6.

TABLE 6

Performance of sandwich Aβ(pE11-x) ELISA

| | Sandwich Aβ(pE11-x) ELISA |
|---|---|
| Microplate | Maxisorp |
| Capture antibody | Mouse anti Aβ(17-24) clone 4G8, 2 μg/ml in D-PBS pH 7.4, 100 μl/well |
| Incubation | Over night, 4° C. |
| Blocking | ELISA-Blocker (−T), 200 μl/well |
| Incubation | 2 h, RT |
| Wash cycle | 6 × 300 μl/well protein free blocking buffer (TBS) + 0.05% Tween 20 (PIERCE)TBS-T |
| Preparation Analyte | Evaporate solvent HFIP. Solved peptide in 100 mM NaOH (incubate 10 min at RT), diluted in EIA-buffer |
| Analyte | Aβ(pE11-30) or Aβ(pE11-40) concentration range 800 pg/ml to 12.5 pg/ml, 100 μl/well |
| Incubation | 2 h, RT |
| Wash cycle | 6 × 300 μl/well TBS-T |
| Pre-incubation mAb and SA-HRP | Mix detection antibody with SA-HRP conjugate, incubate 10 min at RT, dilute with ELISA-Blocker (+T) to end concentration |
| Detection | 1 μg/ml mAb mouse anti Aβ11(pE)-Biotin, 2 μg/ml SA-HRP, 100 μl/well |
| Incubation | 1 h, 4° C. |
| Wash cycle | 6 × 300 μl/well TBS-T |
| Substrate/Chromogen | $H_2O_2$/TMB (Sure Blue), 100 μl, 30 min at RT in the dark |
| Stop solution | 1M $H_2SO_4$, 100 μl |

Measurement of OD at 450/540 nm at TECAN Sunrise

In addition to the sandwich ELISA a direct ELISA with adsorbed antigen Aβ(pE11-30) at microplate was performed to test directly the monoclonal anti Aβ(17-24)-biotin antibody (clone 4G8) and the monoclonal anti Aβ11(pE)-biotin antibody (clone 13). The biotinylated antibodies were detected by addition of streptavidin-HRP (SA-HRP) conjugate. The established protocol of direct ELISA was shown in Table 7.

TABLE 7

Performance of direct Aβ(pE11-x) ELISA

| | Direct Aβ(pE11-x) ELISA |
|---|---|
| Microplate | Maxisorp |
| Preparation antigen | Evaporate solvent HFIP over night. Solved peptide in 100 mM NaOH (incubate 10 min at RT), diluted in PBS direct at MTP |
| antigen | Aβ(pE11-30) concentration range 500; 250; 100 ng/ml, 200 μl/well |
| Incubation | Over night, 4° C. |
| Blocking | ELISA-Blocker (−T), 250 μl/well |
| Incubation | 2 h, RT |

TABLE 7-continued

Performance of direct Aβ(pE11-x) ELISA

| | Direct Aβ(pE11-x) ELISA |
|---|---|
| Wash cycle | 6 × 300 μl/well protein free blocking buffer (TBS) + 0.05% Tween 20 (PIERCE)TBS-T |
| Incubation | 2 h, RT |
| Wash cycle | 6 × 300 μl/well TBS-T |
| Pre-incubation mAb and SA-HRP | Mix detection antibody with SA-HRP conjugate, incubate 10 min at RT, dilute with ELISA-Blocker (+T) to end concentration |
| Detection | 1 μg/ml mAb mouse anti Aβ11(pE)-Biotin, 2 μg/ml SA-HRP, 100 μl/well |
| Incubation | 1 h, 4° C. |
| Wash cycle | 6 × 300 μl/well TBS-T |
| Substrate/Chromogen | $H_2O_2$/TMB (Sure Blue), 100 μl, 30 min at RT in the dark |
| Stop solution | 1M $H_2SO_4$, 100 μl |

Measurement of OD at 450/540 nm at TECAN Sunrise 1.4.4 Immunohistochemistry

The immunohistochemistry (IHC) images were kindly provided from Qiaoqiao Shi (lab of C. Lemere) of Harvard Medical School in Boston.

With IHC the antigens Aβ(pE11-x) and Aβ(pE3-x) were localized in cerebral tissue sections. Therefore the anti Aβ11(pE) antibody (clone 13) was used for detection of the pyroglu Aβ peptides. For the IHC human cerebral tissue sections of the hippocampus and the frontal cortex from AD patients and furthermore cerebral tissue sections of hippocampus from APP/PS1 transgenic mice were used. APP/PS1 mice currently are used by several laboratories for studies on the mechanisms of amyloid deposition. The mouse model express the Swedish mutation of amyloid precursor protein (APP), shows increased brain Aβ levels followed by development of neuritic plaques. Co expression of mutant presenilin 1 (PS1) increase the Aβ(1-42) generation. The tissue sections were paraffin-embedded and serial cut. The sections were stained with hematoxylin to colored nuclei of cells and then immunostained with anti Aβ11(pE) antibody. The tissue section preparation and staining were performed in accordance with standard methodology.

1.5 Sequencing Antibody Variable Regions

Cultivation of Hybridoma Cells:

Hybridoma cells were grown in D-MEM (+L-Glutamine, +Na-Pyruvate, 4.5 g/l Glucose, Gibco) with the addition of 15% FBS, 1% MEM-NEA (non essential amino acids, Gibco), 50 μg/ml Gentamycin (Gibco) and 50 μM β-mercaptoethanol at 37° C. and 5% $CO_2$. Subcultivation occurred after 3-4 days depending on cell density. Cells were seeded in a concentration of $0.5\times10^6$ cells/ml, splitting occurred at a cell density of $2\text{-}5\times10^6$ cells/ml.

cDNA Synthesis and Reverse Transcription:

Total RNA was isolated from $2\times10^6$ cells according to the manual of the NucleospinRNA Isolation Kit (Macherey-Nagel). 100 ng RNA were applied for cDNA synthesis by using Oligo $(dT)_{15}$ primer (Promega) and SuperScript III Reverse Transcriptase (Invitrogen).

PCR-Amplification of Heavy and Light Chain Variable Regions:

The heavy chain variable region was amplified from the template cDNA by using Phusion™ High-Fidelity DNA Polymerase (NEW ENGLAND BioLabs) with the primer MHCG1 in combination with primers MHV1 to MHV12. For amplification of the light chain variable region the primer combination MKC with the primers MKV1 to MKV11 was used (see Table 8).

Cloning of PCR Products in pJET1.2:

Heavy and light chain variable regions, amplified by PCR, were cloned into pJET1.2/blunt vector according to the protocol of CloneJET™ PCR Cloning Kit (Fermentas). Sequencing was performed by use of pJET1.2 sequencing primers.

TABLE 8

Primer sequences for PCR-amplification of heavy and light chain variable regions

| Name | Sequence | SEQ ID NO. |
|---|---|---|
| MKV1 | ATGAAGTTGCCTGTTAGGCTGTTGGTGCTG | 26 |
| MKV2 | ATGGAGWCAGACACACTCCTGYTATGGGTG | 27 |
| MKV3 | ATGAGTGTGCTCACTCAGGTCCTGGSGTTG | 28 |
| MKV4 | ATGAGGRCCCCTGCTCAGWTTYTTGGMWTCTTG | 29 |
| MKV5 | ATGGATTTWCAGGTGCAGATTWTCAGCTTC | 30 |
| MKV6 | ATGAGGTKCYYTGYTSAGYTYCTGRGG | 31 |
| MKV7 | ATGGGCWTCAAGATGGAGTCACAKWYYCWGG | 32 |
| MKV8 | ATGTGGGGAYCTKTTTYCMMTTTTTCAATTG | 33 |
| MKV9 | ATGGTRTCCWCASCTCAGTTCCTTG | 34 |
| MKV10 | ATGTATATATGTTTGTTGTCTATTTCT | 35 |
| MKV11 | ATGGAAGCCCCAGCTCAGCTTCTCTTCC | 36 |
| MKC | ACTGGATGGTGGGAAGATGG | 37 |
| MHV1 | ATGAAATGCAGCTGGGGCATSTTCTTC | 38 |
| MHV2 | ATGGGATGGAGCTRTATCATSYTCTT | 39 |
| MHV3 | ATGAAGWTGTGGTTAAACTGGGTTTTT | 40 |
| MHV4 | ATGRACTTTGGGYTCAGCTTGRTTT | 41 |
| MHV5 | ATGGACTCCAGGCTCAATTTAGTTTTCCTT | 42 |
| MHV6 | ATGGCTTGTCYTRGSGCTRCTCTTCTGC | 43 |
| MHV7 | ATGGRATGGAGCKGGRTCTTTMTCTT | 44 |
| MHV8 | ATGAGAGTGCTGATTCTTTTGTG | 45 |
| MHV9 | ATGGMTTGGGTGTGGAMCTTGCTATTCCTG | 46 |
| MHV10 | ATGGGCAGACTTACATTCTCATTCCTG | 47 |
| MHV11 | ATGGATTTTGGGCTGATTTTTTTTATTG | 48 |
| MHV12 | ATGATGGTGTTAAGTCTTCTGTACCTG | 49 |
| MHCG1 | CAGTGGATAGACAGATGGGGG | 50 |

2. Results 2.1 Antibody Screening

Figure 1:
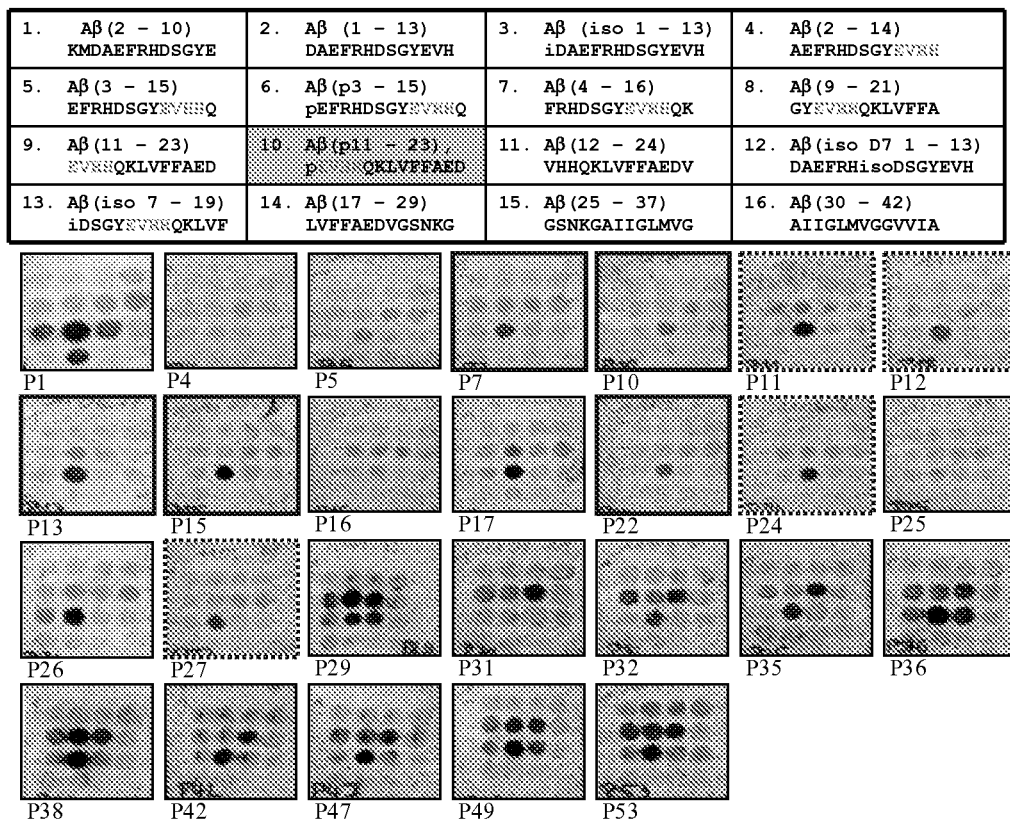
FIG. 1: Screening of anti Aβ11(pE) antibody 26 hybridoma cell supernatants after cell fusion and HAT medium selection were analyzed. The mAb were tested against different modified Aβ peptides containing the sequence EVHH partly. The grey labelled peptide AβpE(11-23) (SEQ ID NO: 19) (see spot 10) contains the target sequence with pyroglutamate at N-terminus (pEVHH). Each membrane was spotted with peptides 1-16. Hybridoma cells of framed membranes (n=9) were selected for recloning. Only the cells of membranes framed with a solid line were stable after recloning. Peptides are as follows: Aβ(2-10) (SEQ ID NO: 10); Aβ(1-13) (SEQ ID NO: 11); Aβ (iso 1-13) (SEQ ID NO: 12); Aβ(2-14) (SEQ ID NO: 13); Aβ(3-15) (SEQ ID NO: 14); Aβ(p3-15) (SEQ ID NO: 15); Aβ(4-16) (SEQ ID NO: 16); Aβ(9-21) (SEQ ID NO: 17); Aβ(11-23) (SEQ ID NO: 18); Aβ(p11-23) (SEQ ID NO: 19); Aβ(12-24) (SEQ ID NO: 20); Aβ(iso D7 1-13) (SEQ ID NO: 21); Aβ(iso 7-19) (SEQ ID NO: 22); Aβ(17-29) (SEQ ID NO: 23); Aβ(25-37) (SEQ ID NO: 24); and Aβ(30-42) (SEQ ID NO: 25).

After the cell fusion and selection of hybridoma cells with HAT medium, the hybridoma cells (originating from several different single cells) were screened to identify cells secreting specific mAb to the target antigen Aβ11(pE). The mAb were examined concerning their ability to bind at different modified Aβ peptides. Thus possible cross-reactions of the mAb with other modified Aβ peptides were determined. The Aβ peptides with the different sequences which were spotted at a hydroxy-cellulose-membrane are shown in FIG. 1. The screening was performed with 26 hybridoma cell supernatants tested versus 16 different Aβ peptides.

FIG. 1 shows 26 membranes (labeled as P1-P53) which were spotted with 16 peptides, illustrated above the membranes. The screening analysis indicated that mAb from hybridoma cells of framed membranes (P7, P10, P11, P12, P13, P15, P22, P24, P27) showed a middle to strong signal against the N-terminal modified Aβ(pE11-23) (pEVH-HQKLVFFAED) peptide (SEQ ID NO: 19) with the target epitope Aβ11(pE). Furthermore, they indicated no significant cross-reactions with other modified Aβ-peptides. The mAb tested on framed membranes also didn't bind at the non-cyclized N-terminal glutamate at position 11 (see spot 9) and no binding signals were detected at spots 4, 5, 6, 7, 8, 9, 13 without the complete Aβ sequence pEVHH at N-terminus. In addition no binding signals at the N-terminal pyroglutamate at position 3 (see spot 6) were detected at the framed membranes. In summary, it can be said that the mAb from hybridoma cells tested on framed membrane pictures were specific for the N-terminal Aβ11(pE) peptide and showed no significant cross-reactions with other sequences of Aβ(1-42) peptide. For this reason the described 9 hybridoma clones were selected for recloning. Five hybridoma clones which are labeled in FIG. 1 with a solid line were stable after recloning and selected for further recloning. Using the limited dilution technique, the selected hybridoma cells were cloned to achieve one isolated clone. In the present work one of these five selected hybridoma clones, named clone 13 was cultivated (see the followed section 2.2) and antibody concentration in the cell culture supernatant was determined.

Hybridoma cells tested at membrane P4, P5, P16, P25, were not selected for recloning because the mAb showed weak or no signals against the target antigen Aβ11(pE) and also against the different Aβ peptides. Furthermore the hybridoma cells of membrane P1, P17, P26, P29, P31, P32, P35, P36, P38, P42, P47, P49 and P53 were not selected for recloning because the mAb showed a strong signal at the target antigen Aβ(pE11-14) as well as at other spotted Aβ peptides and so they indicated no selectivity against the antigen Aβ(pE11-14).

2.2 Cultivation of Hybridoma Cells and Optimization of Cell Culture Media

Preliminary tests were performed with hybridoma cells producing anti Aβ antibodies. During the tests, the optimal cultivation conditions for hybridoma cells producing antibodies against Aβ3(pE) were determined. It was shown that the hybridoma cells cultivated with the medium DMEM supplemented with 15% FBS, 1% MEM-NEAA, 2 mM L-glutamine and 50 μM β-mercaptoethanol have a high proliferation as well as antibody production rate. Therefore, in the present study, the chosen hybridoma clone (clone 13) was cultivated according to the optimized conditions.

It was shown that the hybridoma clone could be successfully cultivated. Within 4 to 6 passages after thawing of hybridoma cells the cell number could be increased 12-fold or 20-fold. The cells formed partly cell aggregates in suspension and also adherent cells could be observed. Vital cells showed a round cell shape and were bigger compared to non-vital cells. The cells were regularly tested for mycoplasma contamination with MycoAlert®Mycoplasma Detection Kit. All tested hybridoma cells were mycoplasma free. During the cultivation time of hybridoma cells the concentration of anti Aβ11(pE) antibodies in cell culture supernatant was measured by SPR (see section 2.2.1). An additional aim of the present study was the adaption of hybridoma cells from serum-containing to serum-free conditions to simplify the purification of the produced mAb. This was performed stepwise. The optimal serum-free medium was identified by preparation of growth curves after media adaption over ten days. Thereby the cell growth and antibody production rate was measured during the cultivation time.

2.2.1 Determination of Antibody Concentration in Cell Culture Supernatant

Figure 2:
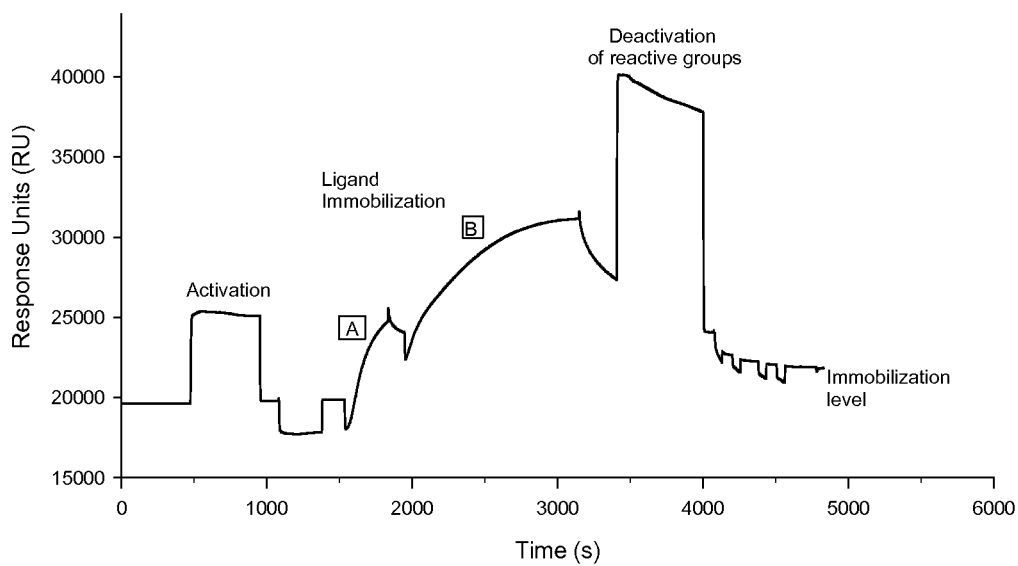
FIG. 2: Coating of CM5 Chip with Aβ(pE11-30)

The concentration of anti Aβ11(pE) antibody out of cell culture supernatant was determined with the principle of surface plasmon resonance (SPR) at the Biacore 3000. Therefore the peptide Aβ(pE11-30) was immobilized at sensor surface of a CM5 chip (see method section 1.3.3.1). In FIG. 2 the immobilization of Aβ(pE11-30) is shown in a real-time plot over time. At first the coupling was performed with 10 μg/ml Aβ(pE11-30). The signal rose up (see FIG. 2, marked A) during the peptide coupling. Because of the low signal the peptide was applied again with a higher concentration of 50 μg/ml (see FIG. 2, marked B). In summary, a high concentration of peptide was immobilized at the chip surface. For the determination of antibody content from cell culture supernatant a high concentration of immobilized peptide was necessary. Thereby, the detection of even low antibody concentrations is possible and also the linear range of the standard curve is higher than with lower concentrations of immobilized peptides. The overload of the chip was not suitable for binding studies and the determination of binding rates like dissociation rate $k_d$ and association rate $k_a$. Due to the high antigen concentration, multiple bond interactions of the antibody are possible (effect of avidity) which leads to wrong binding rates and to an artificially low off rate.

From each cell passage of the cultivated hybridoma clone, the cell culture supernatants were tested for anti Aβ11(pE) antibodies at Biacore 3000. The results of hybridoma clone 13 is shown in FIG. 3. Clone 13 was the only clone which produced anti Aβ11(pE) antibodies. A curve with a high measurement signal (RU) of the antibody from hybridoma clone 13 was determined, which leads to the conclusion that the anti Aβ11(pE) antibody was produced with high yield. In contrast for clone 15, 22 and 24, no specific measurement (RU) signals were obtained during the total cultivation period. For this reason only hybridoma cells of clone 13 were further cultivated and used for all explained experiments in the present study.

For the quantification of antibody concentration within the cell culture supernatant a standard curve with known concentrations of purified anti Aβ11(pE) antibody from clone 13 (see section 1.2) was measured. The measurement signals (RU) by Biacore 3000 were plotted against the antibody concentrations. The standard curve is shown in FIG. 4.

The standard shows a linear course between 0.040 μg/ml and 1.25 μg/ml antibody concentration (see FIG. 5). Above the concentration of 1.25 μg/ml, the curve slope dropped. Due to the high antibody concentration, steric hindrances during the binding of antibody at antigen can occur. The equation of linear regression: y=3033.7x+50.099 ($r^2$=0.991) was used for calculation of antibody concentrations from cell culture supernatant. The further measured samples of cell culture supernatant were diluted that the measurement was within the linear range of standard curve.

2.2.2 Adaption of Hybridoma Cells to Serum-Free Conditions

Hybridoma cells (clone 13) were adapted from serum-containing media (SCM) to different serum-free (SFM) and protein-free media, to simplify the protein G affinity purification of the murine anti Aβ11(pE) mAb from cell culture supernatant. Protein G binds specifically and with high affinity murine immunoglobulin G-molecules. The bovine IgG contained in FBS is also strongly bound from Protein G and undesirable cross-reactions are possible. Therefore serum-free media or protein-free media should be used for the cultivation of hybridoma cells to exclude that bovine IgG is contained in the purified antibody elution fraction.

The media adaption to the different SFM (Hybridoma Express, Hybridoma Express Plus, Hybridoma SFM) and protein-free medium (CD Hybridoma Medium) was performed in T-flasks and after each passage the cell number and the antibody concentration was determined. In Table 9 the cell growth and antibody production after media adaption is shown.

TABLE 9

Cell growth and antibody production after adaption to SFM and protein-free medium
The hybridoma cells (clone 13) were adapted sequentialy in T-flask (37° C., 5% $CO_2$). After the adaption process the cells were cultivated 2 passages and the results of cell growth and anti Aβ11(pE) antibody production (via SPR) were determined.
+ . . . cells proliferate, – . . . no cell proliferation and antibody production, respectively.

| Media | Description | Cell growth | Antibody production |
|---|---|---|---|
| Hybridoma Express | serum-free | + | Very low |
| Hybridoma Express Plus | serum-free | – | – |
| CD Hybridoma Medium | protein-free | + | – |
| Hybridoma SFM | serum-free | + | High |

The results in Table 9 showed that only cells in Hybridoma SFM proliferated and also produced antibodies with high yield. So only the adaption of cells to Hybridoma SFM were successful. For the comparison of cells cultivated in SCM (DMEM, 15% FBS, 1% NEAA and DMEM, 15% low IgG FBS, 1% NEAA) and in Hybridoma SFM, a growth curve over ten days was determined. Therefore, the cells were cultivated in shake flasks and regularly a sample was obtained for the determination of cell number and antibody concentration in the cell culture supernatant (see FIG. 6).

The results demonstrated that cultivated cells in Hybridoma SFM showed a significant, more than twice higher growth compared to cells in SCM. The exponential phase of cells in Hybridoma SFM started at 24 hours whereas cells in SCM started after 48 hours. So the Hybridoma SFM initiated an earlier exponential growth with a shorter lag phase of hybridoma cells compared to SCM. Similarly cells cultivated in SFM and SCM reached the highest cell number after 72 hours. It is noticeable that cells cultivated in SFM showed a dying phase within 72 h and 144 h, which wasn't observed in growth curves of SCM-cultivated cells. Beside the measurement of cell number, the anti Aβ11(pE) antibody concentration was measured. The cells cultivated in SFM showed a significantly higher antibody yield than in SCM. Generally the antibody concentration increased with the rising cell number in the exponential phase, but cells cultivated in SCM stopped the antibody production with the beginning of stationary phase at 72 hours. However, the antibody production of SFM-cultivated cells slightly increase independent of reduced cell number after 72 hours.

To determine specific parameters for the analysis of growth curves, the specific growth rate μ and the production rate $q_p$ were calculated. This data should be serving for better interpretation of growth and antibody production. In FIG. 7 the specific growth rate was plotted against the cultivation time.

At the beginning of cultivation, a high specific growth rate was determined which strongly decreased after the exponential growth phase at 72 hours. The specific growth rate μ was positive until just before 96 hours indicating that the cells had grown. The decline phase of cells was characterized by a negative growth rate because energy sources were consumed after 96 h. It was noticeable that the cells in Hybridoma SFM showed a strong decrease of growth rate after 72 hours due to the very high cell concentration.

Furthermore, the integral of viable cell concentration over the culture time called integral of viable cell density (IVCD) was calculated. The IVCD implies how much cells, by incorporation of time, contribute to the antibody production over the cultivation time. The integral was determined from the curves illustrated in FIG. 6 (A). The measured points of living cell numbers at cultivation time 5 h, 24 h, 48 h and 72 h were fitted by the exponential function $f(t)=a \cdot e^{c \cdot t}$, whereby a and c are constants and t the time. Afterwards the exponential function was integrated. The IVCD were calculated for each time point at 5 h, 24 h, 48 h and 72 h. For the determination of the antibody production rates $q_p$ the antibody concentrations were plotted against the IVCD (see FIG. 8) and from the slope of these curves $q_p$ was obtained. (Renard et al., Biotechnol. Lett. 1988, 10, 91-96; Ozturk et al., J. Biotechnol. 1990, 16, 259-278).

In FIG. 8, only the data points at 5, 24, 48, 72 h were included, because the antibody production rates were strongly reduced in the decline phase and the straight line couldn't correlate the data points of decline and exponential phases. The specific antibody production rate was in exponential phase significantly higher than in stationary phase. These data indicate that the antibody production rate was growth dependent for the hybridoma cell line using in this study. In contrast Ozturk S. described that the specific antibody production rate was constant in both exponential growth and decline phase and so the antibody production of mouse hybridoma cells was not growth associated (Ozturk S. et al. supra).

In Table 10 the obtained specific antibody production rates are shown.

TABLE 10

Specific production rate $q_p$ of hybridoma cells cultivated with SCM and SFM in shake flask

| Media | Antibody production rate $q_p$ (pg Ab/(cells · h)) |
|---|---|
| DMEM, 15% FBS, 1% NEAA | 0.2717 |
| DMEM, 15% low IgG FBS, 1% NEAA | 0.2277 |
| Hybridoma SFM (serum free) | 0.5121 |

The cells cultivated in Hybridoma SFM showed the highest antibody production rate with 0.5121 pg/(cells·h). So the $q_p$ of Hybridoma SFM was approx. twice higher compared to cells cultivated in SCM, possibly due to the twice higher cell proliferation in SFM The hybridoma cells cultivated in SCM were subcultivated several passages and from the passage number 18 the antibody concentration was reduced continuously (data not shown). The antibody production of cells with passage number 27 was totally stopped but the cells showed a normal cell growth independent of reduced antibody production which was also recognized for hybridoma cells producing anti Aβ3(pE) antibodies. Already in literature it was described that hybridoma cells are often unstable and could stop the antibody production. It was determined that hybridoma cells are often present as a mixture of antibody producing and non-producing cells (Heath et al., J Biotechnol. 1990, Vol. 15, S. 71-89). Hybridoma cells which don't produce antibodies may lack genetical integrity concerning the sequences for heavy and light chains. Non-producing cells show a higher proliferation rate than producing cells and could dominate the hybridoma culture after some passages (Kromenaker et al., Biotechnol Prog 1994, Vol. 10, S. 299-307). In contrast, the cells cultivated in Hybridoma SFM still showed a high antibody production rate beyond the passage 27. That suggests that the cells cultivated in SFM showed continuous cell growth as well as antibody production independent to cell passage number. The cultivation of cells in SFM up to higher passage number was performed one time. To make a clear statement, the experiment should be repeated a second time.

Summarizing, the cells cultivated in Hybridoma SFM showed an excellent cell growth with maximum growth rate and display the significant highest antibody production yield with a high specific production rate over the total cultivation time, compared to the cells cultivated in SCM. The used hybridoma cells require only a minor sequential adaption from SCM to Hybridoma SFM. With the use of Hybridoma SFM the cost of hybridoma cultivation could be reduced by 18%, compared to the alternative usage of DMEM with low IgG FBS. Additionally, the purification of mAb from cell culture supernatant was simplified due to the absence of serum containing bovine IgG and other serum components like proteases.

The growth curves of all tested media showed a strong decrease after exponential growth phase at 72 hours, because of the complete consumption of L-glutamine. Miller et al. described that the maximal cell number is enriched when L-glutamine was consumed, because the limitation factor of cell growth is L-glutamine, which is mainly used as energy source and facilitates cell growth and antibody production (Miller et al., 1989, Biotech Bioeng. Vol. 32, S. 947-965). Due to these facts the SCM and also SFM were supplemented with 2 mM L-glutamine. But the cell growth and antibody production was significantly higher for cells in Hybridoma SFM than in SCM.

Hybridoma SFM is a very low-protein medium (20 μg/ml) optimized for hybridoma cell cultivation. The medium contains L-glutamine, trace elements, minerals, and a low amount (20 μg/ml) of defined proteins (insulin and transferrin). Which substances in the SFM were decisive for the high cell proliferation and antibody yield wasn't examined but in the following could be speculated. There are several possibilities to increase the antibody efficiency of hybridoma cells. In the literature it is described that the addition of a lipid mix containing cholesterol, phospholipids and fatty acids enhanced the antibody production of hybridoma cells because the lipid organisation and fluidity of plasma membrane have an influence on cell function (Savonniere et al., Biotechnol. 1996 Jul. 18; 48(1-2):161-73). Also growth factors could increase the antibody production rate, for example epidermal growth factor (EGF), fibroblast growth factor (FGF), interleukin-2 (IL-2), IL-6 (B-cell stimulating factor), transferrin, insulin and ethanolamine (Murakami et al., Proc Natl Acad Sci USA. 1982 February; 79(4):1158-62; Dandulakis et al. Biotechnol Prog. 1995 September-October; 11(5):518-24).

2.3 Antibody Purification

The antibody anti Aβ11(pE) from clone 13 should be purified to homogeneity out of cell culture supernatant to be used in ELISA and additional experiments. The antibody was purified with protein G sepharose column (see section 1.2.1). The bound antibody was eluted according to two different methods. At first, acidic 0.1 M glycine-HCl solution (pH 2.7) was used and the eluted fraction was immediately neutralized through titration with 1 M Tris-HCl, pH 9.0. During the neutralization process the antibody was strongly precipitated because of a possible structure change of the antibody during the acidic elution.

For this reason a pH neutral elution method was performed with a gradient of potassium thiocyanate. Because of KSCN the interactions between the antibody and protein G were loosened. With this technique the antibody was eluted and no precipitation of the antibody occurred. In FIG. 9 the chromatogram of the purification process is shown.

With increased KSCN-gradient the antibody was eluted. The elution peak was almost symmetric like a gaussian function which indicated a homogeneous elution with one antibody species. The elution was induced by the chaotropic ion SCN⁻ which abolishes the protein-protein interactions. A too high concentration of KSCN could denature proteins and therefore the antibody elution was performed in a gradient followed by immediate dialysis. After the affinity chromatography, a SDS-PAGE was performed to examine the content of antibody in the different fractions of protein G column purification (see FIG. 10). Thereby the purity of the elution fraction with anti Aβ11(pE) antibody could be determined. Samples of unpurified cell culture supernatant, flow through fraction, wash fraction and elution fraction of protein G column were analyzed.

The SDS-gel shows that during the protein G purification the specific binding antibody was separated from non specific binding proteins. In the unpurified cell culture supernatant (slot 1; 6) and flow through (2; 7) the BSA-band (bovine serum albumin) with approx. 66 kDa was clearly identified, however the elution fraction (slot 4; 9) contained no BSA. During the wash cycle a small part of the bound antibodies was washed out of the column (slot 3). The elution fraction in slot 4 shows that only the specific binding antibody was eluted. In SDS-PAGE the antibody was separated in the heavy chain with approx. 50 kDa and the light chain with approx. 25 kDa (see slot 4) based on the reducing conditions. To show the total antibody with intact disulfide-bonds, the elution fraction was applied under non-reducing conditions (see slot 9). The antibody was identified with a band at approx. 150 kDa. Furthermore, it was shown that no BSA was holding back in the column and so removed from the purified antibody in the elution fraction. Protein G binds mouse IgG but also bovine IgG which is containing in FBS. To reduce the impurity with bovine IgG, ultra low IgG-FBS (Invitrogen) containing less than 5 μg/ml IgG was used. With this purification method the antibody was purified to homogeneity and separated from all other proteins contained in the cell culture supernatant. After dialysis the antibody concentration was determined via UV-spectrometer and SPR.

During the purification of anti Aβ11(pE) antibody with a protein G sepharose column a sample from cell culture supernatant before application at protein G column, from flow through, wash fraction and elution fraction were taken. This was followed by measurement via SPR. For the quantification of anti Aβ11(pE) antibody by SPR the standard curve which is illustrated in FIG. 10 was used. It was determined that before the purification approx. 14.8 μg/ml antibody was contained in the cell culture supernatant, which is equivalent to a total amount of 26.7 mg antibody in 1800 ml supernatant. The flow through contained 0.8 μg/ml antibody (2.4 mg total) and the wash fraction 8.7 μg/ml (0.2 mg total) antibody. A concentration of 1.07 mg/ml which amounted to 21 mg antibody in the elution fraction was determined via SPR. Subsequently the yield of the affinity chromatography was 80%. After the purification, concentration and dialysis of the antibody the measurement of UV-spectrum was performed (see FIG. 11).

From the UV-spectrum, the antibody concentration with 4.09 mg/ml after purification was determined. Therefore approx. 21 mg antibody out of 1800 ml cell culture supernatant was purified. So the determined antibody concentration by UV/VIS method agreed with the results of SPR. The antibody was then sterile filtered, aliquoted and for further analysis stored at 4° C.

The presented result of antibody purification was performed with cell culture supernatant from cells with high passages (passage 17-22), whereby a reduced antibody production rate above passage 18 was observed (see section 2.2.2). However, the antibody concentration in the cell culture supernatant of cells with lower passage number amounted to approx. 30 μg/ml.

Consequently, antibody purification yield of cells with lower passage number would be twice higher with approx. 42 mg than with the used high cell passages.

2.3.1 Biotinylation of Anti Aβ11(pE) Antibody

The anti Aβ11(pE) antibody was biotinylated for the application as detection antibody in the Aβ(pE11-x) ELISA. The antibody-biotin solution was dialysed to remove non-conjugated biotin. A concentration of 1.88 mg/ml biotinylated antibody (MW 150,000) was determined via UV-spectrum and followed the biotinylation level was determined with HABA assay.

The result was that about 2 biotin molecules were coupled at one antibody. In FIG. 12 the UV/VIS spectrum of the antibody before and after the biotinylation is shown. The two spectra showed the same course of the curve, indicating that no aggregation occurred during the biotinylation process. So the biotinylation was successful and the antibody can be used in combination with streptavidin-HRP polymer as detection antibody.

2.4 Characterization of Anti Aβ11(pE) Antibodies 2.4.1 Sequencing Antibody Variable Regions The following sequences were identified:

2.4.1.1 Clone 13-11-6 (Clone 13)

Aβ Clone 13 variable part light chain nucleotide sequence (SEQ ID NO: 51)

atggagtcacatacccaggttcttatattgctgctgctatgggtatctggtacctgtggggaca ttgtgatgtcacagtctccatcctccctggctgtgtcagcaggagagaaggtcactatgagctg

```
caaatccagtcagagtctgttctacagtagaacccgaaagaactacttggcttggtaccaacag aaaccagggcagtctcctaaattgctgatctactgggcatccactagggaatctggggtccctg atcgcttcacaggcagtggatctgggacagatttcactctcaccatcagcagtgtgcaggctga agacctggcagtttattactgcaagcaatcttacaatctgtggtcgttcggtggaggcaccaag ctggaaatcaaacgggctgatgctgcaccaactgtatccatcttcccaccatccagt
```

Aβ Clone 13 variable part light chain protein sequence
(SEQ ID NO: 52)

```
MESHTQVLILLLLWVSGTCGDIVMSQSPSSLAVSAGEKVTMSCKSSQSLFYSRTRKNYLAWYQQ

KPGQSPKLLIYWASTRESGVPDRFTGSGSGTDFTLTISSVQAEDLAVYYCKQSYNLWSFGGGTK

LEIKRADAAPTVSIFPPSS
```

Aβ Clone 13 variable part heavy chain nucleotide sequence
(SEQ ID NO: 53)

```
atgggatggagctgtatcatgttcttttggtagcaacagctacagatgtccactcccaggtcc aactgcagcagcctgggactgaactggtgaagcctggggcttcagtgaagctgtcctgcaaggc ttctggcttcaccttcaccagctactggatgcactgggtgagacagaggcctggacaaggcctt gagtggattggagagattaatcctagtaacggtcgtactaactataatgagaagttcaagagca aggccacactgactgtagacaaatcctccagcacagcctacatgcaactcagcagcctgacatc tgaggactctgaggtctattactgtgcgagagggatcttgcctgggactggtctgcttactgg ggccaagggactctggtcactgtctctgcagccaaaacgacacccccatctgtctatccactg
```

Aβ Clone 13 variable part heavy chain protein sequence
(SEQ ID NO: 54)

```
MGWSCIMXFLVATATDVHSQVQLQQPGTELVKPGASVKLSCKASGFTFTSYWMHWVRQRPGQGL

EWIGEINPSNGRTNYNEKFKSKATLTVDKSSSTAYMQLSSLTSEDSEVYYCARGDLAWDWSAYW

GQGTLVTVSAAKTTPPSVYPL
```

2.4.2 Determination of Secondary Structure

The secondary structure of biotinylated and non-biotinylated anti Aβ11(pE) antibody was investigated by CD-spectroscopy. Possible changes of secondary structure due to the biotinylation process could be analyzed. The CD-measurement was performed with 130 μg/ml antibody (biotinylated and non-biotinylated) dissolved in 10 mM sodium phosphate pH 7.1. In FIG. 13 the far-UV-CD-spectrum of the antibodies at 20° C. is shown. The spectra of the biotinylated and non-biotinylated antibody were nearly identical and both antibodies showed a minimum at 218 nm and a maximum at 200 nm which is typical for β-sheet proteins. The results indicated that the biotinylation had no influence on secondary structure. The same CD-spectra indicates identical secondary structure and so no influence on binding properties, however this didn't implicate binding properties in ITC or in ELISA.

2.4.3 Temperature Transition of Aβ11(pE) Antibody

Circular dichroism can be used to observe how secondary structure changes with environmental conditions. Thermal protein stability is assessed using CD by following changes in the spectrum with increasing temperature. In FIG. 14 and FIG. 15, the spectra of biotinylated and non-biotinylated anti Aβ11(pE) antibody at temperatures from 20° C. up to 80° C. is shown. From a temperature of 60° C. the course of spectra was changed. The maximum at approx. 201 nm, typical signal for β-sheet proteins, decreased at a temperature of 60° C. and resulted at 80° C. in a minimum. The results indicated that the non-biotinylated as well as the biotinylated antibody began to denature at 60° C. ($T_m \approx 65°$ C.). So the temperature stability of the antibody was given up to 60° C. The results were in the normal range of IgG's and agree with other studies for example S. Frey determined a melting temperature of monoclonal IgG with 63° C. (S. Frey et al., 2008, Biol. Chem., Vol. 389, pp. 37-45). Both antibodies showed in the range of 20° C. up to 60° C. identical CD-spectra with a minimum at approx. 218 nm and maximum at 201 nm, indicating that the biotinylation had no influence on protein stability.

2.4.4 Binding Properties of Aβ11(pE) Antibody

To characterize the binding of anti Aβ11(pE) antibody at the Aβ(pE11-18)-PEG peptide the method of Isothermal Titration calorimetry (ITC) was used (see section 1.3.4). The antibody which was eluted from protein G column with KSCN-gradient (pH 7.0) and 0.1 M glycine-HCl (pH 2.7) was analyzed. With ITC the reaction stoichiometry (N), association constant ($K_A$), binding enthalpy ($\Delta H$) as well as the entropy ($\Delta S$) were determined. The peptide was titrated to anti Aβ11(pE) antibody in the ITC MicroCalorimeter as described in section 1.3.4.2. The titration curve displays the heat per seconds as a function of time (see FIG. 16). The reaction partners interact and heat is released or absorbed in direct proportion to the amount of binding events. Each injection of antigen leads to change of temperature. To compensate the temperature difference between the sample and reference cell the addition or removal of heat to the sample cell occurs and serves as measurement signal.

At first the heat of the Aβ(pE11-18)-PEG dilution in ITC buffer was determined (see FIG. 16, upper trace). The upper trace shows a constant and low signal (background signal) compared to the measurement signal. Afterwards the peptide Aβ(pE11-18)-PEG was titrated to anti Aβ11(pE) antibody in the sample cell (see FIG. 16, lower trace). The total heat release after each injection was determined by integration of the area between each peak and baseline. Then the heat of dilution (see FIG. 16, upper trace) was subtracted from the total heat release of each injection. FIG. 17 shows the obtained binding curve of anti Aβ11(pE) antibody (eluted with KSCN-gradient) with Aβ(pE11-18)-PEG whereby the total heat release at each injection is plotted against the molar ratio of antibody and peptide. From the binding curve the thermodynamic parameters constants were determined with the program Origin 7.0.

In Table 11 the determined parameters N, $K_A$, $K_D$, ΔH, and ΔS as well as the Gibbs energy ΔG for the binding of anti Aβ11(pE) antibody at Aβ(pE11-18)-PEG peptide are shown. Note that $K_D=1/K_A$ and ΔG=ΔH−TΔS.

TABLE 11

Thermodynamic binding parameters of Aβ(pE11-18)-PEG peptide at anti Aβ11(pE) antibody
The antibody was eluted from protein G column with KSCN-gradient (pH 7.0) and 0.1M glycine-HCl (pH 2.7), respectively. The parameters were determined by ITC MicroCalorimeter at 20° C.

| | Anti Aβ11(pE) antibody | |
|---|---|---|
| Binding parameters | KSCN elution | glycine-HCl elution |
| Stoichiometry (N) | 1.88 ± 0.0087 | 1.01 ± 0.0015 |
| Association constant ($K_A$) in $10^6$ $M^{-1}$ | 12.7 ± 1.19 | 9.5 ± 0.52 |
| Dissociation constant ($K_D$) in nM | 78.74 | 105.26 |
| Binding enthalpy (ΔH) in kcal/mol | −8.259 ± 0.058 | −7.999 ± 0.026 |
| Binding entropy (ΔS) in cal/mol × $K^{-1}$ | 4.33 | 4.64 |
| −TΔS kcal/mol | −1.27 | −1.36 |
| Gibbs energy (ΔG) in kcal/mol | −9.53 | −9.36 |

At first the results of anti Aβ11(pE) antibody eluted with KSCN-gradient (pH 7.0) were discussed. The stoichiometry of the antigen and antibody bond was 1.88. So the stoichiometry was almost 2, that means nearly all antibodies were active and interacted with two molecules of Aβ(pE11-18)-PEG peptide. The reason for the stoichiometry variation was the inaccurate concentration determinations due to the unknown antibody absorption coefficients. A stoichiometry with significantly less than two would indicate that a part of antibody molecules are inactive, which is in the case for acidic eluted antibody. The dissociation constant of the antibody was 78.74 nM. For example anti-hMCP1 N1pE(1-x) antibody (data not shown) showed a 3-times higher dissociation constant than anti Aβ11(pE) antibody. That means that the strength of binding of anti Aβ11(pE) was higher than of anti-hMCP1 N1pE(1-x) antibody. However the anti-hMCP1 N1pE(1-x) was successfully used in MCP1 ELISA, which suggests that the anti Aβ11(pE) antibody also should show good binding properties in ELISA. The determined dissociation constant of anti Aβ11(pE) antibody ranged in the middle of described ITC results in literature. For example the interaction of D-PAM (Protein A Mimetic) with monoclonal antibodies IgG showed a $K_D$ in the range of $10^{-5} M^{-1}$ (D'Agostino B. et al., J Immunol Methods. 2008 Apr. 20; 333(1-2):126-38) and the $K_D$ of the interaction between soluble monomeric Aβ(1-40) and mouse monoclonal antibodies were in the range of $10^{-7}$ to $10^{-8}$ $M^{-1}$ (Brockhaus et al., J Phys Chem B. 2007 Feb. 8; 111(5): 1238-43). The $K_D$ of anti Aβ11(pE) antibody amounted 7.8·$10^{-8} M^{-1}$ and was comparable with data described in literature.

In general, antibody and antigen interactions are mostly enthalpic driven by hydrogen bonds (specific interaction) and often the entropy change is negative (ΔS<0) due to the loss of conformational degrees. But from the bond of Aβ(pE11-18)-PEG at anti Aβ11(pE) antibody resulted an mild entropy gain of ΔS=4.33 (cal·$mol^{-1}$·$K^{-1}$), a negative enthalpy with ΔH=−8.259 kcal/mol and a low Gibbs energy with ΔG=−9.53 kcal/mol. So the interaction was mild enthalpic driven (ΔH<0) due to the formation of hydrogen bonds and also mild entropic driven (ΔS>0) which is unusual for antibody and antigen interactions. The bond was characterized by hydrophobic interactions due to the strong hydrophobic epitope Aβ11(pE), water molecules were displaced which resulted in gain of conformational degrees of freedom and so in an mild entropy gain (Ohtaka et al., 2002, Protein Sci. 11, 1908-1916). In contrast, the most antigen and antibody bonds are driven by a negative enthalpy and unfavorable entropy lost e.g. MCP1 N1pE(1-x) antibody.

The above described ITC results were performed with antibody purified with protein G sepharose and eluted with KSCN-gradient (see section 2.3). In addition, the antibody elution was tested with acidic 0.1 M glycine-HCl solution (pH 2.7) followed by immediate neutralization with 1 M Tris-HCl, the antibody was precipitated. Before concentration determination the precipitated protein was removed by centrifugation and does not occur within the ITC experiment. The binding parameters of this acidic eluted antibody were also characterized by ITC. FIG. 18 shows the obtained binding curve of anti Aβ11(pE) antibody (eluted with glycine-HCl) with Aβ(pE11-18)-PEG whereby the total heat release at each injection is plotted against the molar ratio of antibody and peptide.

The results of anti Aβ11(pE) antibody eluted with glycine-HCl showed a dissociation constant of $K_D$=105.26 nM, a negative enthalpy with ΔH=−7.99 kcal/mol and a entropy gain of 4.64 (cal·$mol^{-1}$·$K^{-1}$). The energetic parameters of the acidic and KSCN eluted antibody were nearly the same but in contrast the stoichiometry value of acidic eluted antibody was only 1.01 and so significantly lower than two. That means approx. the half of the antibodies were inactivated due to the acidic elution. In conclusion, the antibody elution was further performed with KSCN-gradient instead with acidic glycine-HCl.

Additionally, the biotinylated anti Aβ11(pE) antibody (see section 1.2.3.1) was also examined in ITC. In Table 12 determined thermodynamic binding parameters are shown.

TABLE 12

Thermodynamic binding parameters of Aβ(pE11-18)-PEG peptide at biotinylated anti Aβ11(pE) antibody
The antibody was biotinylated whereby two biotin molecules were coupled at one antibody. The parameters were determined by ITC MicroCalorimeter at 20° C.

| | Biotinylated anti Aβ11(pE) antibody |
|---|---|
| Stoichiometry (N) | 1.66 ± 0.0092 |
| Association constant ($K_A$) in $10^6$ $M^{-1}$ | 8.0 ± 0.69 |
| Dissociation constant ($K_D$) in nM | 125.00 |
| Binding enthalpy (ΔH) in kcal/mol | −8.276 ± 0.066 |

TABLE 12-continued

Thermodynamic binding parameters of Aβ(pE11-18)-PEG
peptide at biotinylated anti Aβ11(pE) antibody
The antibody was biotinylated whereby two biotin molecules were
coupled at one antibody. The parameters were determined
by ITC MicroCalorimeter at 20° C.

|  | Biotinylated anti Aβ11(pE) antibody |
|---|---|
| Binding entropy (ΔS) in cal/mol × K$^{-1}$ | 3.36 |
| −TΔS kcal/mol | −0.98 |
| Gibbs energy (ΔG) in kcal/mol | −9.26 |

In FIG. 19 the obtained binding curve of biotinylated anti Aβ11(pE) antibody and Aβ(pE11-18)-PEG are shown.

The results of biotinylated anti Aβ11(pE) antibody show nearly the same enthalpy and entropy value but a slightly higher dissociation constant ($K_D$=125 nM) than the non-biotinylated antibody. That means that the binding strength of biotinylated anti Aβ11(pE) was slightly lower than that of non-biotinylated antibody. Also the stoichiometry with 1.66 was under the stoichiometry of non-biotinylated antibody which possibly showed that a low part of antibody molecules are inactive. Concluding, a slight loss of antibody activity, possibly by the biotinylation process was determined.

2.4.5 Determination of Cross Reactivity

The cross reactivity of anti Aβ11(pE) antibody (clone 13) to pyroglutamate-peptides CCL2 (known as MCP-1), CCL8 (known as MCP-2), big gastrin, gonadoliberin, neurotensin, orexin A, fibronectin, collagen 1 and TRH (thyrotropin-releasing hormone) was tested via SPR (data not shown). The tested antibody showed no cross reactivity with the several pyroglutamate-peptides. Additionally, the cross reactivity of antibody clone 13 to AβpE(3-40) and AβpE(11-30) were tested in SPR, whereby the antibody should be compared concerning its reactivity. In FIG. 20a real-time plot of clone 13 to AβpE(11-30) and AβpE(3-40) peptide over time is illustrated.

The SPR results indicate that clone 13 showed a weak cross reactivity to AβpE(3-40) but with 4 magnitudes lower than to AβpE(11-30). The ITC results (see section 2.4.3) show that the bond between Aβ11pE and clone 13 was mild entropic driven due to hydrophobic interactions. That means that in general, clone 13 could unspecifically interact with hydrophobic peptides e.g Aβ3(pE) which was confirmed by the above shown results of SPR. Summarizing, the anti Aβ11(pE) antibody showed an high affinity (see ITC results) and a good specificity.

2.5 Application of Anti Aβ11(pE) Antibody in Sandwich ELISA 2.5.1 Establishment of Auto-Ig-ELISA For the analysis of auto-immunglobulins in plasma samples from AD patients and healthy controls the anti Aβ11(pE), anti Aβ3(pE) and anti Bri-2(pE1) autoantibody ELISA's were established (see Table 5). The ELISA's were developed for the analysis of the different antibody classes IgG, IgM, IgA, subclasses (IgG2, IgG3) and total immunoglobulin Ig's. At the beginning of the optimization process, too high background signals were measured, whereby after immobilization of the peptide (200 ng/ml) no blocking was performed. Therefore ELISA-Blocker (−T) and PBS/10% FBS/0.05% Tween were tested for blocking as well as for dilution of samples and conjugate. ELISA-Blocker (−T) showed the lowest background signal and the highest signal-to-noise ratio in all auto-Ig-ELISA's.

Furthermore, a standard for the quantification of samples in anti Aβ11(pE) auto-Ig-ELISA were established. Therefore the purified and dialyzed mAb (clone 13) (see chapter 2.2) was tested as standard. The mAb is directed against the N-terminus of Aβ(pE11-x) and belongs to the mouse IgG class. In FIG. 21, the standard curve of the mAb clone 13 is shown. For the detection of the standard antibody (clone 13) rabbit anti-mouse Ig's (HRP) and in contrast for human plasma samples anti-human Ig's, IgG, IgG2, IgG3, IgM or IgA was used. A standard for each autoantibody class and subclass was not available but the comparison of autoantibody level in AD patients and control groups within each antibody class/subclass was possible because the samples were tested and quantified under identical conditions. However, the comparison of autoantibody concentrations between the classes/subclasses as well as between the auto-Ig-ELISA's wasn't admissible due to the quantification with the standard of class IgG.

The LOQ of the Aβ11(pE) auto-antibody ELISA was 55 pg/ml with S/N of 1.65 and the LOQ of Aβ3(pE) auto-antibody ELISA was 48.8 pg/ml with S/N ratio of 1.88. Summarizing, the mAb from hybridoma clone 13 was suitable as standard and was further used in the anti-Aβ11 (pE) auto-Ig-ELISA.

2.5.2 Development of Aβ(pE11-x) ELISA

The performance of the Aβ11(pE) ELISA according to the sandwich ELISA with 4G8 capture antibody and biotinylated anti Aβ11(pE) detection antibody showed weak or inconsistent signals (results not shown). The detection of peptide Aβ(pE11-30) as well as of Aβ(pE11-40) showed only weak signals. Both Aβ peptides are very hydrophobic and to avoid the adhesion of peptides at the vessel wall during the storage the peptide solutions were prepared (HFIP was evaporated and alkaline solved) immediately before usage in ELISA, but also no signals were detected. Possible problems could be caused by sterical hindrance between the capture 4G8 antibody with epitope Aβ(17-24) and the detection antibody with epitope Aβ(pE11-15). To test directly the antibody reactivity of 4G8 and anti Aβ11 (pE) antibody a direct ELISA with adsorbed Aβ peptide was performed. Immediately before usage the HFIP was evaporated and then the Aβ peptide was dissolved in NaOH (10 min at RT). The strong hydrophobic Aβ(pE11-30) peptide should be immediately diluted in PBS directly at the microplate to guarantee that the peptide during the dilution didn't adhere at polypropylene vial. In FIGS. 22 and 23, the ELISA signal by usage of biotinylated anti Aβ11(pE) antibody and 4G8 is shown. The anti Aβ11(pE) antibody showed a strong ELISA signal in a Aβ(pE11-30) concentration dependent manner and detected Aβ peptides in the range of nano grams. Concluding, the biotinylated anti Aβ11(pE) antibody recognized the peptide and was suitable for the application as detection antibody.

In contrast the biotinylated 4G8 antibody showed only a weak ELISA signal in a Aβ(pE11-30) concentration dependent manner.

Compared with clone 13 the signal of 4G8 was five times lower under the same conditions. Normally the commercially available 4G8 shows a good binding property to Aβ proteins (Schupf et al., Proc Natl Acad Sci USA. 2008 Sep. 16; 105(37):14052-7). However in the case of Aβ(pE11-30), 4G8 showed only weak binding signals. The antibody 4G8 was generated by immunization with synthetic peptide corresponding to the first 24 amino acids of the AR peptide and recognizes exclusively the sequence 17-24 of AR peptide (Kim et al., 1988). Therefore, 4G8 recognized other structures than that of the Aβ(pE11-30) peptide. Following the reason of low signal detection was the structure of used peptide. From this results could be concluded that the 4G8 antibody wasn't suitable as capture antibody in Aβ11(pE) ELISA which explained that only low or inconsistent signals were detected. In future, precoated plates with anti-human Aβ(35-40) mouse IgG mAb from the company IBL should be tested as capture antibody whereby the standard peptide Aβ(pE11-40) should be used.

2.5.3 Immunostaining with Aβ11(pE) Antibody

The immunostaining of brain sections from AD patients and transgenic APP/PS1 mice was performed with anti Aβ11(pE) antibody (clone 13). The IHC images of human AD cases 1 to 3 are shown in FIG. 24.

The staining sections of AD case 1, 2 and 3 indicate that Aβ11(pE) was extracellular deposited, whereby in the plaque core region of AD case 1 mainly Aβ11(pE) was stained. Concluding, Aβ11(pE) could be stained in the core region as well as in peripheral region of plaques. Furthermore intracellular deposits were clearly visible in AD case 3. The magnification (right bottom square) in AD case 3 showed that Aβ11(pE) depositions were stained directly beside the cell nucleus, visible as semicircular shape. Noticeable was that more intracellular Aβ11(pE) staining were detected than Aβ3(pE).

The results indicate that the monoclonal antibody clone 13 specifically recognizes both intracellular and extracellular Aβ11(pE) deposits.

Beside the human brain sections also sections of APP/PS1 transgenic mouse brain were examined for Aβ11(pE) depositions (see FIG. 25).

The IHC images of mice brain show vascular deposits of Aβ11(pE) peptides. Besides the clearly visible brown staining along the blood vessels in the mice brain also intracellular Aβ11(pE) deposits were visible. In contrast, in the sections of human brains the vascular deposits were not seen.

Summarizing, the results show that Aβ11(pE) deposits could have been detected intraneuronally, extraneuronally and also vascularly. Clone 13 showed an excellent reactivity against the pyroGlu peptides and could be used for immunostaining. So far, no source is known which showed that the deposition of Aβ11(pE) intracellularly and intercellularly in human AD brains occurs.

The deposition of Aβ peptides as plaques is one of the most prominent pathological features of AD and considered to be closely related to the pathogenesis of dementia in AD. The composition of plaques is not completely understood so far.

2.6 Autoantibody Levels in AD Patients and Healthy Controls

In the present study the level of autoantibodies of the classes and subclasses IgG, IgM, IgA, total Immunglobulins Ig's, IgG2 and IgG3 directed against the Aβ(pE11-x) epitope was studied. The aim was to find a potential diagnostic AD biomarker whereby a possible correlation between the Aβ autoantibody profiles of AD patients was analyzed. Therefore plasma samples which originate from patients with a clinical diagnosis of AD and from healthy control group were studied. The 13 plasma samples from AD patients and 30 healthy controls were obtained from the study PBD-0316 (T0+6 months). For this analysis the auto-Ig-ELISA's which were established in the present study (see section 1.4.2.1) were used. The results are presented in FIGS. 26 and 27.

In FIG. 26 and FIG. 27 the concentration of anti Aβ11(pE) autoantibodies of Ig's (total immunglobulins), IgG, IgG2, IgG3, IgM and IgA are shown. The mean level of all analyzed anti Aβ11(pE) antibody classes and subclasses, except IgG2, was increased in AD patients compared to the control group. The results of anti Aβ11(pE) autoantibodies showed no significant difference between AD and healthy controls and a great fluctuation of autoantibody level in plasma controls and AD patients.

---

What is claimed is:

1. A method of treatment, alleviating the effects, or delay of a neurodegenerative disease in a subject comprising:
   (A) administering of a pharmaceutically effective dose of an isolated monoclonal antibody to a subject in need thereof; or
   (B) administering of a pharmaceutically effective dose of a pharmaceutical composition comprising an isolated monoclonal antibody in combination with at least one pharmaceutically acceptable carrier or excipient to a subject in need thereof;
   wherein
   the neurodegenerative disease is selected from the group consisting of mild cognitive impairment, Alzheimer's disease, a Familial Alzheimer's dementia, and neurodegeneration in Down Syndrome;
   the monoclonal antibody binds to Aβ peptides between amino acid position 11 and an N-terminal pyroglutamate, AβpGlu(11), or variants thereof;
   the monoclonal antibody has a dissociation constant ($K_D$) value of $10^{-7}$ or less, and
   the variable part of the light chain of the antibody has the nucleotide sequence of SEQ ID NO: 51 or the amino acid sequence of SEQ ID NO: 52.

2. The method of claim 1, wherein the variable part of the heavy chain of the antibody has the nucleotide sequence of SEQ ID NO: 53 or the amino acid sequence of SEQ ID NO: 54.

3. The method of claim 1, wherein the antibody, Aβ 13-11-6, is obtained from a hybridoma cell line DSM ACC 3100, or a functional variant thereof.

4. The method of claim 1, wherein the antibody is a humanized or chimeric antibody, or an antibody fragment.

5. The method of claim 1, wherein the antibody is obtained from a hybridoma cell line DSM ACC 3100.

6. The method of claim 1, wherein the antibody is in combination with at least one pharmaceutically acceptable carrier or excipient.

7. The method of claim 1 wherein the method treats the neurodegenerative disease.

8. The method of claim 1 wherein the method alleviates the effects of the neurodegenerative disease.

9. The method of claim 1 wherein the method delays the neurodegenerative disease.

10. The method of claim 1 wherein the subject is a human subject.

11. A method of treatment, alleviating the effects, or delay of a neurodegenerative disease in a subject comprising:
    the administering of a pharmaceutically effective dose of an isolated monoclonal antibody to a subject in need thereof;
    wherein
    the neurodegenerative disease is selected from the group consisting of mild cognitive impairment, Alzheimer's disease, a Familial Alzheimer's dementia, and neurodegeneration in Down Syndrome;
    the monoclonal antibody binds to Aβ peptides between amino acid position 11 and an N-terminal pyroglutamate, AβpGlu(11), or variants thereof;
    the monoclonal antibody has a dissociation constant ($K_D$) value of $10^{-7}$ or less, and
    the variable part of the light chain of the antibody has the nucleotide sequence of SEQ ID NO: 51 or the amino acid sequence of SEQ ID NO: 52.

12. The method of claim 11 wherein the method treats the neurodegenerative disease.

13. The method of claim 11 wherein the method alleviates the effects of the neurodegenerative disease.

14. The method of claim 11 wherein the method delays the neurodegenerative disease.

15. The method of claim 11 wherein the subject is a human subject.

16. A method of treatment, alleviating the effects, or delay of a neurodegenerative disease in a subject, the method comprising:
    administering a pharmaceutically effective dose of a pharmaceutical composition to a subject in need thereof;
    wherein
    the neurodegenerative disease is selected from the group consisting of mild cognitive impairment, Alzheimer's disease, a Familial Alzheimer's dementia, and neurodegeneration in Down Syndrome;
    the pharmaceutical composition comprises an isolated monoclonal antibody;
    the monoclonal antibody binds to Aβ peptides between amino acid position 11 and an N-terminal pyroglutamate, AβpGlu(11), or variants thereof;
    the monoclonal antibody has a dissociation constant ($K_D$) value of $10^{-7}$ or less;

the monoclonal antibody is in combination with at least one pharmaceutically acceptable carrier or excipient; and the variable part of the light chain of the antibody has the nucleotide sequence of SEQ ID NO: 51 or the amino acid sequence of SEQ ID NO: 52.

17. The method of claim 16 wherein the method treats the neurodegenerative disease.

18. The method of claim 16 wherein the method alleviates the effects of the neurodegenerative disease.

19. The method of claim 16 wherein the method delays the neurodegenerative disease.

20. The method of claim 16 wherein the subject is a human subject.

* * * * *